US006093544A

United States Patent [19]
Gonsalves et al.

[11] Patent Number: 6,093,544
[45] Date of Patent: Jul. 25, 2000

[54] RUPESTRIS STEM PITTING ASSOCIATED VIRUS NUCLEIC ACIDS, PROTEINS, AND THEIR USES

[75] Inventors: Dennis Gonsalves; Baozhong Meng, both of Geneva, N.Y.

[73] Assignee: Cornell Research Foundation, Inc., Ithaca, N.Y.

[21] Appl. No.: 09/081,320

[22] Filed: May 19, 1998

Related U.S. Application Data

[60] Provisional application No. 60/047,147, May 20, 1997, and provisional application No. 60/069,902, Dec. 17, 1997.

[51] Int. Cl.[7] ..................................................... C12Q 1/68
[52] U.S. Cl. ............................. 435/6; 435/91.2; 435/7.1; 536/22.1; 536/24.32
[58] Field of Search ............................... 536/22.1, 24.32; 435/6, 91.2, 7.1

[56] References Cited

U.S. PATENT DOCUMENTS

| | | | |
|---|---|---|---|
| 4,358,535 | 11/1982 | Falkow et al. | 435/5 |
| 4,480,040 | 10/1984 | Owens et al. | 436/504 |
| 5,043,272 | 8/1991 | Hartley | 435/91 |
| 5,104,792 | 4/1992 | Silver et al. | 435/6 |
| 5,106,727 | 4/1992 | Hartley et al. | 435/6 |
| 5,196,305 | 3/1993 | Findlay et al. | 435/6 |
| 5,288,611 | 2/1994 | Kohne | 435/6 |
| 5,322,770 | 6/1994 | Gelfand | 435/6 |
| 5,328,825 | 7/1994 | Warren, III et al. | 435/6 |
| 5,503,999 | 4/1996 | Jilka et al. | 435/172.3 |

FOREIGN PATENT DOCUMENTS 0 571 911 A2  12/1993  European Pat. Off. .......... C12Q 1/68

OTHER PUBLICATIONS

Azzam, et al., "Detection of dsRNA in Grapevines Showing Symptoms of Rupestris Stem Pitting Disease and the Variabilities Encountered," *Plant Disease,* 75:960–964 (1991).

Meng et al., "Nucleotide Sequence and Genomic Organization of Grapevine Rupestris Stem Pitting–Associated Virus and Its Detection by RT–PCR," *Phytopathology,* 87:65–66 (1997).

Meng et al., "Rupestris Stem Pitting of Grapevines: Nucleotide Sequence, RT–PCR Detection, and Viral Origin of Associated DsRNA," 12th Meeting of the International Council for the Study of Viruses and Virus–Like Diseases of the Grapevine, Sep.–Oct., 1997.

Meng et al., "Nucleotide Sequence and Genome Structure of Grapevine Rupestris Stem Pitting Associated Virus–1 Reveal Similarities to Apple Stem Pitting Virus," *Journal of General Virology,* 79:2059–2069 (1998).

Wetzel et al., "A Highly Sensitive Immunocapture Polymerase Chain Reaction Method for Plum Pox Portyvirus Detection," *Journal of Virological Methods,* 39:27–37 (1992).

Krastanova et al., "Tranformation of Grapevine Rootstocks With the Coat Protein Gene of Grapevine Fanleaf Nepovirus," *Plant Cell Reports,* 14:550–554 (1995).

Schell et al., "Transformation of 'Nova' Tangelo With the Coat Protein Gene of Citrus Tristeza Closterovirus," *Phytopathology,* 84:1076 (1994).

Beachy et al., "Coat Protein–Mediated Resistance Against Virus Infection," *Annu. Rev. Phytopathol.,* 28:451–474 (1990).

Le Gall et al., "Agrobacterium–Mediated Genetic Transformation of Grapevine Somatic Embryos and Regeneration of Transgenic Plants Expressing the Coat Protein of Grapevine Chrome Mosaic Nepovirus (GCMV)," *Plant Science,* 102:161–170 (1994).

Salati et al., "Detection of Grapevine Viruses Associated with Leafroll, Corky Bark, and Rupestris Stem Pitting Using F(ab')$_2$–ELISA and dsRNA Techniques," *Am J. Enol. Vitic.* 45(3):372 (1994).

Monette et al., "Double–Stranded RNA from Rupestris Stem Pitting–Affected Grapevines," *Vitis* 28:137–144 (1989).

Monette et al., "The Use of In Vitro Cultures in the Investigation of Grapevine Virus–like Diseases," *Canad. J. Plant Pathol.* 12(3):337 (1990).

Credi, "Characterization of Grapevine Rugose Wood Disease Sources from Italy," *Plant Disease* 81(11):1288–1292 (1997).

Azzam et al., "Detection of dsRNA from Cleistothecia and Conidia of the Grape Powdery Mildew Pathogen, *Uncinula necator,*" *Plant Disease* 75(9):964–967 (1991).

*Primary Examiner*—W. Gary Jones
*Assistant Examiner*—Joyce Tung
*Attorney, Agent, or Firm*—Clark & Elbing LLP

[57] ABSTRACT

The present invention relates to an isolated protein or polypeptide corresponding to a protein or polypeptide of a *Rupestris* stem pitting associated virus. The encoding DNA molecule, either alone in isolated form, in an expression system, a host cell, or a transgenic grape plant, is also disclosed. Other aspects of the present invention relate to a method of imparting *Rupestris* stem pitting associated virus resistance to grape plants by transforming them with the DNA molecule of the present invention, and a method of detecting the presence of a *Rupestris* stem pitting associated virus, such as RSPaV-1, in a sample.

4 Claims, 16 Drawing Sheets

FIG. 4A

| | |
|---|---|
| Consensus | .*GTFG.GKS.L.-K.*.#.*.GK..*FVSPRR#LA.#..#......#K#G.**......V.T*E. |
| PVM Rep-II | (1163)IVGTFGSGKSTLF-KNLLKYGAGKSLDFVSPRRALAEDFKRTVGMNERGGRAKAGQE----NWRVTTLET |
| ASPV Rep-II | (1372)ILGTFGCGKSSLF-KKFIEKSPGKAITFVSPRRSLAESINHDLGLARVGGK-KTGKSKDLKNVRVKTFEL |
| RSPaV-1 Rep-II | (1354)VLGTFGAGKSFLY-KSFMKRSEGKFVTFVSPRRALANSIKNDLEMDDSCKVAKAGRSKKEGWD-VVTFEV |
| | A |

| | |
|---|---|
| Consensus | F#..#..#*.G*.V#.DE.QL*PPGY*DL..*....#..*.#*GDP*QS.YD#.#DR.*###..***.*. |
| PVM Rep-II | FLARVEFLTEGQVVILDEMQLYPPGYFDLVVSMLKVDVRLFLVGDPAQSDYDSEKDRLVLGAMEENMSVV |
| ASPV Rep-II | FILHLDSIKEGHTVVIDEIQLFPPGYIDLIILGLKPNVNIIIAGDPCQSDYDCSSDRHIFAGSESDIMRI |
| RSPaV-1 Rep-II | FLRKVAGLKAGHCVIFDEVQLFPPGYIDLCLLIIRSDAFISLAGDPCQSTYDSQKDRAILGAEQSDILRL |

| | |
|---|---|
| Consensus | L.*..Y.#**.S.RF.N*.F..RLPC...K...T.....*...#....*##...*.....VLVSSF*EK* |
| PVM Rep-II | LGAREYNYKVRSHRFLNCNFIGRLPCEINKDDCTIDEPHIMRMHL--ENLLDVAEEYKSVVLVSSFDEKM |
| ASPV Rep-II | LSGRSYKFNILSQRFRNPVFYGRLPCNLNKTRLTLDEEEYTLWDSIQEFSMMGRKDCPV-VLVSSFEEKK |
| RSPaV-1 Rep-II | LEGKTYRYNIESRRFVNPMFESRLPCHFKKGSMTAAFADYAIFHNMHDFLLARSKGPLDAVLVSSFEEKK |

| | |
|---|---|
| Consensus | *V....*.*...#T#GESTGL*F..G.I*##..S..T.*RRW.TAL*RF**##..#N..G........** |
| PVM Rep-II | VVCAHLPEA-KVLTFGESTGLTFMHGTIYISAVSERTNERRWITALRRFRFNLCFVNCSGMDYQQLAGRY |
| ASPV Rep-II | IVAAHLGLKMKCITYGESTGLNFQKGAILVTYESALTSDRRWWTALSRFSHDIHFINGMGVTWDNAITHF |
| RSPaV-1 Rep-II | IVQSYFGMKQLTLTFGESTGLNFKNGGILISHDSFHTDDRRWLTALSRFSHNLDLVNITGLRVESFLSHF |

| | |
|---|---|
| Consensus | .G***..F#*.......*.**LPG.*.#.#**...#G#.EGVRE#KL.GDPWLK.M.*L*Q..*.E.*#. |
| PVM Rep-II | KGRVRSKFLCKTAIPDDLNSMLPGQALFKSEYPRLIGKDEGVREEKLAGDPWLKTMINLYQAPEVEIAEE |
| ASPV Rep-II | VGKPLHKFFTKRACNDDIIDLLPGRPELIEGFQSQVGADEGVREAKLVGDPWLKTKIFLGQNPDFEIEIA |
| RSPaV-1 Rep-II | AGKPLYHFLTAKSGENVIRDLLPGEPNFFSGFNVSIGKNEGVREEKLCGDPWLKVMLFLGQDEDCEVEEM |

| | |
|---|---|
| Consensus | ......E#WF*TH*P...LE#.RA.WV.K...#E#RE#R.G...*.QF.*.H....G.-#L.NA.ER#E. |
| PVM Rep-II | PEVVMQEEWFRTHLPRDELESVRAQWVHKILAKEYREVRMGDMVSEQFTHDHTKQLGAKQLTNAAERFET |
| ASPV Rep-II | DEVEAAEDWFKTHIPIMSLEAVRAQWVHKLISREDREFRIGDITTEQFTDDHSKNRGQ-ELTNAAERYEA |
| RSPaV-1 Rep-II | ESECSNEEWFKTHIPLSNLESTRARWVGKMALKEYREVRCGYEMTQQFFDEHRGGTGE-QLSNACERFES |

FIG. 4B

| | |
|---|---|
| Consensus | IYPRH**.D..TFLMAV.KRL.FS.P..E.LA**#GK*LL*.FL...PL#.*H#..*..EA*-..F |
| PVM Rep-II | IYPRHRASDTVTFLMAVKKRLSFSNPGKEKGNLFHAASYGKALLSEFLKRVPLKPNHNVRFMEEAL-WNF |
| ASPV Rep-II | IYPRHKGTDTATFLMAVKKRLSFSSPAAEHAKLRRAKPFGKFLLDTFLKRVPLNSSHDEKMMQEAV-HAF |
| RSPaV-1 Rep-II | IYPRHKGNDSITFLMAVRKRLKFSKPQVEAAKLRRAKPYGKFLLDSFLSKIPLKASHNSIMFHEAV-QEF |
| | |
| Consensus | E.KK.SKS#ATIENH.GRSC#DW..D#A*IF*KSQ.CTKFDNR-.R#AKA*Q***CFQH#VL.RFAPYMR |
| PVM Rep-II | EEKKLSKSAATIENHSGRSCRDWPTDVAQIFSKSQLCTKFDNR-FRVAKAAQSIVCFQHAVLCRFAPYMR |
| ASPV Rep-II | EEKKLSKSMATIENHSGRSCEDWPVDKALIFMKSQLCTKFDNR-FRSAKAGQTLACFQHSVLCRFAPYMR |
| RSPaV-1 Rep-II | EAKKASKSAATIENHAGRSCRDWLLDVALIFMKSQHCTKFDNR-LRVAKAGQTLACFQHAVLVRFAPYMR |
| | |
| Consensus | YIE.K....L..N.YIHSGK##*#L..WV.*..-F.*#CTESDYEAFDASQD*FI*AFEL..MK*L*LP. |
| PVM Rep-II | YIEMKVHEVLPKNYYIHSGKGLEELDAWVKKGK-FDRICTESDYEAFDASQDEFIMAFELELMKYLRLPS |
| ASPV Rep-II | YIESKVTEVLPKNLYIHSGKNIDDLAAWVTTSK-FNGVCTESDYEAFDASQDHFILAFELEVMKFLGLPS |
| RSPaV-1 Rep-II | YIEKKLMQALKPNFYIHSGKGLDELNEWVRTRG-FTGICTESDYEAFDASQDHFILAFELQIMKFLGLPE |
| | |
| Consensus | DLI.DY.FIK.*LGSKLG*F.IMRF*GEASTFLFNT*ANMLFTF*RY.*.G.E.I.FAGDDMCA*#RL.. |
| PVM Rep-II | DLIEDYKFIKTSLGSKLGNFAIMRFSGEASTFLFNTLANMLFTFMRYNIRGDEFICFAGDDMCASRRLQP |
| ASPV Rep-II | DLIADYTFIKTHLGSKLGSFAIMRFTGEASTFLFNTMANMLFTFLRYDLNGREAICFAGDDMCANSRLKV |
| RSPaV-1 Rep-II | DLILDYEFIKIHLGSKLGSFSIMRFTGEASTFLFNTMANMLFTFLRYELTGSESIAFAGDDMCANRRLRL |
| | B |
| Consensus | .......FL..I.LKAKVQF#..-----PTFCGW.L...G#*KKP#L..ER.#IA*E#.NL*NCIDNYAIE |
| PVM Rep-II | TKKFAHFLDKLKLKAKVQFVQFVN--KPTFCGWHLCPDGIYKKPQLVLERMCIAKEMNNLSNCIDNYAIE |
| ASPV Rep-II | TNRFSNFLDKIKLKAKVQFTAT-----PTFCGWGLCEHGVFKKPDLVLERLQIARETRNLENCIDNYAIE |
| RSPaV-1 Rep-II | KTEHEGFLNMICLKAKVQFVSN-----PTFCGWCLFKEGIFKKPQLIWERICIAREMGNLENCIDNYAIE |
| | |
| Consensus | V*#AY.#GE.#...#*##EV.A*YNCVR*.V###H |
| PVM Rep-II | VAYAYKLGEKAVNRMDEEEVAAFYNCVRIIVRNKH |
| ASPV Rep-II | VSCAYKMGENLNLYLTPQEVDAHYNCVRFIVQHNH |
| RSPaV-1 Rep-II | VSYAYRLGELAIEMMTEEEVEAHYNCVRFLVRNKH |

*FIG. 4C*

| | |
|---|---|
| Consensus | M...#..L..*.F......L-..P.V.H.VPG*GK##LI###...#.*#.A.T#GV*#.#*#.G.*I*.. |
| PVM 25K | MDVIVDLLYKYKFERLSNKL-VCPIVVHCVPGAGKSSLIRELLELDSRFCAYTAGVEDQPRLSGNWIRKW |
| ASPV 25K | METVLSLLNEFGFERTVEPL-SDPIVVHAVPGSGKTTLIKQALIRNNNIEAVTFGVPEKANIHGTYIKKA |
| RSPaV-1 24.4K | MNNLVKALSAFEFVGVFSVL-KFPVVIHSVP<u>GSGKS</u>SLIRELISEDENFIAFTAGVPDSPNLTGRYIKPY |
| | |
| Majority | #.G....G#..*LDEY**.-....**..LF*DP*Q-N.#....A*F*.#...RFG..T#..L...G..#. |
| PVM 25K | S-GQQPEGKFVVLDEYTLL-TEVPPVFALFGDPIQSNTSAVQRADFVCSVSRRFGSATCGLLRELGWNVR |
| ASPV 25K | RQGQRGRGNYSILDEYLSG-EYSTGFNCLFSDPYQ-NHGDCLRAHFIGRCSHRFGRQTVQILRDLGYNIA |
| RSPaV-1 24.4K | SPGCAVPGKVNILDEYLSV-QDFSGFDVLFSDPYQ-NISIPKEAHFIKSKTCRFGVNTCKYLSSFGFKVS |
| | |
| Majority | --S...D.V.#...*#*#..*G*.**..*#..*#...H..E.*.#G.TF.#VT...#.......#. |
| PVM 25K | --SEKADLVQVSDIYTKD-PLGKVVFSEEEVGCLLRSHGVEALSLQEITGQTFEVVTFVTSENSPVINRA |
| ASPV 25K | --SSKEDIVEKKNIFQLIEPEGVIICLEKGVEDFLKWHSVEYKFPCQVRGATFDIVTFIHEKPLEELVGP |
| RSPaV-1 24.4K | --SDGLDKVIVGSPFTLDV-EGVLICFGKEAVDLAVAHNSEFKLPCEVRGSTFNVVTLLKSRDPTPEDRH |
| | |
| Majority | ..-#.*.TRHR.**-.... |
| PVM 25K | AA-YQCMTRHRRLC-TSVS |
| ASPV 25K | DL-FVALTRHRSKL-VLVSN |
| RSPaV-1 24.4K | WF-YIAATRHREKL-IIMQ |

*FIG. 5A*

```
Consensus       MP*.*-----P....K...*..*G....#V*..L..S.LP..GD**H..PHGG.Y#DGTK#*.Y**P..*
PVM 12K         MP-----LTPPPDFTKVYLSAALGVSLALVVWLLIRSTLPVVGDRDHNLPHGGWYRDGTKSVFYNSP--G
ASPV 12K        MPFAQ-----PPDYSKSVFPIAVGIAVAVVLFTLTRSTLPQVGDNIHNLPHGGNYQDGTKRISYCGPRDS
RSPaV-1 12.8K   MPFQQ-----PANWAKTITPLTVGLGIGLVLHFLRKSNLPYSGDNIHQFPHGGRYRDGTKSITYCGPKQS Majority        ***S.....*.........*.L*..*.*#..*..**..*##.*.*....*......
PVM 12K         RLNSIEARKAPLLGQPWAIVVLLVL---LIWASHKLGRPNCR-ACA--GS----HT
ASPV 12K        FPSSSLIS-SGTPMIIGIIIFLIFAIYVSEKWSRSGSRRCSCCVPGAPACTATVHE
RSPaV-1 12.8K   FPSSGIFGQSENFVPLMLVIGLIAFIHVLSVWN-SGLGRNCNCHPNPCSCRQQ
```

*FIG. 5B*

```
Consensus      M....*..L....#V.*...L....#....*...C.*..TGES.....C..***..#.**.##..##.*G
PVM 7K         MIVYVLVGLSAFCIV---LYL---ISQGQS---DCVVLITGESVRVQGCRIDGEFGS----VLSKLKPFG
ASPV 8K        MFPRSGLGLAVAAAVVAYLVLLLAQQLYMSNSSQCTIVITGESVSVVGCVYSEAFIELVKGLKPYYHPLG
RSPaV-1 8.4K   MYCLFGI-LVLVGIVIAIQILAHVDSSSG-NHQGCFIRATGESILIENCGPSEALASTVKEVLGGLKALG Majority       .............
PVM 7K         CGSFRS
ASPV 8K
RSPaV-1 8.4K   VSRAVEEIDYHC
```

FIG. 5C

```
Consensus          *..TLR#.C..YA*.*WN..L.*..PPA*W#.*#F.....#A*FD*F.*V....#**P..G..R.PT.*E
PVM CP      (188)  DAETLRRVCRLYAPVTWNHMLTHNAPPAEWAAMGFQYEDRFAPFDCFDYVENTAAVQPLEGLIRRPTPRE
ASPV CP     (301)  EGCTLRQYCAFYAKHVWNLMLQTQSPPANWVGKEFKFETRYAAFDFFFGVESTASLEPADGLIRLPTQAE
RSPaV-1 CP  (142)  EVTTLRRFCMYYAKIVWNIHLETGIPPANWAKKGFNENEKFAAFDFFLGVTDESALEPKGGIKRAPTKAE Majority           .VA*..*.*.*..R.#..**..##*.*E..GG..G.....*........
PVM CP             KVAHNTHKDIAL-RGANRNQVFSSLNAEVTGGMNGPELTRDYVKSNRK
ASPV CP            RVANATSKEIQMYRIRSMEGTQAVNFGEVTGGKIGP---KPVLSI-RK
RSPaV-1 CP        MVANIASFEVQVLRQAMAEGKRSSNLGEISGGTAGALINNPFSNVTHE
```

*FIG. 5D*

```
Consensus     ...G.T.A...AA.TC..C..CA.TTC.....T.CA.TA.TT...C..TTT...AA.G.TG.....A.CCT...
ASPV 3'UTR    TTAGTTAATTAATTCTCCTGCA-TTCAAT..TTCAGTACTTATGCTTTTTAGTAAAGTTGATCCCAACCTAAC
RSPaV-1 3'UTR ..GGATGACGAAGTCAGGCGACAATTCCGCAGTCCAATAATTCCCGATTT--CAAGGCTGGGTTAAGCCTGTT Consensus     CG..GG....C..T.......GT.T.....TT.CATGCT..A.C.TATTT............TGT........
ASPV 3'UTR    CG--GGGCGGCTATGT.....GTGTGTTCTTCATGCTTAGCTTATTT--------TGT........
RSPaV-1 3'UTR CGCTGGAATACCGTACTAATAGTATTCCCTTTCCATGCTAAATCCTATTTAATATATAAGGTGTGGAAAGTAA Consensus     ........TTT...............TAG.TTT....TC
ASPV 3'UTR    .........TTTAAC--------TAGATTT...TC
RSPaV-1 3'UTR AAGAAGATTTGGTGTGTTTTTATAGTTTTCATTC
```

*FIG. 6A*

```
Consensus     . . . . . . . . . . . . . . . . . . . . . . . . . . . . . . . . . . . . . . . . . . . . . . . . . . . . . . . . . . . . . . . . . . . . . . . . . . . .
PVM 3' UTR    . . . . . . . . . . . . . . . . . . . . . . . . . . . . . . . . . . . . . . . . . . . . . . . . . . . . . . . . . . . . . . . . . . . . . . . . . . . .
RSPaV-1 3UTR  GGATGACGAAGTCAGGCGACAATTCCGCAGTCCAATAATTCCCGATTCAAGGCTGGGTTAAGCCTGTTCGCT Consensus                                        CCAT . .  TAAATCCTATTTAATATATAA. GTGTG . .  A . . . . AAA . A
PVM 3' UTR                                       CCAT . .  TAAATCCTATTTAATATATAACGTGTGCTACTATAAATA
RSPaV-1 3UTR  GGAATACCGTACTAATAGTATTCCCTTTCCATGCTAAATCCTATTTAATATATAAGGTGTGGAAAGTAAAGA Consensus     A . A . TTGGT . T . T . . TAT . . TTTT . . . . .
PVM 3' UTR    AACTTGGTTTTTAACTAT . . TTTTAGCCA
RSPaV-1 3UTR  AGATTGGTGTGTTTTATAGTTTTCATTC
```

RUPESTRIS STEM PITTING ASSOCIATED VIRUS NUCLEIC ACIDS, PROTEINS, AND THEIR USES

This application claims the benefit of U.S. Provisional Patent Applications Ser. Nos. 60/047,147, filed May 20, 1997, and 60/069,902, filed Dec. 17, 1997.

This work was supported by the U.S. Department of Agriculture Clonal Repository—Geneva, Grant Nos. 58-2349-9-01 and 58-2349-9 and U.S. Department of Agriculture Cooperative Agreement Grant Nos. 58-1908-4-023, 58-3615-5-036, and 58-3615-7-060. The U.S. Government may have certain rights in the invention.

FIELD OF THE INVENTION

The present invention relates to *Rupestris* stem pitting associated virus ("RSPaV") proteins, DNA molecules encoding these proteins, and diagnostic and other uses thereof.

BACKGROUND OF THE INVENTION

The world's most widely grown fruit crop, the grape (Vitis sp.), is cultivated on all continents except Antarctica. However, major grape production centers are in European countries (including Italy, Spain, and France), which constitute about 70% of the world grape production (Mullins et al., *Biology of the Grapevine*, Cambridge, U.K.:University Press (1992)). The United States, with 300,000 hectares of grapevines, is the eighth largest grape grower in the world. Although grapes have many uses, a major portion of grape production (~80%) is used for wine production. Unlike cereal crops, most of the world's vineyards are planted with traditional grapevine cultivars, which have been perpetuated for centuries by vegetative propagation. Several important grapevine virus and virus-like diseases, such as grapevine leafroll, corky bark, and *Rupestris* stem pitting ("RSP"), are transmitted and spread through the use of infected vegetatively propagated materials. Thus, propagation of certified, virus-free materials is one of the most important disease control measures. Traditional breeding for disease resistance is difficult due to the highly heterozygous nature and outcrossing behavior of grapevines, and due to polygenic patterns of inheritance. Moreover, introduction of a new cultivar may be prohibited by custom or law. Recent biotechnology developments have made possible the introduction of special traits, such as disease resistance, into an established cultivar without altering its horticultural characteristics.

Many plant pathogens, such as fungi, bacteria, phytoplasmas, viruses, and nematodes can infect grapes, and the resultant diseases can cause substantial losses in production (Pearson et al., *Compendium of Grape Diseases*, American Phytopathological Society Press (1988)). Among these, viral diseases constitute a major hindrance to profitable growing of grapevines. About 34 viruses have been isolated and characterized from grapevines. The major virus diseases are grouped into: (1) the grapevine degeneration caused by the fanleaf nepovirus, other European nepoviruses, and American nepoviruses, (2) the leafroll complex, and (3) the rugose wood complex (Martelli, ed., *Graft Transmissible Diseases of Grapevines, Handbook for Detection and Diagnosis*, FAO, UN, Rome, Italy (1993)).

Rugose wood (RW) complex is a term to describe a group of graft-transmissible diseases which are important and widespread on grapevines grown world-wide. Symptoms of RW are characterized by pitting, grooving, or distortion to the woody cylinder of the grapevine scion, rootstock, or both. Based on symptoms developed on different indicator plants after graft inoculation, RW complex can be divided into four components: Kober 5BB stem grooving (KSG), LN 33 stem grooving (LNSG), grapevine corky bark (GCB), and *Rupestris* stem pitting (RSP) (Martelli, "Rugose Wood Complex," in *Graft-Transmissible Diseases of Grapevines, Handbook for Detection and Diagnosis*, pp. 45–54, Martelli, ed., Food and Agriculture Organization of the United Nations, Rome, Italy (1993)). Because RW can cause severe decline and death to grapevines (Savino et al., "Rugose Wood Complex of Grapevine: Can Grafting to Vitis Indicators Discriminate Between Diseases?", in *Proceedings of the 9th Meetings of the International Council for the Study of Viruses and Virus Diseases of the Grapevine*, Anavim, Israel (1989); Credi and Babini, "Effect of Virus and Virus-like Infections on the Growth of Grapevine Rootstocks," *Adv. Hort. Sci.*, 10:95–98 (1996)), it has been included in healthy grapevine detection schemes used in major grapevine growing countries including Italy, France, and the United States.

RSP was discovered in California in the late 1970s (Prudencio, "M. Sc. Thesis: Comparative Effects of Corky Bark and *Rupestris* Stem Pitting Diseases on Selected Germplasm Lines of Grapes," University of California, Davis, Calif., 36 pages (1985); Goheen, "*Rupestris* Stem Pitting," in *Compendium of Grape Diseases*, p. 53, Pearson and Goheen, eds., American Phytopathological Society Press, St. Paul, Minn., USA (1988) ("Goheen")). The disease was defined by Goheen as follows: after graft inoculation with a chip bud from an infected grapevine, the woody cylinder of the indicator plant *Vitis rupestris* Scheele St. George ("St. George") develops a narrow strip of small pits extending from the inoculum bud to the root zone. Grafted St. George plants were checked for wood symptoms 2 to 3 years after inoculation. In contrast to GCB, which elicits pitting and grooving on St. George and LN 33, RSP does not produce symptoms on the latter (Goheen, "*Rupestris* Stem Pitting," in *Compendium of Grape Diseases*, p. 53, Pearson and Goheen, eds., American Phytopathological Society Press, St. Paul, Minn., USA (1988)).

RSP is probably the most common component of the RW complex on grapevines. Surveys in California revealed a high disease incidence in many grapevine cultivars imported from Western Europe and Australia (Goheen, "*Rupestris* Stem Pitting*," in *Compendium of Grape Diseases*, p. 53, Pearson and Goheen, eds., American Phytopathological Society Press, St. Paul, Minn., USA (1988)). An examination of indexing records in California compiled over 23 years revealed RSP infection in 30.5% of 6482 grapevine selections introduced from around the world (Golino and Butler, "A Preliminary Analysis of Grapevine Indexing Records at Davis, Calif.," in *Proceedings of the 10th Meeting of the ICVG*, pp. 369–72, Rumbos et al., eds., Volos, Greece (1990)). Indexing in New York State showed that 66% of 257 grapevines tested on St. George developed typical small pits below the inoculum bud or around the woody cylinder (Azzam and Gonsalves, Abstract: "Survey of Grapevine Stem-Pitting in New York and Isolation of dsRNA from a Grapevine Selection Infected with Stem Pitting," *Phytopathology* 78:1568 (1988)). Furthermore, several reports have indicated that RSP is the most frequently detected component of the RW complex in Italy (Borgo and Bonotto, "Rugose Wood Complex of Grapevine in Northeastern Italy: Occurrence of *Rupestris* Stem Pitting and Kober Stem Grooving," in *Extended Abstracts of the 11th Meeting of the International Council for the Study of Viruses and Virus Diseases of the Grapevine (ICVG)*, pp.

61–62, Gugerli, ed., Montreux, Switzerland (1993); Credi, "Differential Indexing Trials on Grapevine Rugose Wood Syndrome," *Extended Abstracts of the 11th Meeting of the International Council for the Study of Viruses and Virus Diseases of the Grapevine (ICVG)*, p. 63, Gugerh, P., ed., Montreux, Switzerland (1993)).

The effect of RSP on growth, yield, and grapevine quality is not well understood and, thus, subject to debate. The reason for this ambiguity is the absence of a rapid and sensitive diagnostic tool. RSP is the most difficult grapevine disease to diagnose. Serological or molecular methods are not available for diagnosing RSP. Biological indexing on St. George, as described above, has remained the only approach to diagnose RSP. Biological indexing is labor intensive, time consuming (i.e., often requiring up to about three years to obtain results), and, by its very nature, subjective. Moreover, symptoms on St. George can be variable and not exactly as those defined by Goheen. In particular, Credi, "Characterization of Grapevine Rugose Wood Sources from Italy," *Plant Disease*, 82:1288–92 (1997), recently showed that some RSP infected grapevines induced pitting that is restricted to below the inoculum bud, while others induced pitting around the woody cylinder of inoculated St. George. Thus, the present method of identifying the presence of RSP is not entirely adequate.

The etiology of RSP is unknown. Efforts to isolate virus particles from RSP-infected grapevines and to mechanically transfer the causal virus(es) to herbaceous host plants failed (Azzam and Gonsalves, "Detection of in Grapevines Showing Symptoms of *Rupestris* Stem Pitting Disease and the Variabilities Encountered," *Plant Disease*, 75:96–964 (1991)). However, a major dsRNA species of ca. 8.3 kb, accompanied by a smaller dsRNA of ca. 7.6 kb, was consistently isolated from one Pinot Gris and four Pinot Noir clones that had been indexed positive for RSP (Walter and Cameron, "Double-Stranded RNA Isolated from Grapevines Affected by *Rupestris* Stem Pitting Disease," *Am. J. of Enology and Viticulture*, 42:175–79 (1991)). In addition, a third dsRNA of ca. 5.5 kb was observed in three clones. Likewise, an apparently similar dsRNA species of ca. 8.0 and 6.7 kbp was isolated from dormant canes of RSP-infected grapevines collected from California, Canada, and New York (Azzam and Gonsalves, "Detection of dsRNA in Grapevines Showing Symptoms of *Rupestris* Stem Pitting Disease and the Variabilities Encountered," *Plant Disease*, 75:960–64 (1991)). Six of eight Californian and three of five Canadian samples contained these two dsRNA species. However, results of New York samples were not consistent. Among eight RSP infected grapevine selections tested, only one showed these two dsRNAs. Using explants growing in tissue culture as source materials, dsRNA of ca. 359 bp was isolated from 21 of 31 grapevine cultivars, all of which were previously indexed on St. George and considered to be infected with RSP (Monette et al., "Double-Stranded RNA from *Rupestris* Stem Pitting-Affected Grapevines," *Vitis*, 28:137–44 (1989)).

In view of the serious risk RSP poses to vineyards and the absence of an effective treatment of it, the need to prevent this affliction continues to exist. Moreover, the absence of a rapid and accurate diagnostic assay prevents proper identification of RSP. The present invention is directed to overcoming these deficiencies in the art.

SUMMARY OF THE INVENTION

The present invention relates to an isolated protein or polypeptide corresponding to a protein or polypeptide of a RSP virus. The encoding RNA molecule or DNA molecule, in either isolated form or incorporated in an expression system, a host cell, or a transgenic Vitis scion or rootstock cultivar, are also disclosed.

Another aspect of the present invention relates to a method of imparting RSP virus resistance to Vitis scion or rootstock cultivars by transforming them with a DNA molecule encoding the protein or polypeptide corresponding to a protein or polypeptide of a RSP virus.

The present invention also relates to an antibody or binding portion thereof or probe which recognizes proteins or polypeptides of the present invention.

Still another aspect of the present invention relates to diagnostic tests which involve methods for detecting the presence of a RSP virus in a sample. The methods include the use of an antibody or binding portion of the present invention (i.e., in an immunoassay), or a nucleic acid probe obtained from a DNA molecule of the present invention (i.e., in a nucleic acid hybridization assay or gene amplification detection procedure). The antibody or binding portion thereof, or nucleic acid probe, is introduced into contact with the sample, whereby the presence of *Rupestris* stem pitting virus in the sample is detected using an assay system.

The characterization of an RSP virus is particularly desirable because it will allow for the determination of whether the virus is associated to the specific (restricted) or nonspecific (nonrestricted) pitting symptoms of RSP, or to both. Also, RSP virus resistant transgenic variants of the current commercial grape cultivars and rootstocks allows for more complete control of the virus while retaining the varietal characteristics of specifics cultivars. Furthermore, these variants permit control over RSP virus transmitted by infected scions or rootstocks. Moreover, the diagnostic tests offer significant improvement over conventional diagnostic means currently employed, namely, rapid results and greater accuracy.

BRIEF DESCRIPTION OF THE DRAWINGS

FIG. 4A is a comparative sequence listing of amino acid sequences of region I (aa 1–372) of RSPaV-1 ORF1 with the corresponding sequences of carlavirus PVM and ASPV. The methyltransferase motif is underlined. Capital letters indicate consensus residues. FIG. 4B is a comparative sequence listing of amino acid sequences of region II (aa 1354 to end) of RSPaV-1 ORF1 with the corresponding regions of ASPV and PVM carlavirus. In FIG. 4B, the NTP binding motif is underlined at (A) and the GDD containing sequence is underlined at (B). In FIGS. 4A and 4B, capital letters indicate consensus residues, the symbol * indicates identical amino acid residues between RSPaV-1 and ASPV, and the symbol # indicates identical amino acid residues between RSPaV-1 and PMV.

FIGS. 5A–D are comparative sequence listings of amino acid sequences for ORF2, ORF3, ORF4, and a C-terminal part of ORF5 (CP) of RSPaV-1, respectively, with ASPV and PVM carlavirus. In FIG. 5A, the NTP binding motif, located near the C terminus of ORF2, is underlined. In FIG. 5D, the conserved motif (RR/QX--XFDF), located in the central region of the coat proteins and proposed to be involved in the formation of a salt bridge structure, is underlined. In each of the figures, capital letters indicate consensus residues. The symbol * indicates identical amino acid residues between RSPaV-1 and ASPV, and the symbol # indicates identical amino acid residues between RSPaV-1 and PMV. In FIG. 5D, numbers which appear in parentheses and precede the sequences indicate the start points of the C-terminal portions of CPs being compared.

FIG. 6A is a comparative sequence listing of DNA nucleotide sequences for the 3' untranslated region (UTR) of RSPaV-1 and ASPV. FIG. 6B is a comparative sequence listing of DNA nucleotide sequences for the 3' untranslated region (UTR) of RSPaV-1 and PVM. Clustal method of MegAlign (DNASTAR) was used to generate sequence alignments. The 21 identical consecutive nucleotides between RSPaV-1 and PVM are indicated as shadowed letters.

FIG. 9 is a comparative alignment of nucleotide sequences of seven other clones with the comparable region of RSPaV-1. Shaded areas indicate identical nucleotide sequences, whereas white boxes represent different nucleotide sequences.

DETAILED DESCRIPTION OF THE INVENTION

Figure 1:
FIG. 1 is a photograph of St. George indicators which comparatively display the symptoms of RSP. The St. George indicator (a) has been graft-inoculated with infected bud wood from a grapevine accession, resulting in the indicator displaying pitting below the inoculum bud, as indicated by an arrow. This RSP symptom was defined by Goheen, "*Rupestris* Stem Pitting," in *Compendium of Grape Diseases*, p. 53, Pearson and Goheen, eds., American Phytopathological Society Press, St. Paul, Minn., USA (1988), which is hereby incorporated by reference. The St. George indicator (b) was not graft-inoculated and represents a normal appearance.

The present invention relates to isolated DNA molecules encoding for the proteins or polypeptides of a *Rupestris* stem pitting associated virus. Since the nucleotide sequence was derived from cDNA clones of the dsRNA that was associated with RSP, the viral agent has been designated as *Rupestris* stem pitting associated virus ("RSPaV"). RSP is likely caused by one or a number of viral strains. The genome of each RSPaV has a plurality of open reading frames, each containing DNA molecules in accordance with the present invention. The complete genome of one strain has been sequenced and the strain is designated RSPaV-1. Substantial portions of the genomes of two other RSPaV strains have also been sequenced. These strains are designated by their clone names, RSP47-4 and RSP158.

The DNA molecule which constitutes the complete RSPaV-1 genome comprises the nucleotide sequence corresponding to SEQ. ID. No. 1 as follows:

```
CGATAAACAT AACAACAGAA TCTGCATTGC AGTAATATTC CTTGAATATA ATTGCAACGC        60

AATGGCCCTC TCTTATAGGC CTGCTGTTGA AGAGGTGCTC GCAAAATTCA CCTCTGATGA       120

ACAATCCAGG GTTTCTGCTA CAGCTCTCAA GGCATTAGTA GACTTAGAGG AAAGTCAGCA       180

CAATTTGTTC TCTTTCGCAT TGCCTGATAG AAGCAAAGAA AGGCTGATAT CTTCTGGCAT       240

TTACTTAAGT CCTTACAGTT TCAGACCCCA CTCACATCCA GTTTGTAAAA CTTTAGAAAA       300
```

-continued

```
TCACATTTTG TACAATGTTT TACCTAGTTA TGTTAATAAT TCATTTTACT TTGTAGGAAT      360

CAAGGATTTT AAGCTGCAGT TCTTGAAAAG GAGGAATAAG GATCTCAGCT TGGTAGCACT      420

CATAAATAGG TTTGTGACAA GTCGTGATGT TAGTAGGTAT GGGTCTGAGT TCGTTATAAG      480

TTCTAGTGAC AAATCAAGTC AGGTTGTCAG TAGAAAGGGC ATTGGTGATT CTAACACACT      540

CCGGAGATTG GTCCCACGTG TAATTTCCAC AGGTGCCAGG AATCTTTTTC TGCATGATGA      600

GATTCACTAC TGGTCAATTA GTGATCTGAT CAATTTTTTG GACGTTGCCA AGCCAAGCAT      660

GCTCTTGGCA ACTGCAGTAA TCCCTCCAGA AGTGCTGGTT GGCTCTCCAG AGAGTCTTAA      720

CCCTTGGGCC TACCAGTATA AAATCAATGG CAACCAACTG CTCTTCGCAC CAGATGGCAA      780

CTGGAATGAG ATGTACTCAC AACCTTTGTC ATGCAGATAC CTGCTCAAGG CCAGATCTGT      840

AGTTCTGCCC GATGGCTCAC GCTACTCGGT TGACATCATT CACTCAAAAT TTAGTCACCA      900

CTTGCTTAGT TTCACCCCTA TGGGTAATCT TTTGACTTCA AACATGCGAT GTTTTTCTGG      960

CTTCGATGCA ATAGGCATAA AAGATCTTGA ACCTCTAAGC CGCGGCATGC ACAGTTGCTT     1020

CCCAGTACAT CATGATGTTG TAACTAAGAT ATATCTTTAT TTGAGAACTC TCAAGAAGCC     1080

AGATAAGGAG TCTGCCGAGG CAAAGCTTCG ACAACTCATA GAAAAACCCA CAGGGAGGGA     1140

GATAAAGTTT ATCGAGGATT TTTCCTCACT AGTAATAAAT TGTGGGAGGA GTGGCTCTTT     1200

GCTTATGCCC AACATTTCTA AGTTGGTCAT ATCATTCTTT TGCCGGATGA TGCCAAATGC     1260

ACTCGCCAGG CTCTCTTCTA GCTTTCGAGA GTGTTCGCTA GATTCATTTG TGTACTCACT     1320

TGAGCCCTTT AATTTTTCCG TTAATTTAGT GGATATAACT CCTGATTTCT TTGAGCATTT     1380

ATTTCTCTTC TCCTGCCTAA ATGAGTTGAT CGAGGAGGAC GTTGAAGAGG TCATGGACAA     1440

TTCTTGGTTT GGACTTGGGG ACTTACAATT CAATCGCCAG AGGGCCCCGT TCTTTCTTGG     1500

GTCTTCATAT TGGCTCAACT CCAAATTTTC AGTTGAGCAC AAGTTTTCAG GCACCATCAA     1560

TTCTCAAATC ATGCAAGTTA TTTTATCTTT GATCCCATTT TCTGATGATC CCACTTTTAG     1620

GCCATCTTCT ACAGAGGTTA ACCTTGCACT ATCAGAGGTT AAGGCTGCGC TAGAAGCTAC     1680

TGGGCAGTCA AAATTGTTCA GGTTTTTGGT GGACGACTGT GCTATGCGTG AGGTTAGAAG     1740

TTCCTATAAG GTGGGCCTTT TTAAGCACAT AAAAGCCCTC ACTCATTGCT TAATTCTTG      1800

TGGCCTCCAA TGGTTCCTCC TTAGGCAAAG GTCCAACCTC AAATTTCTGA AGGACAGGGC     1860

ATCGTCCTTT GCTGATCTTG ATTGTGAGGT TATCAAAGTT TATCAGCTTG TAACATCACA     1920

GGCAATACTT CCTGAGGCTC TGCTTAGCTT GACCAAAGTC TTTGTCAGGG ATTCTGACTC     1980

AAAGGGTGTT TCCATTCCCA GATTGGTCTC GAGAAATGAG CTAGAGGAAC TAGCTCACCC     2040

AGCTAATTCA GCCCTTGAGG AGCCTCAATC AGTTGATTGT AATGCAGGCA GGGTTCAAGC     2100

AAGCGTTTCA AGTTCCCAGC AGCTTGCCGA CACCCACTCT CTTGGTAGCG TTAAGTCATC     2160

AATTGAGACA GCTAACAAGG CTTTTAACTT GGAGGAGCTA AGGATCATGA TTAGAGTCTT     2220

GCCGGAGGAT TTTAACTGGG TGGCGAAGAA CATTGGTTTT AAAGACAGGC TGAGAGGCAG     2280

GGGTGCATCA TTCTTCTCAA AACCAGGAAT TTCATGTCAT AGTTACAATG GTGGGAGCCA     2340

CACAAGCTTA GGGTGGCCAA AGTTCATGGA TCAGATTCTA AGCTCCACTG GTGGACGTAA     2400

TTACTACAAT TCATGCCTGG CTCAGATCTA TGAGGAAAAT TCAAAATTGG CTCTTCATAA     2460

GGATGATGAG AGTTGCTATG AAATTGGGCA CAAAGTTTTG ACTGTTAATT TAATCGGCTC     2520

AGCAACTTTC ACTATTAGTA AGTCGCGAAA TTTGGTTGGG GGTAATCATT GCAGCCTGAC     2580

AATTGGGCCA AATGAGTTTT TCGAAATGCC TAGGGGCATG CAATGCAATT ACTTCCATGG     2640

GGTTTCCAAT TGTACGCCAG GGCGGGTATC GCTGACCTTT AGGCGCCAAA AGTTGGAAGA     2700
```

-continued

```
TGATGATTTG ATCTTCATAA ATCCACAGGT GCCCATTGAG CTCAATCATG AAAAGCTTGA       2760

CCGAAGTATG TGGCAGATGG GCCTTCATGG AATTAAGAAA TCTATTTCTA TGAATGGCAC       2820

GAGTTTTACC TCAGACCTAT GCTCTTGTTT CTCTTGCCAC AACTTTCATA AATTCAAGGA       2880

TCTCATCAAT AACTTGAGAT TGGCCCTAGG AGCACAAGGG CTAGGTCAGT GTGACAGGGT       2940

TGTGTTTGCA ACAACAGGTC CTGGTCTATC TAAGGTTTTA GAAATGCCTC GGAGCAAAAA       3000

GCAATCAATT TTGGTTCTTG AAGGTGCCCT ATCCATAGAA ACAGATTATG GTCCAAAAGT       3060

CCTGGGGTCT TTTGAAGTTT TCAAAGGGGA CTTTCACATT AAGAAGATGG AGGAAGGTTC       3120

AATTTTTGTA ATAACGTACA AGGCCCCAAT TAGATCCACT GGCAGGTTGA GGGTTCACAG       3180

TTCAGAATGC TCATTTTCCG GATCCAAAGA GGTATTGCTA GGCTGCCAGA TTGAGGCATG       3240

TGCTGATTAT GATATTGATG ATTTTAACAC TTTCTCTGTG CCTGGTGATG GCAATTGCTT       3300

TTGGCATTCT GTTGGTTTTT TACTTAGCAC TGATGGACTT GCCCTAAAGG CCGGTATTCG       3360

ATCTTTCGTG GAGAGTGAGC GCTTGGTAAG TCCAGATCTT TCAGCCCCAG CAATTTCTAA       3420

ACAATTGGAA GAGAATGCTT ATGCCGAGAA TGAGATGATC GCATTATTCT GCATTCGGCA       3480

CCACGTAAGG CCTATAGTGA TCACACCAGA ATATGAAGTT AGTTGGAAAT TCGGGAAGG       3540

TGAGTGGCCC CTATGTGGAA TTCTTTGCCT TAAATCAAAT CACTTCCAAC CATGCGCCCC       3600

ACTGAATGGT TGCATGATCA CAGCCATTGC TTCAGCACTT GGAAGGCGTG AAGTTGATGT       3660

GTTAAATTAT CTGTGTAGAC CCAGCACTAA TCATATTTTT GAGGAGCTTT GTCAGGGAGG       3720

GGGCCTTAAC ATGATGTATT TAGCTGAAGC TTTTGAGGCC TTTGACATTT GCGCTAAATG       3780

TGATATAAAT GGAGAGATTG AAGTGATTAA TCCGTGTGGT AAAATTTCTG CATTGTTTGA       3840

CATAACTAAT GAGCACATAA GGCATGTTGA GAAAATAGGT AATGGCCCTC AGAGCATAAA       3900

AGTGGATGAA TTGCGGAAGG TCAAGCGATC CGCCCTCGAT TTCCTTTCAA TGAATGGGTC       3960

TAAAATAACC TACTTCCCAA GCTTTGAGCG GGCTGAAAAG TTGCAAGGAT GTTTGCTAGG       4020

GGGCCTAACT GGCGTTATAA GTGATGAGAA GTTCAGTGAT GCAAAACCTT GGCTTTCTGG       4080

TATATCTACT ACTGATATTA AGCCAAGGGA ATTGACTGTC GTGCTTGGTA CATTTGGGGC       4140

TGGGAAGAGT TTCTTGTACA AGAGTTTCAT GAAAAGGTCT GAGGGTAAAT TCGTAACCTT       4200

TGTTTCTCCC AGACGTGCTT TAGCAAATTC AATCAAAAAT GATCTTGAAA TGGATGATAG       4260

CTGCAAAGTT GCTAAAGCAG GTAGGTCAAA GAAGGAAGGG TGGGATGTAG TAACTTTTGA       4320

GGTTTTCCTT AGAAAAGTTG CAGGATTGAA GGCTGGCCAC TGTGTGATTT TTGATGAGGT       4380

CCAGTTGTTT CCTCCTGGAT ACATCGATCT ATGCTTGCTT ATTATACGTA GTGATGCTTT       4440

CATTTCACTT GCTGGTGATC CATGTCAAAG CACATATGAC TCGCAAAAGG ATCGGGCAAT       4500

TTTGGGCGCT GAGCAGAGTG ACATACTTAG ACTGCTTGAG GGCAAAACGT ATAGGTATAA       4560

CATAGAAAGC AGGAGGTTTG TGAACCCAAT GTTCGAATCA AGACTGCCAT GTCACTTCAA       4620

AAAGGGCTCG ATGACTGCCG CTTTCGCTGA TTATGCAATC TTCCATAATA TGCATGACTT       4680

TCTCCTGGCG AGGTCAAAAG GTCCCTTGGA TGCCGTTTTG GTTTCCAGTT TTGAGGAGAA       4740

AAAGATAGTC CAGTCCTACT TTGGAATGAA ACAGCTCACA CTCACATTTG GTGAATCAAC       4800

TGGGTTGAAT TTCAAAAATG GGGAATTCT CATATCACAT GATTCCTTTC ACACAGATGA       4860

TCGGCGGTGG CTTACTGCTT TATCTCGCTT CAGCCACAAT TTGGATTTGG TGAACATCAC       4920

AGGTCTGAGG GTGAAAGTT TTCTCTCGCA CTTTGCTGGC AAACCCCTCT ACCATTTTTT       4980

AACAGCCAAA AGTGGGGAGA ATGTCATACG AGATTTGCTC CCAGGTGAGC CTAACTTCTT       5040

CAGTGGCTTT AACGTTAGCA TTGGAAAGAA TGAAGGTGTT AGGGAGGAGA AGTTATGTGG       5100
```

```
TGACCCATGG TTAAAAGTTA TGCTTTTCCT GGGTCAAGAT GAGGATTGTG AAGTTGAAGA      5160

GATGGAGTCA GAATGCTCAA ATGAAGAATG GTTTAAAACC CACATCCCCT TGAGTAATCT      5220

GGAGTCAACC AGGGCCAGGT GGGTGGGTAA AATGGCCTTG AAAGAGTATC GGGAGGTGCG      5280

TTGTGGTTAT GAAATGACTC AACAATTCTT TGATGAGCAT AGGGGTGGAA CTGGTGAGCA      5340

ACTGAGCAAT GCATGTGAGA GGTTTGAAAG CATTTACCCA AGGCATAAAG GAAATGATTC      5400

AATAACCTTC CTCATGGCTG TCCGAAAGCG TCTCAAATTT TCGAAGCCCC AGGTTGAAGC      5460

TGCCAAACTG AGGCGGGCCA AACCATATGG GAAATTCTTA TTAGATTCTT TCCTATCCAA      5520

AATCCCATTG AAAGCCAGTC ATAATTCCAT CATGTTTCAT GAAGCGGTAC AGGAGTTTGA      5580

GGCGAAGAAG GCTAGTAAGA GTGCAGCAAC TATAGAGAAT CATGCAGGTA GGTCATGCAG      5640

GGATTGGTTA TTAGATGTTG CTCTGATTTT TATGAAGTCA CAACACTGTA CTAAATTTGA      5700

CAACAGGCTT AGAGTAGCTA AAGCTGGGCA AACCCTTGCT TGCTTCCAAC ATGCTGTTCT      5760

GGTTCGCTTT GCACCCTATA TGAGATACAT TGAGAAAAAG CTAATGCAAG CTCTGAAGCC      5820

TAACTTCTAC ATCCATTCAG GGAAAGGTCT GACGAGCTGA ACGAGTGGGT CAGAACTAGA      5880

GGATTCACTG GAATTTGCAC AGAATCAGAC TACGAAGCCT TTGATGCTTC CCAAGACCAC      5940

TTCATCCTAG CATTCGAATT GCAGATAATG AAATTTTTGG GGTTACCTGA AGATTTAATT      6000

TTGGACTATG AATTCATAAA AATTCATTTG GGATCAAAGC TCGGATCATT CTCTATAATG      6060

AGGTTTACTG GGGAGGCCAG CACATTTCTG TTTAACACTA TGGCTAACAT GTTGTTCACC      6120

TTTCTGAGGT ACGAACTAAC AGGCTCTGAG TCAATAGCAT TTGCAGGTGA TGACATGTGT      6180

GCTAATCGAA GGTTGCGGCT TAAAACAGAG CATGAGGGTT TTCTGAACAT GATTTGCCTT      6240

AAGGCCAAGG TTCAGTTTGT TTCCAATCCC ACATTCTGCG GATGGTGTTT ATTTAAGGAA      6300

GGGATCTTCA AGAAGCCTCA ATTAATCTGG GAGCGGATAT GCATTGCTAG GGAGATGGGC      6360

AACCTGGAGA ATTGTATTGA CAATTATGCG ATAGAGGTCT CCTATGCATA CCGACTGGGA      6420

GAGCTAGCCA TTGAAATGAT GACCGAGGAA GAAGTGGAGG CCCATTATAA TTGTGTTAGA      6480

TTCTTGGTCA GGAACAAGCA TAAGATGAGA TGCTCAATTT CAGGCCTATT TGAAGCTATT      6540

GATTAGGCCT TAAGTATTTG GCATTATTTG AGTATTATGA ATAATTTAGT TAAAGCATTG      6600

TCAGCATTTG AGTTTGTAGG TGTTTTCAGT GTGCTTAAAT TTCCAGTAGT CATTCATAGT      6660

GTGCCTGGTA GTGGTAAAAG TAGTTTAATA AGGGAGCTAA TTTCCGAGGA TGAGAATTTC      6720

ATAGCTTTCA CAGCAGGTGT TCCAGACAGC CCTAATCTCA CAGGAAGGTA CATTAAGCCT      6780

TATTCTCCAG GGTGTGCAGT GCCAGGGAAA GTTAATATAC TTGATGAGTA CTTGTCCGTC      6840

CAAGATTTTT CAGGTTTTGA TGTGCTGTTC TCGGACCCAT ACCAAAACAT CAGCATTCCT      6900

AAAGAGGCAC ATTTCATCAA GTCAAAAACT TGTAGGTTTG GCGTGAATAC TTGCAAATAT      6960

CTTTCCTCCT TCGGTTTTAA GGTTAGCAGT GACGGTTTGG ACAAAGTCAT TGTGGGGTCG      7020

CCTTTTACAC TAGATGTTGA AGGGGTGCTA ATATGCTTTG GTAAGGAGGC AGTGGATCTC      7080

GCTGTTGCGC ACAACTCTGA ATTCAAATTA CCTTGTGAAG TTAGAGGTTC AACTTTTAAC      7140

GTCGTAACTC TTTTGAAATC AAGAGATCCA ACCCCAGAGG ATAGGCACTG GTTTTACATT      7200

GCTGCTACAA GACACAGGGA GAAATTGATA ATCATGCAGT AAGATGCCTT TTCAGCAGCC      7260

TGCGAATTGG GCAAAAACCA TAACTCCATT GACAGTTGGC TTGGGCATTG GCTTGTGCT      7320

GCATTTCTG AGGAAGTCAA ATCTACCTTA TTCAGGGGAC AACATCCATC AATTCCCTCA      7380

CGGTGGGCGT TACAGGGACG GTACAAAAAG TATAACTTAC TGTGGTCCAA AGCAATCCTT      7440

CCCCAGCTCT GGGATATTCG GCCAATCTGA GAATTTTGTG CCCTTAATGC TTGTCATAGG      7500
```

```
-continued
TCTAATCGCA TTCATACATG TATTGTCTGT TTGGAATTCT GGTCTTGGTA GGAATTGTAA      7560

TTGCCATCCA AATCCTTGCT CATGTAGACA GCAGTAGTGG CAACCACCAA GGTTGCTTCA      7620

TTAGGGCCAC TGGAGAGTCA ATTTTGATTG AAAACTGCGG CCCAAGTGAG GCCCTTGCAT      7680

CCACTGTGAA GGAGGTGCTG GGAGGTTTGA AGGCTTTAGG GGTTAGCCGT GCTGTTGAAG      7740

AAATTGATTA TCATTGTTAA ATTGGCTGAA TGGCAAGTCA AATTGGGAAA CTCCCCGGTG      7800

AATCAAATGA GGCTTTTGAA GCCCGGCTAA AATCGCTGGA GTTAGCTAGA GCTCAAAAGC      7860

AGCCGGAAGG TTCTAATGCA CCACCTACTC TCAGTGGCAT TCTTGCCAAA CGCAAGAGGA      7920

TTATAGAGAA TGCACTTTCA AAGACGGTGG ACATGAGGGA GGTTTTGAAA CACGAAACGG      7980

TGGTGATTTC CCCAAATGTC ATGGATGAAG GTGCAATAGA CGAGCTGATT CGTGCATTTG      8040

GTGAATCTGG CATAGCTGAA AGCGTGCAAT TTGATGTGGC CATAGATATA GCACGTCACT      8100

GCTCTGATGT TGGTAGCTCC CAGAGGTCAA CCCTGATTGG CAAGAGTCCA TTTTGTGACC      8160

TAAACAGATC AGAAATAGCT GGGATTATAA GGGAGGTGAC CACATTACGT AGATTTTGCA      8220

TGTACTATGC AAAAATCGTG TGGAACATCC ATCTGGAGAC GGGGATACCA CCAGCTAACT      8280

GGGCCAAGAA AGGATTTAAT GAGAATGAAA AGTTTGCAGC CTTTGATTTT TTCTTGGGAG      8340

TCACAGATGA GAGTGCGCTT GAACCAAAGG GTGGAATTAA AAGAGCTCCA ACGAAAGCTG      8400

AGATGGTTGC TAATATCGCC TCTTTTGAGG TTCAAGTGCT CAGACAAGCT ATGGCTGAAG      8460

GCAAGCGGAG TTCCAACCTT GGAGAGATTA GTGGTGGAAC GGCTGGTGCA CTCATCAACA      8520

ACCCCTTTTC AAATGTTACA CATGAATGAG GATGACGAAG TCAGCGACAA TTCCGCAGTC      8580

CAATAATTCC CCGATTTCAA GGCTGGGTTA AGCCTGTTCG CTGGAATACC GTACTAATAG      8640

TATTCCCTTT CCATGCTAAA TCCTATTTAA TATATAAGGT GTGGAAAGTA AAAGAAGATT      8700

TGGTGTGTTT TTATAGTTTT CATTCAAAAA AAAAAAAAAA AAA                       8743
```

The DNA molecule of SEQ. ID. No. 1 contains at least five open reading frames (e.g., ORF1–ORF5), each of which encodes a particular protein or polypeptide of RSPaV-1, and a 3' untranscribed region downstream of ORF5.

Another DNA molecule of the present invention (RSPaV-1 ORF1) includes nucleotides 62–6547 of SEQ. ID. No. 1. The DNA molecule of RSPaV-1 ORF1 encodes for a RSPaV-1 replicase and comprises a nucleotide sequence corresponding to SEQ. ID. No. 2 as follows:

```
ATGGCCCTCT CTTATAGGCC TGCTGTTGAA GAGGTGCTCG CAAAATTCAC CTCTGATGAA      60

CAATCCAGGG TTTCTGCTAC AGCTCTCAAG GCATTAGTAG ACTTAGAGGA AAGTCAGCAC     120

AATTTGTTCT CTTTCGCATT GCCTGATAGA AGCAAAGAAA GGCTGATATC TTCTGGCATT     180

TACTTAAGTC CTTACAGTTT CAGACCCCAC TCACATCCAG TTTGTAAAAC TTTAGAAAAT     240

CACATTTTGT ACAATGTTTT ACCTAGTTAT GTTAATAATT CATTTTACTT TGTAGGAATC     300

AAGGATTTTA AGCTGCAGTT CTTGAAAAGG AGGAATAAGG ATCTCAGCTT GGTAGCACTC     360

ATAAATAGGT TTGTGACAAG TCGTGATGTT AGTAGGTATG GGTCTGAGTT CGTTATAAGT     420

TCTAGTGACA AATCAAGTCA GGTTGTCAGT AGAAAGGGCA TTGGTGATTC TAACACACTC     480

CGGAGATTGG TCCCACGTGT AATTTCCACA GGTGCCAGGA ATCTTTTTCT GCATGATGAG     540

ATTCACTACT GGTCAATTAG TGATCTGATC AATTTTTTGG ACGTTGCCAA GCCAAGCATG     600

CTCTTGGCAA CTGCAGTAAT CCCTCCAGAA GTGCTGGTTG GCTCTCCAGA GAGTCTTAAC     660

CCTTGGGCCT ACCAGTATAA AATCAATGGC AACCAACTGC TCTTCGCACC AGATGGCAAC     720

TGGAATGAGA TGTACTCACA ACCTTTGTCA TGCAGATACC TGCTCAAGGC CAGATCTGTA     780
```

-continued

```
GTTCTGCCCG ATGGCTCACG CTACTCGGTT GACATCATTC ACTCAAAATT TAGTCACCAC    840
TTGCTTAGTT TCACCCCTAT GGGTAATCTT TTGACTTCAA ACATGCGATG TTTTTCTGGC    900
TTCGATGCAA TAGGCATAAA AGATCTTGAA CCTCTAAGCC GCGGCATGCA CAGTTGCTTC    960
CCAGTACATC ATGATGTTGT AACTAAGATA TATCTTTATT TGAGAACTCT CAAGAAGCCA   1020
GATAAGGAGT CTGCCGAGGC AAAGCTTCGA CAACTCATAG AAAAACCCAC AGGGAGGGAG   1080
ATAAAGTTTA TCGAGGATTT TTCCTCACTA GTAATAAATT GTGGGAGGAG TGGCTCTTTG   1140
CTTATGCCCA ACATTTCTAA GTTGGTCATA TCATTCTTTT GCCGGATGAT GCCAAATGCA   1200
CTCGCCAGGC TCTCTTCTAG CTTTCGAGAG TGTTCGCTAG ATTCATTTGT GTACTCACTT   1260
GAGCCCTTTA ATTTTTCCGT TAATTTAGTG GATATAACTC CTGATTTCTT TGAGCATTTA   1320
TTTCTCTTCT CCTGCCTAAA TGAGTTGATC GAGGAGGACG TTGAAGAGGT CATGGACAAT   1380
TCTTGGTTTG GACTTGGGGA CTTACAATTC AATCGCCAGA GGGCCCCGTT CTTTCTTGGG   1440
TCTTCATATT GGCTCAACTC CAAATTTTCA GTTGAGCACA AGTTTTCAGG CACCATCAAT   1500
TCTCAAATCA TGCAAGTTAT TTTATCTTTG ATCCCATTTT CTGATGATCC CACTTTTAGG   1560
CCATCTTCTA CAGAGGTTAA CCTTGCACTA TCAGAGGTTA AGGCTGCGCT AGAAGCTACT   1620
GGGCAGTCAA AATTGTTCAG GTTTTTGGTG GACGACTGTG CTATGCGTGA GGTTAGAAGT   1680
TCCTATAAGG TGGGCCTTTT TAAGCACATA AAAGCCCTCA CTCATTGCTT TAATTCTTGT   1740
GGCCTCCAAT GGTTCCTCCT TAGGCAAAGG TCCAACCTCA AATTTCTGAA GGACAGGGCA   1800
TCGTCCTTTG CTGATCTTGA TTGTGAGGTT ATCAAAGTTT ATCAGCTTGT AACATCACAG   1860
GCAATACTTC CTGAGGCTCT GCTTAGCTTG ACCAAAGTCT TTGTCAGGGA TTCTGACTCA   1920
AAGGGTGTTT CCATTCCCAG ATTGGTCTCG AGAAATGAGC TAGAGGAACT AGCTCACCCA   1980
GCTAATTCAG CCCTTGAGGA GCCTCAATCA GTTGATTGTA ATGCAGGCAG GGTTCAAGCA   2040
AGCGTTTCAA GTTCCCAGCA GCTTGCCGAC ACCCACTCTC TTGGTAGCGT TAAGTCATCA   2100
ATTGAGACAG CTAACAAGGC TTTTAACTTG GAGGAGCTAA GGATCATGAT TAGAGTCTTG   2160
CCGGAGGATT TTAACTGGGT GGCGAAGAAC ATTGGTTTTA AGACAGGCT GAGAGGCAGG    2220
GGTGCATCAT TCTTCTCAAA ACCAGGAATT TCATGTCATA GTTACAATGG TGGGAGCCAC   2280
ACAAGCTTAG GGTGGCCAAA GTTCATGGAT CAGATTCTAA GCTCCACTGG TGGACGTAAT   2340
TACTACAATT CATGCCTGGC TCAGATCTAT GAGGAAAATT CAAAATTGGC TCTTCATAAG   2400
GATGATGAGA GTTGCTATGA AATTGGGCAC AAAGTTTTGA CTGTTAATTT AATCGGCTCA   2460
GCAACTTTCA CTATTAGTAA GTCGCGAAAT TTGGTTGGGG GTAATCATTG CAGCCTGACA   2520
ATTGGGCCAA ATGAGTTTTT CGAAATGCCT AGGGGCATGC AATGCAATTA CTTCCATGGG   2580
GTTTCCAATT GTACGCCAGG GCGGGTATCG CTGACCTTTA GGCGCCAAAA GTTGGAAGAT   2640
GATGATTTGA TCTTCATAAA TCCACAGGTG CCCATTGAGC TCAATCATGA AAAGCTTGAC   2700
CGAAGTATGT GGCAGATGGG CCTTCATGGA ATTAAGAAAT CTATTTCTAT GAATGGCACG   2760
AGTTTTACCT CAGACCTATG CTCTTGTTTC TCTTGCCACA ACTTTCATAA ATTCAAGGAT   2820
CTCATCAATA ACTTGAGATT GGCCCTAGGA GCACAAGGGC TAGGTCAGTG TGACAGGGTT   2880
GTGTTTGCAA CAACAGGTCC TGGTCTATCT AAGGTTTTAG AAATGCCTCG GAGCAAAAAG   2940
CAATCAATTT TGGTTCTTGA AGGTGCCCTA TCCATAGAAA CAGATTATGG TCCAAAAGTC   3000
CTGGGGTCTT TTGAAGTTTT CAAAGGGGAC TTTCACATTA AGAAGATGGA GGAAGGTTCA   3060
ATTTTTGTAA TAACGTACAA GGCCCCAATT AGATCCACTG GCAGGTTGAG GGTTCACAGT   3120
TCAGAATGCT CATTTTCCGG ATCCAAAGAG GTATTGCTAG GCTGCCAGAT TGAGGCATGT   3180
```

-continued

```
GCTGATTATG ATATTGATGA TTTTAACACT TTCTCTGTGC CTGGTGATGG CAATTGCTTT      3240

TGGCATTCTG TTGGTTTTTT ACTTAGCACT GATGGACTTG CCCTAAAGGC CGGTATTCGA      3300

TCTTTCGTGG AGAGTGAGCG CTTGGTAAGT CCAGATCTTT CAGCCCCAGC AATTTCTAAA      3360

CAATTGGAAG AGAATGCTTA TGCCGAGAAT GAGATGATCG CATTATTCTG CATTCGGCAC      3420

CACGTAAGGC CTATAGTGAT CACACCAGAA TATGAAGTTA GTTGGAAATT CGGGGAAGGT      3480

GAGTGGCCCC TATGTGGAAT TCTTTGCCTT AAATCAAATC ACTTCCAACC ATGCGCCCCA      3540

CTGAATGGTT GCATGATCAC AGCCATTGCT TCAGCACTTG GAAGGCGTGA AGTTGATGTG      3600

TTAAATTATC TGTGTAGACC CAGCACTAAT CATATTTTTG AGGAGCTTTG TCAGGGAGGG      3660

GGCCTTAACA TGATGTATTT AGCTGAAGCT TTTGAGGCCT TTGACATTTG CGCTAAATGT      3720

GATATAAATG GAGAGATTGA AGTGATTAAT CCGTGTGGTA AAATTTCTGC ATTGTTTGAC      3780

ATAACTAATG AGCACATAAG GCATGTTGAG AAAATAGGTA ATGGCCCTCA GAGCATAAAA      3840

GTGGATGAAT TGCGGAAGGT CAAGCGATCC GCCCTCGATT TCCTTTCAAT GAATGGGTCT      3900

AAAATAACCT ACTTCCCAAG CTTTGAGCGG GCTGAAAAGT TGCAAGGATG TTTGCTAGGG      3960

GGCCTAACTG GCGTTATAAG TGATGAGAAG TTCAGTGATG CAAAACCTTG GCTTTCTGGT      4020

ATATCTACTA CTGATATTAA GCCAAGGGAA TTGACTGTCG TGCTTGGTAC ATTTGGGGCT      4080

GGGAAGAGTT TCTTGTACAA GAGTTTCATG AAAAGGTCTG AGGGTAAATT CGTAACCTTT      4140

GTTTCTCCCA GACGTGCTTT AGCAAATTCA ATCAAAAATG ATCTTGAAAT GGATGATAGC      4200

TGCAAAGTTG CTAAAGCAGG TAGGTCAAAG AAGGAAGGGT GGGATGTAGT AACTTTTGAG      4260

GTTTTCCTTA GAAAAGTTGC AGGATTGAAG GCTGGCCACT GTGTGATTTT TGATGAGGTC      4320

CAGTTGTTTC CTCCTGGATA CATCGATCTA TGCTTGCTTA TTATACGTAG TGATGCTTTC      4380

ATTTCACTTG CTGGTGATCC ATGTCAAAGC ACATATGACT CGCAAAAGGA TCGGGCAATT      4440

TTGGGCGCTG AGCAGAGTGA CATACTTAGA CTGCTTGAGG GCAAAACGTA TAGGTATAAC      4500

ATAGAAAGCA GGAGGTTTGT GAACCCAATG TTCGAATCAA GACTGCCATG TCACTTCAAA      4560

AAGGGCTCGA TGACTGCCGC TTTCGCTGAT TATGCAATCT TCCATAATAT GCATGACTTT      4620

CTCCTGGCGA GGTCAAAAGG TCCCTTGGAT GCCGTTTTGG TTTCCAGTTT TGAGGAGAAA      4680

AAGATAGTCC AGTCCTACTT TGGAATGAAA CAGCTCACAC TCACATTTGG TGAATCAACT      4740

GGGTTGAATT TCAAAAATGG GGAATTCTC ATATCACATG ATTCCTTTCA CACAGATGAT      4800

CGGCGGTGGC TTACTGCTTT ATCTCGCTTC AGCCACAATT TGGATTTGGT GAACATCACA      4860

GGTCTGAGGG TGGAAAGTTT TCTCTCGCAC TTTGCTGGCA AACCCCTCTA CCATTTTTTA      4920

ACAGCCAAAA GTGGGAGAA TGTCATACGA GATTTGCTCC CAGGTGAGCC TAACTTCTTC      4980

AGTGGCTTTA ACGTTAGCAT TGGAAAGAAT GAAGGTGTTA GGGAGGAGAA GTTATGTGGT      5040

GACCCATGGT TAAAAGTTAT GCTTTTCCTG GGTCAAGATG AGGATTGTGA AGTTGAAGAG      5100

ATGGAGTCAG AATGCTCAAA TGAAGAATGG TTTAAAACCC ACATCCCCTT GAGTAATCTG      5160

GAGTCAACCA GGGCCAGGTG GGTGGGTAAA ATGGCCTTGA AGAGTATCG GGAGGTGCGT      5220

TGTGGTTATG AAATGACTCA ACAATTCTTT GATGAGCATA GGGGTGGAAC TGGTGAGCAA      5280

CTGAGCAATG CATGTGAGAG GTTTGAAAGC ATTTACCCAA GGCATAAAGG AAATGATTCA      5340

ATAACCTTCC TCATGGCTGT CCGAAAGCGT CTCAAATTTT CGAAGCCCCA GGTTGAAGCT      5400

GCCAAACTGA GGCGGGCCAA ACCATATGGG AAATTCTTAT TAGATTCTTT CCTATCCAAA      5460

ATCCCATTGA AAGCCAGTCA TAATTCCATC ATGTTTCATG AAGCGGTACA GGAGTTTGAG      5520

GCGAAGAAGG CTAGTAAGAG TGCAGCAACT ATAGAGAATC ATGCAGGTAG GTCATGCAGG      5580
```

```
GATTGGTTAT TAGATGTTGC TCTGATTTTT ATGAAGTCAC AACACTGTAC TAAATTTGAC        5640

AACAGGCTTA GAGTAGCTAA AGCTGGGCAA ACCCTTGCTT GCTTCCAACA TGCTGTTCTG        5700

GTTCGCTTTG CACCCTATAT GAGATACATT GAGAAAAAGC TAATGCAAGC TCTGAAGCCT        5760

AACTTCTACA TCCATTCAGG GAAAGGTCTG ACGAGCTGAA CGAGTGGGTC AGAACTAGAG        5820

GATTCACTGG AATTTGCACA GAATCAGACT ACGAAGCCTT TGATGCTTCC CAAGACCACT        5880

TCATCCTAGC ATTCGAATTG CAGATAATGA AATTTTTGGG GTTACCTGAA GATTTAATTT        5940

TGGACTATGA ATTCATAAAA ATTCATTTGG GATCAAAGCT CGGATCATTC TCTATAATGA        6000

GGTTTACTGG GGAGGCCAGC ACATTTCTGT TTAACACTAT GGCTAACATG TTGTTCACCT        6060

TTCTGAGGTA CGAACTAACA GGCTCTGAGT CAATAGCATT TGCAGGTGAT GACATGTGTG        6120

CTAATCGAAG GTTGCGGCTT AAAACAGAGC ATGAGGGTTT TCTGAACATG ATTTGCCTTA        6180

AGGCCAAGGT TCAGTTTGTT TCCAATCCCA CATTCTGCGG ATGGTGTTTA TTTAAGGAAG        6240

GGATCTTCAA GAAGCCTCAA TTAATCTGGG AGCGGATATG CATTGCTAGG GAGATGGGCA        6300

ACCTGGAGAA TTGTATTGAC AATTATGCGA TAGAGGTCTC CTATGCATAC CGACTGGGAG        6360

AGCTAGCCAT TGAAATGATG ACCGAGGAAG AAGTGGAGGC CCATTATAAT TGTGTTAGAT        6420

TCTTGGTCAG GAACAAGCAT AAGATGAGAT GCTCAATTTC AGGCCTATTT GAAGCTATTG        6480

ATTAG                                                                    6485
```

The RSPaV-1 replicase has a deduced amino acid sequence 30 corresponding to SEQ. ID. No. 3 as follows:

```
Met Ala Leu Ser Tyr Arg Pro Ala Val Glu Glu Val Leu Ala Lys Phe
 1               5                   10                  15

Thr Ser Asp Glu Gln Ser Arg Val Ser Ala Thr Ala Leu Lys Ala Leu
                20                  25                  30

Val Asp Leu Glu Glu Ser Gln His Asn Leu Phe Ser Phe Ala Leu Pro
            35                  40                  45

Asp Arg Ser Lys Glu Arg Leu Ile Ser Ser Gly Ile Tyr Leu Ser Pro
        50                  55                  60

Tyr Ser Phe Arg Pro His Ser His Pro Val Cys Lys Thr Leu Glu Asn
65                  70                  75                  80

His Ile Leu Tyr Asn Val Leu Pro Ser Tyr Val Asn Asn Ser Phe Tyr
                85                  90                  95

Phe Val Gly Ile Lys Asp Phe Lys Leu Gln Phe Leu Lys Arg Arg Asn
                100                 105                 110

Lys Asp Leu Ser Leu Val Ala Leu Ile Asn Arg Phe Val Thr Ser Arg
            115                 120                 125

Asp Val Ser Arg Tyr Gly Ser Glu Phe Val Ile Ser Ser Ser Asp Lys
        130                 135                 140

Ser Ser Gln Val Val Ser Arg Lys Gly Ile Gly Asp Ser Asn Thr Leu
145                 150                 155                 160

Arg Arg Leu Val Pro Arg Val Ile Ser Thr Gly Ala Arg Asn Leu Phe
                165                 170                 175

Leu His Asp Glu Ile His Tyr Trp Ser Ile Ser Asp Leu Ile Asn Phe
            180                 185                 190

Leu Asp Val Ala Lys Pro Ser Met Leu Leu Ala Thr Ala Val Ile Pro
        195                 200                 205

Pro Glu Val Leu Val Gly Ser Pro Glu Ser Leu Asn Pro Trp Ala Tyr
```

-continued

```
                210                 215                 220
Gln Tyr Lys Ile Asn Gly Asn Gln Leu Leu Phe Ala Pro Asp Gly Asn
225                 230                 235                 240

Trp Asn Glu Met Tyr Ser Gln Pro Leu Ser Cys Arg Tyr Leu Leu Lys
                245                 250                 255

Ala Arg Ser Val Val Leu Pro Asp Gly Ser Arg Tyr Ser Val Asp Ile
            260                 265                 270

Ile His Ser Lys Phe Ser His His Leu Leu Ser Phe Thr Pro Met Gly
            275                 280                 285

Asn Leu Leu Thr Ser Asn Met Arg Cys Phe Ser Gly Phe Asp Ala Ile
            290                 295                 300

Gly Ile Lys Asp Leu Glu Pro Leu Ser Arg Gly Met His Ser Cys Phe
305                 310                 315                 320

Pro Val His His Asp Val Val Thr Lys Ile Tyr Leu Tyr Leu Arg Thr
                325                 330                 335

Leu Lys Lys Pro Asp Lys Glu Ser Ala Glu Ala Lys Leu Arg Gln Leu
            340                 345                 350

Ile Glu Lys Pro Thr Gly Arg Glu Ile Lys Phe Ile Glu Asp Phe Ser
            355                 360                 365

Ser Leu Val Ile Asn Cys Gly Arg Ser Gly Ser Leu Leu Met Pro Asn
370                 375                 380

Ile Ser Lys Leu Val Ile Ser Phe Phe Cys Arg Met Met Pro Asn Ala
385                 390                 395                 400

Leu Ala Arg Leu Ser Ser Ser Phe Arg Glu Cys Ser Leu Asp Ser Phe
                405                 410                 415

Val Tyr Ser Leu Glu Pro Phe Asn Phe Ser Val Asn Leu Val Asp Ile
            420                 425                 430

Thr Pro Asp Phe Phe Glu His Leu Phe Leu Phe Ser Cys Leu Asn Glu
            435                 440                 445

Leu Ile Glu Glu Asp Val Glu Val Met Asp Asn Ser Trp Phe Gly
450                 455                 460

Leu Gly Asp Leu Gln Phe Asn Arg Gln Arg Ala Pro Phe Phe Leu Gly
465                 470                 475                 480

Ser Ser Tyr Trp Leu Asn Ser Lys Phe Ser Val Glu His Lys Phe Ser
                485                 490                 495

Gly Thr Ile Asn Ser Gln Ile Met Gln Val Ile Leu Ser Leu Ile Pro
            500                 505                 510

Phe Ser Asp Asp Pro Thr Phe Arg Pro Ser Ser Thr Glu Val Asn Leu
            515                 520                 525

Ala Leu Ser Glu Val Lys Ala Ala Leu Glu Ala Thr Gly Gln Ser Lys
            530                 535                 540

Leu Phe Arg Phe Leu Val Asp Asp Cys Ala Met Arg Glu Val Arg Ser
545                 550                 555                 560

Ser Tyr Lys Val Gly Leu Phe Lys His Ile Lys Ala Leu Thr His Cys
                565                 570                 575

Phe Asn Ser Cys Gly Leu Gln Trp Phe Leu Leu Arg Gln Arg Ser Asn
            580                 585                 590

Leu Lys Phe Leu Lys Asp Arg Ala Ser Ser Phe Ala Asp Leu Asp Cys
            595                 600                 605

Glu Val Ile Lys Val Tyr Gln Leu Val Thr Ser Gln Ala Ile Leu Pro
            610                 615                 620

Glu Ala Leu Leu Ser Leu Thr Lys Val Phe Val Arg Asp Ser Asp Ser
625                 630                 635                 640
```

-continued

```
Lys Gly Val Ser Ile Pro Arg Leu Val Ser Arg Asn Glu Leu Glu Glu
            645                 650                 655

Leu Ala His Pro Ala Asn Ser Ala Leu Glu Glu Pro Gln Ser Val Asp
                660                 665                 670

Cys Asn Ala Gly Arg Val Gln Ala Ser Val Ser Ser Gln Gln Leu
                675                 680             685

Ala Asp Thr His Ser Leu Gly Ser Val Lys Ser Ser Ile Glu Thr Ala
        690                 695                 700

Asn Lys Ala Phe Asn Leu Glu Glu Leu Arg Ile Met Ile Arg Val Leu
705                 710                 715                 720

Pro Glu Asp Phe Asn Trp Val Ala Lys Asn Ile Gly Phe Lys Asp Arg
                    725                 730                 735

Leu Arg Gly Arg Gly Ala Ser Phe Phe Ser Lys Pro Gly Ile Ser Cys
                740                 745                 750

His Ser Tyr Asn Gly Gly Ser His Thr Ser Leu Gly Trp Pro Lys Phe
            755                 760                 765

Met Asp Gln Ile Leu Ser Ser Thr Gly Gly Arg Asn Tyr Tyr Asn Ser
    770                 775                 780

Cys Leu Ala Gln Ile Tyr Glu Glu Asn Ser Lys Leu Ala Leu His Lys
785                 790                 795                 800

Asp Asp Glu Ser Cys Tyr Glu Ile Gly His Lys Val Leu Thr Val Asn
                805                 810                 815

Leu Ile Gly Ser Ala Thr Phe Thr Ile Ser Lys Ser Arg Asn Leu Val
                820                 825                 830

Gly Gly Asn His Cys Ser Leu Thr Ile Gly Pro Asn Glu Phe Phe Glu
            835                 840                 845

Met Pro Arg Gly Met Gln Cys Asn Tyr Phe His Gly Val Ser Asn Cys
    850                 855                 860

Thr Pro Gly Arg Val Ser Leu Thr Phe Arg Arg Gln Lys Leu Glu Asp
865                 870                 875                 880

Asp Asp Leu Ile Phe Ile Asn Pro Gln Val Pro Ile Glu Leu Asn His
                885                 890                 895

Glu Lys Leu Asp Arg Ser Met Trp Gln Met Gly Leu His Gly Ile Lys
                900                 905                 910

Lys Ser Ile Ser Met Asn Gly Thr Ser Phe Thr Ser Asp Leu Cys Ser
            915                 920                 925

Cys Phe Ser Cys His Asn Phe His Lys Phe Lys Asp Leu Ile Asn Asn
    930                 935                 940

Leu Arg Leu Ala Leu Gly Ala Gln Gly Leu Gly Gln Cys Asp Arg Val
945                 950                 955                 960

Val Phe Ala Thr Thr Gly Pro Gly Leu Ser Lys Val Leu Glu Met Pro
                965                 970                 975

Arg Ser Lys Lys Gln Ser Ile Leu Val Leu Glu Gly Ala Leu Ser Ile
                980                 985                 990

Glu Thr Asp Tyr Gly Pro Lys Val Leu Gly Ser Phe Glu Val Phe Lys
        995                 1000                1005

Gly Asp Phe His Ile Lys Lys Met Glu Glu Gly Ser Ile Phe Val Ile
    1010                1015                1020

Thr Tyr Lys Ala Pro Ile Arg Ser Thr Gly Arg Leu Arg Val His Ser
1025                1030                1035                1040

Ser Glu Cys Ser Phe Ser Gly Ser Lys Glu Val Leu Leu Gly Cys Gln
                1045                1050                1055

Ile Glu Ala Cys Ala Asp Tyr Asp Ile Asp Asp Phe Asn Thr Phe Ser
                1060                1065                1070
```

-continued

```
Val Pro Gly Asp Gly Asn Cys Phe Trp His Ser Val Gly Phe Leu Leu
        1075                1080                1085

Ser Thr Asp Gly Leu Ala Leu Lys Ala Gly Ile Arg Ser Phe Val Glu
        1090                1095                1100

Ser Glu Arg Leu Val Ser Pro Asp Leu Ser Ala Pro Ala Ile Ser Lys
1105                1110                1115                1120

Gln Leu Glu Glu Asn Ala Tyr Ala Glu Asn Glu Met Ile Ala Leu Phe
                1125                1130                1135

Cys Ile Arg His His Val Arg Pro Ile Val Ile Thr Pro Glu Tyr Glu
            1140                1145                1150

Val Ser Trp Lys Phe Gly Glu Gly Glu Trp Pro Leu Cys Gly Ile Leu
            1155                1160                1165

Cys Leu Lys Ser Asn His Phe Gln Pro Cys Ala Pro Leu Asn Gly Cys
        1170                1175                1180

Met Ile Thr Ala Ile Ala Ser Ala Leu Gly Arg Arg Glu Val Asp Val
1185                1190                1195                1200

Leu Asn Tyr Leu Cys Arg Pro Ser Thr Asn His Ile Phe Glu Glu Leu
            1205                1210                1215

Cys Gln Gly Gly Gly Leu Asn Met Met Tyr Leu Ala Glu Ala Phe Glu
            1220                1225                1230

Ala Phe Asp Ile Cys Ala Lys Cys Asp Ile Asn Gly Glu Ile Glu Val
        1235                1240                1245

Ile Asn Pro Cys Gly Lys Ile Ser Ala Leu Phe Asp Ile Thr Asn Glu
        1250                1255                1260

His Ile Arg His Val Glu Lys Ile Gly Asn Gly Pro Gln Ser Ile Lys
1265                1270                1275                1280

Val Asp Glu Leu Arg Lys Val Lys Arg Ser Ala Leu Asp Phe Leu Ser
                1285                1290                1295

Met Asn Gly Ser Lys Ile Thr Tyr Phe Pro Ser Phe Glu Arg Ala Glu
            1300                1305                1310

Lys Leu Gln Gly Cys Leu Leu Gly Gly Leu Thr Gly Val Ile Ser Asp
            1315                1320                1325

Glu Lys Phe Ser Asp Ala Lys Pro Trp Leu Ser Gly Ile Ser Thr Thr
        1330                1335                1340

Asp Ile Lys Pro Arg Glu Leu Thr Val Val Leu Gly Thr Phe Gly Ala
1345                1350                1355                1360

Gly Lys Ser Phe Leu Tyr Lys Ser Phe Met Lys Arg Ser Glu Gly Lys
                1365                1370                1375

Phe Val Thr Phe Val Ser Pro Arg Arg Ala Leu Ala Asn Ser Ile Lys
            1380                1385                1390

Asn Asp Leu Glu Met Asp Asp Ser Cys Lys Val Ala Lys Ala Gly Arg
        1395                1400                1405

Ser Lys Lys Glu Gly Trp Asp Val Val Thr Phe Glu Val Phe Leu Arg
        1410                1415                1420

Lys Val Ala Gly Leu Lys Ala Gly His Cys Val Ile Phe Asp Glu Val
1425                1430                1435                1440

Gln Leu Phe Pro Pro Gly Tyr Ile Asp Leu Cys Leu Leu Ile Ile Arg
                1445                1450                1455

Ser Asp Ala Phe Ile Ser Leu Ala Gly Asp Pro Cys Gln Ser Thr Tyr
            1460                1465                1470

Asp Ser Gln Lys Asp Arg Ala Ile Leu Gly Ala Glu Gln Ser Asp Ile
        1475                1480                1485

Leu Arg Leu Leu Glu Gly Lys Thr Tyr Arg Tyr Asn Ile Glu Ser Arg
```

-continued

```
                1490                1495                1500
Arg Phe Val Asn Pro Met Phe Glu Ser Arg Leu Pro Cys His Phe Lys
1505                1510                1515                1520

Lys Gly Ser Met Thr Ala Ala Phe Ala Asp Tyr Ala Ile Phe His Asn
                1525                1530                1535

Met His Asp Phe Leu Leu Ala Arg Ser Lys Gly Pro Leu Asp Ala Val
                1540                1545                1550

Leu Val Ser Ser Phe Glu Glu Lys Lys Ile Val Gln Ser Tyr Phe Gly
                1555                1560                1565

Met Lys Gln Leu Thr Leu Thr Phe Gly Glu Ser Thr Gly Leu Asn Phe
            1570                1575                1580

Lys Asn Gly Gly Ile Leu Ile Ser His Asp Ser Phe His Thr Asp Asp
1585                1590                1595                1600

Arg Arg Trp Leu Thr Ala Leu Ser Arg Phe Ser His Asn Leu Asp Leu
                1605                1610                1615

Val Asn Ile Thr Gly Leu Arg Val Glu Ser Phe Leu Ser His Phe Ala
                1620                1625                1630

Gly Lys Pro Leu Tyr His Phe Leu Thr Ala Lys Ser Gly Glu Asn Val
                1635                1640                1645

Ile Arg Asp Leu Leu Pro Gly Glu Pro Asn Phe Phe Ser Gly Phe Asn
                1650                1655                1660

Val Ser Ile Gly Lys Asn Glu Gly Val Arg Glu Lys Leu Cys Gly
1665                1670                1675                1680

Asp Pro Trp Leu Lys Val Met Leu Phe Leu Gly Gln Asp Glu Asp Cys
                1685                1690                1695

Glu Val Glu Glu Met Glu Ser Glu Cys Ser Asn Glu Glu Trp Phe Lys
                1700                1705                1710

Thr His Ile Pro Leu Ser Asn Leu Glu Ser Thr Arg Ala Arg Trp Val
                1715                1720                1725

Gly Lys Met Ala Leu Lys Glu Tyr Arg Glu Val Arg Cys Gly Tyr Glu
                1730                1735                1740

Met Thr Gln Gln Phe Phe Asp Glu His Arg Gly Gly Thr Gly Glu Gln
1745                1750                1755                1760

Leu Ser Asn Ala Cys Glu Arg Phe Glu Ser Ile Tyr Pro Arg His Lys
                1765                1770                1775

Gly Asn Asp Ser Ile Thr Phe Leu Met Ala Val Arg Lys Arg Leu Lys
                1780                1785                1790

Phe Ser Lys Pro Gln Val Glu Ala Ala Lys Leu Arg Arg Ala Lys Pro
                1795                1800                1805

Tyr Gly Lys Phe Leu Leu Asp Ser Phe Leu Ser Lys Ile Pro Leu Lys
                1810                1815                1820

Ala Ser His Asn Ser Ile Met Phe His Glu Ala Val Gln Glu Phe Glu
1825                1830                1835                1840

Ala Lys Lys Ala Ser Lys Ser Ala Ala Thr Ile Glu Asn His Ala Gly
                1845                1850                1855

Arg Ser Cys Arg Asp Trp Leu Leu Asp Val Ala Leu Ile Phe Met Lys
                1860                1865                1870

Ser Gln His Cys Thr Lys Phe Asp Asn Arg Leu Arg Val Ala Lys Ala
                1875                1860                1885

Gly Gln Thr Leu Ala Cys Phe Gln His Ala Val Leu Val Arg Phe Ala
                1890                1895                1900

Pro Tyr Met Arg Tyr Ile Glu Lys Lys Leu Met Gln Ala Leu Lys Pro
1905                1910                1915                1920
```

```
                        -continued
Asn Phe Tyr Ile His Ser Gly Lys Gly Leu Asp Glu Leu Asn Glu Trp
                1925            1930            1935

Val Arg Thr Arg Gly Phe Thr Gly Ile Cys Thr Glu Ser Asp Tyr Glu
                1940            1945            1950

Ala Phe Asp Ala Ser Gln Asp His Phe Ile Leu Ala Phe Glu Leu Gln
                1955            1960            1965

Ile Met Lys Phe Leu Gly Leu Pro Glu Asp Leu Ile Leu Asp Tyr Glu
    1970            1975            1980

Phe Ile Lys Ile His Leu Gly Ser Lys Leu Gly Ser Phe Ser Ile Met
1985            1990            1995            2000

Arg Phe Thr Gly Glu Ala Ser Thr Phe Leu Phe Asn Thr Met Ala Asn
                2005            2010            2015

Met Leu Phe Thr Phe Leu Arg Tyr Glu Leu Thr Gly Ser Glu Ser Ile
            2020            2025            2030

Ala Phe Ala Gly Asp Asp Met Cys Ala Asn Arg Arg Leu Arg Leu Lys
            2035            2040            2045

Thr Glu His Glu Gly Phe Leu Asn Met Ile Cys Leu Lys Ala Lys Val
    2050            2055            2060

Gln Phe Val Ser Asn Pro Thr Phe Cys Gly Trp Cys Leu Phe Lys Glu
2065            2070            2075            2080

Gly Ile Phe Lys Lys Pro Gln Leu Ile Trp Glu Arg Ile Cys Ile Ala
            2085            2090            2095

Arg Glu Met Gly Asn Leu Glu Asn Cys Ile Asp Asn Tyr Ala Ile Glu
            2100            2105            2110

Val Ser Tyr Ala Tyr Arg Leu Gly Glu Leu Ala Ile Glu Met Met Thr
            2115            2120            2125

Glu Glu Glu Val Glu Ala His Tyr Asn Cys Val Arg Phe Leu Val Arg
    2130            2135            2140

Asn Lys His Lys Met Arg Cys Ser Ile Ser Gly Leu Phe Glu Ala Ile
2145            2150            2155            2160

Asp
```

The replicase of SEQ. ID. No.3 has a molecular weight of about 240 to 246 kDa, preferably about 244 kDa.

Another DNA molecule of the present invention (RSPaV-1 ORF2) includes nucleotides 6578–7243 of SEQ. ID. No. 1. The DNA molecule of RSPaV-1 ORF2 encodes for a first protein or polypeptide of an RSPaV-1 triple gene block and comprises a nucleotide sequence corresponding to SEQ. ID. No. 4 as follows:

```
ATGAATAATT TAGTTAAAGC ATTGTCAGCA TTTGAGTTTG TAGGTGTTTT CAGTGTGCTT    60
AAATTTCCAG TAGTCATTCA TAGTGTGCCT GGTAGTGGTA AAAGTAGTTT AATAAGGGAG   120
CTAATTTCCG AGGATGAGAA TTTCATAGCT TTCACAGCAG GTGTTCCAGA CAGCCCTAAT   180
CTCACAGGAA GGTACATTAA GCCTTATTCT CCAGGGTGTG CAGTGCCAGG GAAAGTTAAT   240
ATACTTGATG AGTACTTGTC CGTCCAAGAT TTTTCAGGTT TTGATGTGCT GTTCTCGGAC   300
CCATACCAAA ACATCAGCAT TCCTAAAGAG GCACATTTCA TCAAGTCAAA AACTTGTAGG   360
TTTGGCGTGA ATACTTGCAA ATATCTTTCC TCCTTCGGTT TTAAGGTTAG CAGTGACGGT   420
TTGGACAAAG TCATTGTGGG GTCGCCTTTT ACACTAGATG TTGAAGGGGT GCTAATATGC   480
TTTGGTAAGG AGGCAGTGGA TCTCGCTGTT GCGCACAACT CTGAATTCAA ATTACCTTGT   540
GAAGTTAGAG GTTCAACTTT TAACGTCGTA ACTCTTTTGA AATCAAGAGA TCCAACCCCA   600
GAGGATAGGC ACTGGTTTTA CATTGCTGCT ACAAGACACA GGGAGAAATT GATAATCATG   660
CAG                                                                 663
```

The first protein or polypeptide of the RSPaV-1 triple gene block has a deduced amino acid sequence corresponding to SEQ. ID. No. 5 as follows:

The second protein or polypeptide of the RSPaV-1 triple gene block has a deduced amino acid sequence corresponding to SEQ. ID. No. 7 as follows:

```
Met Asn Asn Leu Val Lys Ala Leu Ser Ala Phe Glu Phe Val Gly Val
1               5                   10                  15

Phe Ser Val Leu Lys Phe Pro Val Val Ile His Ser Val Pro Gly Ser
            20                  25                  30

Gly Lys Ser Ser Leu Ile Arg Glu Leu Ile Ser Glu Asp Glu Asn Phe
            35                  40                  45

Ile Ala Phe Thr Ala Gly Val Pro Asp Ser Pro Asn Leu Thr Gly Arg
        50              55                  60

Tyr Ile Lys Pro Tyr Ser Pro Gly Cys Ala Val Pro Gly Lys Val Asn
65                  70                  75                  80

Ile Leu Asp Glu Tyr Leu Ser Val Gln Asp Phe Ser Gly Phe Asp Val
                85                  90                  95

Leu Phe Ser Asp Pro Tyr Gln Asn Ile Ser Ile Pro Lys Glu Ala His
                100                 105                 110

Phe Ile Lys Ser Lys Thr Cys Arg Phe Gly Val Asn Thr Cys Lys Tyr
            115                 120                 125

Leu Ser Ser Phe Gly Phe Lys Val Ser Ser Asp Gly Leu Asp Lys Val
        130                 135                 140

Ile Val Gly Ser Pro Phe Thr Leu Asp Val Glu Gly Val Leu Ile Cys
145                 150                 155                 160

Phe Gly Lys Glu Ala Val Asp Leu Ala Val Ala His Asn Ser Glu Phe
                165                 170                 175

Lys Leu Pro Cys Glu Val Arg Gly Ser Thr Phe Asn Val Val Thr Leu
                180                 185                 190

Leu Lys Ser Arg Asp Pro Thr Pro Glu Asp Arg His Trp Phe Tyr Ile
            195                 200                 205

Ala Ala Thr Arg His Arg Glu Lys Leu Ile Ile Met Gln
            210                 215                 220
```

The first protein or polypeptide of the RSPaV-1 triple gene block has a molecular weight of about 20 to 26 kDa, preferably 24.4 kDa.

Another DNA molecule of the present invention (RSPaV-1 ORF3) includes nucleotides 7245–7598 of SEQ. ID. No. 1. The DNA molecule of RSPaV-1 ORF3 encodes for a second protein or polypeptide of the triple gene block and comprises a nucleotide sequence corresponding to SEQ. ID. No. 6 as follows:

```
ATGCCTTTTC AGCAGCCTGC GAATTGGGCA AAAACCATAA CTCCATTGAC AGTTGGCTTG    60
GGCATTGCGC TTGTGCTGCA TTTTCTCAGG AAGTCAAATC TACCTTATTC AGGGGACAAC   120
ATCCATCAAT TCCCTCACGG TGGGCGTTAC AGGGACGGTA CAAAAAGTAT AACTTACTGT   180
GGTCCAAAGC AATCCTTCCC CAGCTCTGGG ATATTCGGCC AATCTGAGAA TTTTGTGCCC   240
TTAATGCTTG TCATAGGTCT AATCGCATTC ATACATGTAT TGTCTGTTTG GAATTCTGGT   300
CTTGGTAGGA ATTGTAATTG CCATCCAAAT CCTTGCTCAT GTAGACAGCA G            351
```

```
Met Pro Phe Gln Gln Pro Ala Asn Trp Ala Lys Thr Ile Thr Pro Leu
1               5                   10                  15

Thr Val Gly Leu Gly Ile Gly Leu Val Leu His Phe Leu Arg Lys Ser
            20                  25                  30

Asn Leu Pro Tyr Ser Gly Asp Asn Ile His Gln Phe Pro His Gly Gly
            35                  40                  45

Arg Tyr Arg Asp Gly Thr Lys Ser Ile Thr Tyr Cys Gly Pro Lys Gln
    50                  55                  60

Ser Phe Pro Ser Ser Gly Ile Phe Gly Gln Ser Glu Asn Phe Val Pro
65                  70                  75                  80

Leu Met Leu Val Ile Gly Leu Ile Ala Phe Ile His Val Leu Ser Val
                85                  90                  95

Trp Asn Ser Gly Leu Gly Arg Asn Cys Asn Cys His Pro Asn Pro Cys
            100                 105                 110

Ser Cys Arg Gln Gln
            115
```

The second protein or polypeptide of the RSPaV-1 triple gene block has a molecular weight of about 10 to 15 kDa, preferably 12.8 kDa.

Yet another DNA molecule of the present invention (RSPaV-1 ORF4) includes nucleotides 7519–7761 of SEQ. ID. No. 1. The DNA molecule of RSPaV-1 ORF4 encodes for a third protein or polypeptide of the RSPaV-1 triple gene block and comprises a nucleotide sequence corresponding to SEQ. ID. No. 8 as follows:

```
ATGTATTGTC TGTTTGGAAT TCTGGTCTTG GTAGGAATTG TAATTGCCAT CCAAATCCTT   60

GCTCATGTAG ACAGCAGTAG TGGCAACCAC CAAGGTTGCT TCATTAGGGC CACTGGAGAG  120

TCAATTTTGA TTGAAAACTG CCGCCCAACT CAGGCCCTTG CATCCACTGT GAAGGAGGTG  180

CTGGGAGGTT TGAAGGCTTT AGGGGTTAGC CGTGCTGTTG AAGAAATTGA TTATCATTGT  240
```

The third protein or polypeptide of the RSPaV-1 triple gene block has a deduced amino acid sequence corresponding to SEQ. ID. No. 9 as follows:

```
Met Tyr Cys Leu Phe Gly Ile Leu Val Leu Val Gly Ile Val Ile Ala
1               5                   10                  15

Ile Gln Ile Leu Ala His Val Asp Ser Ser Ser Gly Asn His Gln Gly
            20                  25                  30

Cys Phe Ile Arg Ala Thr Gly Glu Ser Ile Leu Ile Glu Asn Cys Gly
            35                  40                  45

Pro Ser Glu Ala Leu Ala Ser Thr Val Lys Glu Val Leu Gly Gly Leu
    50                  55                  60

Lys Ala Leu Gly Val Ser Arg Ala Val Glu Glu Ile Asp Tyr His Cys
65                  70                  75                  80
```

The third protein or polypeptide of the RSPaV-1 triple gene block has a molecular weight of about 5 to 10 kDa, preferably 8.4 kDa.

Still another DNA molecule of the present invention (RSPaV-1 ORF5) includes nucleotides 7771–8550 of SEQ. ID. No. 1. The DNA molecule of RSPaV-1 ORF5 encodes for a RSPaV-1 coat protein and comprises a nucleotide sequence corresponding to SEQ. ID. No. 10 as follows:

```
ATGGCAAGTC AAATTGGGAA ACTCCCCGGT GAATCAAATG AGGCTTTTGA AGCCCGGCTA    60
AAATCGCTGG AGTTAGCTAG AGCTCAAAAG CAGCCGGAAG GTTCTAATGC ACCACCTACT   120
CTCAGTGGCA TTCTTGCCAA ACGCAAGAGG ATTATAGAGA ATGCACTTTC AAAGACGGTG   180
GACATGAGGG AGGTTTTGAA ACACGAAACG GTGGTGATTT CCCCAAATGT CATGGATGAA   240
GGTGCAATAG ACGAGCTGAT TCGTGCATTT GGTGAATCTG GCATAGCTGA AAGCGTGCAA   300
TTTGATGTGG CCATAGATAT AGCACGTCAC TGCTCTGATG TTGGTAGCTC CCAGAGTTCA   360
ACCCTGATTG GCAAGAGTCC ATTTTGTGAC CTAAACAGAT CAGAAATAGC TGGGATTATA   420
AGGGAGGTGA CCACATTACG TAGATTTTGC ATGTACTATG CAAAAATCGT GTGGAACATC   480
CATCTGGAGA CGGGGATACC ACCAGCTAAC TGGGCCAAGA AAGGATTTAA TGAGAATGAA   540
AAGTTTGCAG CCTTTGATTT TTTCTTGGGA GTCACAGATG AGAGTGCGCT TGAACCAAAG   600
GGTGGAATTA AAAGAGCTCC AACGAAAGCT GAGATGGTTG CTAATATCGC CTCTTTTGAG   660
GTTCAAGTGC TCAGACAAGC TATGGCTGAA GGCAAGCGGA GTTCCAACCT TGGAGAGATT   720
AGTGGTGGAA CGGCTGGTGC ACTCATCAAC AACCCCTTTT CAAATGTTAC ACATGAA     777
```

The RSPaV-1 coat protein has a deduced amino acid sequence corresponding to SEQ. ID. No. 11 as follows:

```
Met Ala Ser Gln Ile Gly Lys Leu Pro Gly Glu Ser Asn Glu Ala Phe
 1               5                  10                  15
Glu Ala Arg Leu Lys Ser Leu Glu Leu Ala Arg Ala Gln Lys Gln Pro
                20                  25                  30
Glu Gly Ser Asn Ala Pro Pro Thr Leu Ser Gly Ile Leu Ala Lys Arg
                35                  40                  45
Lys Arg Ile Ile Glu Asn Ala Leu Ser Lys Thr Val Asp Met Arg Glu
        50                  55                  60
Val Leu Lys His Glu Thr Val Val Ile Ser Pro Asn Val Met Asp Glu
65                  70                  75                  80
Gly Ala Ile Asp Glu Leu Ile Arg Ala Phe Gly Glu Ser Gly Ile Ala
                85                  90                  95
Glu Ser Val Gln Phe Asp Val Ala Ile Asp Ile Ala Arg His Cys Ser
                100                 105                 110
Asp Val Gly Ser Ser Gln Ser Ser Thr Leu Ile Gly Lys Ser Pro Phe
                115                 120                 125
Cys Asp Leu Asn Arg Ser Glu Ile Ala Gly Ile Ile Arg Glu Val Thr
        130                 135                 140
Thr Leu Arg Arg Phe Cys Met Tyr Tyr Ala Lys Ile Val Trp Asn Ile
145                 150                 155                 160
His Leu Glu Thr Gly Ile Pro Pro Ala Asn Trp Ala Lys Lys Gly Phe
                165                 170                 175
Asn Glu Asn Glu Lys Phe Ala Ala Phe Asp Phe Leu Gly Val Thr
                180                 185                 190
Asp Glu Ser Ala Leu Glu Pro Lys Gly Gly Ile Lys Arg Ala Pro Thr
                195                 200                 205
Lys Ala Glu Met Val Ala Asn Ile Ala Ser Phe Glu Val Gln Val Leu
        210                 215                 220
Arg Gln Ala Met Ala Glu Gly Lys Arg Ser Ser Asn Leu Gly Glu Ile
225                 230                 235                 240
Ser Gly Gly Thr Ala Gly Ala Leu Ile Asn Asn Pro Phe Ser Asn Val
```

Thr His Glu

The RSPaV-1 coat protein has a molecular weight of about 25 to 30 kDa, preferably 28 kDa.

The DNA molecule which constitutes the substantial portion of the RSPaV strain RSP47-4 genome comprises the nucleotide sequence corresponding to SEQ. ID. No. 12 as follows:

```
GGCTGGGCAA ACTTTGGCCT GCTTTCAACA CGCCGTCTTG GTTCGCTTTG CACCCTACAT     60
GCGATACATT GAAAAGAAGC TTGTGCAGGC ATTGAAACCA AATTTCTACA TTCATTCTGG    120
CAAAGGTCTT GATGAGCTAA GTGAATGGGT TAGAGCCAGA GGTTTCACAG GTGTGTGTAC    180
TGAGTCAGAC TATGAAGCTT TTGATGCATC CCAAGATCAT TTCATCCTGG CATTTGAACT    240
GCAAATCATG AGATTTTTAG GACTGCCAGA AGATCTGATT TTAGATTATG AGTTCATCAA    300
AATTCATCTT GGGTCAAAGC TTGGCTCTTT TGCAATTATG AGATTCACAG GTGAGGCAAG    360
CACCTTCCTA TTCAATACTA TGGCCAACAT GCTATTCACT TTCCTGAGGT ATGAGTTGAC    420
AGGTTCTGAA TCAATTGCAT TTGCTGGAGA TGATATGTGT GCTAATCGCA GGTTAAGACT    480
CAAGACTGAG CACGCCGGCT TTCTAAACAT GATCTGTCTC AAAGCTAAGG TGCAGTTTGT    540
CACAAATCCC ACCTTCTGTG GATGGTGTTT GTTTAAAGAG GGAATCTTTA AAAAACCCCA    600
GCTCATTTGG GAAAGGATCT GCATTGCTAG GGAAATGGGT AACTTGGACA ATTGCATTGA    660
CAATTACGCA ATTGAGGTGT CTTATGCTTA CAGACTTGGG GAATTGTCCA TAGGCGTGAT    720
GACTGAGGAG GAAGTTGAAG CACATTCTAA CTGCGTGCGT TTCCTGGTTC GCAATAAGCA    780
CAAGATGAGG TGCTCAATTT CTGGTTTGTT TGAAGTAATT GTTTAGGCCT TAAGTGTTTG    840
GCATGGTGTG AGTATTATGA ATAACTTAGT CAAAGCTTTG TCTGCTTTTG AATTTGTTGG    900
TGTGTTTTGT GTACTTAAAT TTCCAGTTGT TGTTCACAGT GTTCCAGGTA GCGGTAAAAG    960
TAGCCTAATA AGGGAGCTCA TTTCTGAAGA CGAGGCTTTT GTGGCCTTTA CAGCAGGTGT   1020
GCCAGACAGT CCAAATCTGA CAGGGAGGTA CATCAAGCCC TACGCTCCAG GGTGTGCAGT   1080
GCAAGGGAAA ATAAACATAC TTGATGAGTA CTTGTCTGTC TCTGATACTT CTGGCTTTGA   1140
TGTGCTGTTC TCAGACCCTT ACCAGAATGT CAGCATTCCA AGGGAGGCAC ACTTCATAAA   1200
AACCAAAACC TGTAGGTTTG GTACCAACAC CTGCAAGTAC CTTCAATCTT TTGGCTTTAA   1260
TGTTTGTAGT GATGGGGTGG ATAAAGTTGT TGTAGGGTCG CCATTTGAAC TGGAGGTTGA   1320
GGGGGTTCTC ATTTGCTTTG GAAACGAGGC TGTAGATCTA GCAGTTGCAC ACAATTCTGA   1380
CTTCAAGTTG CCCTGCGAGG TGCGGGGTTC AACATTTGAC GTTGTAACGT TATTGAAGTC   1440
CAGGGATCCA ACTTCAGAAG ATAAGCATTG GTTCTACGTT GCAGCCACAA GGCATCGAAG   1500
TAAACTGATA ATAATGCAGT AAAATGCCTT TTCAGCAACC TGCCAACTGG GCTAAGACCA   1560
TAACTCCATT AACTATTGGT TTGGGCATTG GGTTGGTTCT GCACTTCTTA AGGAAATCAA   1620
ATCTGCCATA TTCAGGAGAC AATATTCACC AGTTCCCACA CGGAGGGCAT TACAGGGACG   1680
GCACGAAGAG TATAACCTAT TGTGGCCCTA GGCAGTCATT CCCAAGCTCA GGAATATTCG   1740
GTCAGTCTGA AAATTTCGTA CCTCTAATAT TGGTCGTGAC TCTGGTCGCT TTTATACATG   1800
CGTTATCTCT TTGGAATTCT GGTCCTAGTA GGAGTTGCAA TTGCCATCCA AATCCTTGCA   1860
CATGTAGACA GCAGTAGTGG CAACCATCAA GGCTGTTTCA TAAGAGCCAC CGGGGAGTCA   1920
ATAGTAATTG AGAATTGTGG GCCGAGCGAG GCCCTAGCTG CTACAGTCAA AGAGGTGTTG   1980
```

```
                             -continued
GGCGGTCTAA AGGCTTTAGG GGTTAGCCAA AAGGTTGATG AAATTAATTA CAGTTGTTGA    2040

GACAGTTGAA TGGCAAGTCA AGTTGGAAAA TTGCCTGGCG AATCAAATGA AGCATATGAG    2100

GCTAGACTCA AGGCTTTAGA GTTAGCAAGG GCCCAAAAAG CTCCAGAAGT CTCCAACCAA    2160

CCTCCCACAC TTGGAGGCAT TCTAGCCAAA AGGAAAAGAG TGATTGAGAA TGCACTCTCA    2220

AAGACAGTGG ATATGCGTGA AGTCTTAAGG CATGAATCTG TTGTACTCTC CCCGAATGTA    2280

ATGGACGAGG GAGCAATAGA CGAGCTGATT CGTGCCTTTG GGGAGTCGGG CATAGCTGAA    2340

AATGTGCAGT TTGATGTTGC AATAGACATT GCTCGCCACT GTTCTGATGT GGGGAGCTCT    2400

CAGAGGTCAA CCCTTATTGG TAAAAGCCCC TTCTGTGAGT TAAATAGGTC TGAAATTGCC    2460

GGAATAATAA GGGAGGTGAC CACGCTGCGC AGATTTTGCA TGTACTACGC AAAGATTGTG    2520

TGGAACATCC ATTTGGAGAC GGGAATACCA CCAGCTAATT GGGCCAAGAA AGGATTTAAT    2580

GAGAATGAAA AGTTTGCAGC CTTTGACTTC TTCCTTGGAG TCACAGATGA AAGCGCGCTT    2640

GAGCCTAAGG GTGGAGTCAA GAGAGCTCCA ACAAAAGCAG                         2680
```

The RSP47-4 strain contains five open reading frames (i.e., ORF1–5). ORF1 and ORF5 are only partially sequenced. RSP47-4 is 79% identical in nucleotide sequence to the corresponding region of RSPaV-1. The amino acid sequence identities between the corresponding ORFs of RSP47-4 and RSPaV-1 are: 94.1% for ORF1, 88.2% for ORF2, 88.9% for ORF3, 86.2% for ORF4, and 92.9% for ORF5. The nucleotide sequences of the five potential ORFs of RSP47-4 are given below.

Another DNA molecule of the present invention (RSP47-4 incomplete ORF1) includes nucleotides 1–768 of SEQ. ID. No. 12. This DNA molecule is believed to code for a polypeptide portion of a RSP47-4 replicase and comprises a nucleotide sequence corresponding to SEQ. ID. No. 13 as follows:

```
ATGCGATACA TTGAAAAGAA GCTTGTGCAG GCATTGAAAC CAAATTTCTA CATTCATTCT     60

GGCAAAGGTC TTGATGAGCT AAGTGAATGG GTTAGAGCCA GAGGTTTCAC AGGTGTGTGT    120

ACTGAGTCAG ACTATGAAGC TTTTGATGCA TCCCAAGATC ATTTCATCCT GGCATTTGAA    180

CTGCAAATCA TGAGATTTTT AGGACTGCCA GAAGATCTGA TTTTAGATTA TGAGTTCATC    240

AAAATTCATC TTGGGTCAAA GCTTGGCTCT TTTGCAATTA TGAGATTCAC AGGTGAGGCA    300

AGCACCTTCC TATTCAATAC TATGGCCAAC ATGCTATTCA CTTTCCTGAG GTATGAGTTG    360

ACAGGTTCTG AATCAATTGC ATTTGCTGGA GATGATATGT GTGCTAATCG CAGGTTAAGA    420

CTCAAGACTG AGCACGCCGG CTTTCTAAAC ATGATCTGTC TCAAAGCTAA GGTGCAGTTT    480

GTCACAAATC CCACCTTCTG TGGATGGTGT TTGTTTAAAG AGGGAATCTT TAAAAAACCC    540

CAGCTCATTT GGGAAAGGAT CTGCATTGCT AGGGAAATGG GTAACTTGGA CAATTGCATT    600

GACAATTACG CAATTGAGGT GTCTTATGCT TACAGACTTG GGGAATTGTC CATAGGCGTG    660

ATGACTGAGG AGGAAGTTGA AGCACATTCT AACTGCGTGC GTTTCCTGGT TCGCAATAAG    720

CACAAGATGA GGTGCTCAAT TTCTGGTTTG TTTGAAGTAA TTGTTTA                  767
```

The polypeptide has a deduced amino acid sequence corresponding to SEQ. ID. No. 14 as follows:

```
Met Arg Tyr Ile Glu Lys Lys Leu Val Gln Ala Leu Lys Pro Asn Phe
1               5                   10                  15

Tyr Ile His Ser Gly Lys Gly Leu Asp Glu Leu Ser Glu Trp Val Arg
                20                  25                  30

Ala Arg Gly Phe Thr Gly Val Cys Thr Glu Ser Asp Tyr Glu Ala Phe
            35                  40                  45

Asp Ala Ser Gln Asp His Phe Ile Leu Ala Phe Glu Leu Gln Ile Met
        50                  55                  60

Arg Phe Leu Gly Leu Pro Glu Asp Leu Ile Leu Asp Tyr Glu Phe Ile
65                      70                  75                  80

Lys Ile His Leu Gly Ser Lys Leu Gly Ser Phe Ala Ile Met Arg Phe
                85                  90                  95

Thr Gly Glu Ala Ser Thr Phe Leu Phe Asn Thr Met Ala Asn Met Leu
                100                 105                 110

Phe Thr Phe Leu Arg Tyr Glu Leu Thr Gly Ser Glu Ser Ile Ala Phe
            115                 120                 125

Ala Gly Asp Asp Met Cys Ala Asn Arg Arg Leu Arg Leu Lys Thr Glu
        130                 135                 140

His Ala Gly Phe Leu Asn Met Ile Cys Leu Lys Ala Lys Val Gln Phe
145                 150                 155                 160

Val Thr Asn Pro Thr Phe Cys Gly Trp Cys Leu Phe Lys Glu Gly Ile
                165                 170                 175

Phe Lys Lys Pro Gln Leu Ile Trp Glu Arg Ile Cys Ile Ala Arg Glu
            180                 185                 190

Met Gly Asn Leu Asp Asn Cys Ile Asp Asn Tyr Ala Ile Glu Val Ser
        195                 200                 205

Tyr Ala Tyr Arg Leu Gly Glu Leu Ser Ile Gly Val Met Thr Glu Glu
210                 215                 220

Glu Val Glu Ala His Ser Asn Cys Val Arg Phe Leu Val Arg Asn Lys
225                 230                 235                 240

His Lys Met Arg Cys Ser Ile Ser Gly Leu Phe Glu Val Ile Val
                245                 250                 255
```

Another DNA molecule of the present invention (RSP47-4 ORF2) includes nucleotides 857–1522 of SEQ. ID. No. 12. This DNA molecule codes for a first protein or polypeptide of an RSP47-4 triple gene block and comprises a nucleotide sequence corresponding to SEQ. ID. No. 15 as follows:

```
ATGAATAACT TAGTCAAAGC TTTGTCTGCT TTTGAATTTG TTGGTGTGTT TTGTGTACTT    60
AAATTTCCAG TTGTTGTTCA CAGTGTTCCA GGTAGCGGTA AAAGTAGCCT AATAAGGGAG   120
CTCATTTCTG AAGACGAGGC TTTTGTGCC  TTTACAGCAG GTGTGCCACA CAGTCCAAAT   180
CTGACAGGGA GGTACATCAA GCCCTACGCT CCAGGGTGTG CAGTGCAAGG GAAAATAAAC   240
ATACTTGATG AGTACTTGTC TGTCTCTGAT ACTTCTGGCT TTGATGTGCT GTTCTCAGAC   300
CCTTACCAGA ATGTCAGCAT TCCAAGGGAG GCACACTTCA TAAAACCAA  AACCTGTAGG   360
TTTGGTACCA ACACCTGCAA GTACCTTCAA TCTTTTGGCT TTAATGTTTG TAGTGATGGG   420
GTGGATAAAG TTGTTGTAGG GTCGCCATTT GAACTGGAGG TTGAGGGGGT TCTCATTTGC   480
TTTGGAAAGG AGGCTGTAGA TCTAGCAGTT GCACACAATT CTGACTTCAA GTTGCCCTGC   540
GAGGTGCGGG GTTCAACATT TGACGTTGTA ACGTTATTGA AGTCCAGGGA TCCAACTTCA   600
GAAGATAAGC ATTGGTTCTA CGTTGCAGCC ACAAGGCATC GAAGTAAACT GATAATAATG   660
CAGTAA                                                              666
```

The first protein or polypeptide of the RSP47-4 triple gene block has a deduced amino acid sequence corresponding to SEQ. ID. No. 16 as follows:

The second protein or polypeptide of the RSP47-4 triple gene block has a deduced amino acid sequence corresponding to SEQ. ID. No. 18 as follows:

```
Met Asn Asn Leu Val Lys Ala Leu Ser Ala Phe Glu Phe Val Gly Val
1               5                   10                  15

Phe Cys Val Leu Lys Phe Pro Val Val His Ser Val Pro Gly Ser
            20                  25                  30

Gly Lys Ser Ser Leu Ile Arg Glu Leu Ile Ser Glu Asp Glu Ala Phe
            35                  40                  45

Val Ala Phe Thr Ala Gly Val Pro Asp Ser Pro Asn Leu Thr Gly Arg
            50                  55                  60

Tyr Ile Lys Pro Tyr Ala Pro Gly Cys Ala Val Gln Gly Lys Ile Asn
65                      70                  75                  80

Ile Leu Asp Glu Tyr Leu Ser Val Ser Asp Thr Ser Gly Phe Asp Val
                85                  90                  95

Leu Phe Ser Asp Pro Tyr Gln Asn Val Ser Ile Pro Arg Glu Ala His
                100                 105                 110

Phe Ile Lys Thr Lys Thr Cys Arg Phe Gly Thr Asn Thr Cys Lys Tyr
            115                 120                 125

Leu Gln Ser Phe Gly Phe Asn Val Cys Ser Asp Gly Val Asp Lys Val
            130                 135                 140

Val Val Gly Ser Pro Phe Glu Leu Glu Val Glu Gly Val Leu Ile Cys
145                 150                 155                 160

Phe Gly Lys Glu Ala Val Asp Leu Ala Val Ala His Asn Ser Asp Phe
                165                 170                 175

Lys Leu Pro Cys Glu Val Arg Gly Ser Thr Phe Asp Val Val Thr Leu
            180                 185                 190

Leu Lys Ser Arg Asp Pro Thr Ser Glu Asp Lys His Trp Phe Tyr Val
            195                 200                 205

Ala Ala Thr Arg His Arg Ser Lys Leu Ile Ile Met Gln
        210                 215                 220
```

The first protein or polypeptide of the RSP47-4 triple gene block has a molecular weight of about 20 to 26 kDa., preferably 24.3 kDa.

Another DNA molecule of the present invention (RSP47-4 ORF3) includes nucleotides 1524–1877 of SEQ. ID. No. 12. This DNA molecule codes for a second protein or polypeptide of the RSP47-4 triple gene block and comprises a nucleotide sequence corresponding to SEQ. ID. No. 17 as follows:

```
ATGCCTTTTC AGCAACCTGC CAACTGGGCT AAGACCATAA CTCCATTAAC TATTGGTTTG    60

GGCATTGGGT TGGTTCTGCA CTTCTTAAGG AAATCAAATC TGCCATATTC AGGAGACAAT   120

ATTCACCAGT TCCCACACGG AGGGCATTAC AGGGACGGCA CGAAGAGTAT AACCTATTGT   180

GGCCCTAGGC AGTCATTCCC AAGCTCAGGA ATATTCGGTC AGTCTGAAAA TTTCGTACCT   240

CTAATATTGG TCGTGACTCT GGTCGCTTTT ATACATGCGT TATCTCTTTG GAATTCTGGT   300

CCTAGTAGGA GTTGCAATTG CCATCCAAAT CCTTGCACAT GTAGACAGCA GTAG          354
```

```
Met Pro Phe Gln Gln Pro Ala Asn Trp Ala Lys Thr Ile Thr Pro Leu
1               5                   10                  15

Thr Ile Gly Leu Gly Ile Gly Leu Val Leu His Phe Leu Arg Lys Ser
                20              25                  30

Asn Leu Pro Tyr Ser Gly Asp Asn Ile His Gln Phe Pro His Gly Gly
            35              40                  45

His Tyr Arg Asp Gly Thr Lys Ser Ile Thr Tyr Cys Gly Pro Arg Gln
        50              55                  60

Ser Phe Pro Ser Ser Gly Ile Phe Gly Gln Ser Glu Asn Phe Val Pro
65              70              75                  80

Leu Ile Leu Val Val Thr Leu Val Ala Phe Ile His Ala Leu Ser Leu
                85              90                  95

Trp Asn Ser Gly Pro Ser Arg Ser Cys Asn Cys His Pro Asn Pro Cys
            100             105                 110

Thr Cys Arg Gln Gln
            115
```

The second protein or polypeptide of the RSP47-4 triple gene block has a molecular weight of about 10 to 15 kDa., preferably 12.9 kDa.

Another DNA molecule of the present invention (RSP47-4 ORF4) includes nucleotides 1798–2040 of SEQ. ID. No. 12. This DNA molecule codes for a third protein or polypeptide of the RSP47-4 triple gene block and comprises a nucleotide sequence corresponding to SEQ. ID. No. 19 as follows:

The third protein or polypeptide of the RSP47-4 triple gene block has a molecular weight of about 5 to 10 kDa., preferably 8.3 kDa.

Yet another DNA molecule of the present invention (RSP47-4 ORF5) includes nucleotides 2050–2680 of SEQ. ID. No. 12. This DNA molecule codes for a partial RSP47-4 coat protein or polypeptide and comprises a nucleotide sequence corresponding to SEQ. ID. No. 21 as follows:

```
ATGCGTTATC TCTTTGGAAT TCTGGTCCTA GTAGGAGTTG CAATTGCCAT CCAAATCCTT    60

GCACATGTAG ACAGCAGTAG TGGCAACCAT CAAGGCTGTT TCATAAGAGC CACCGGGGAG   120

TCAATAGTAA TTGAGAATTG TGGGCCGAGC GAGGCCCTAG CTGCTACAGT CAAAGAGGTG   180

TTGGGCGGTC TAAAGGCTTT AGGGGTTAGC CAAAAGGTTG ATGAAATTAA TTACAGTTGT   240

TGA                                                                 243
```

The third protein or polypeptide of the RSP47-4 triple gene block has a deduced amino acid sequence corresponding to SEQ. ID. No. 20 as follows:

```
Met Arg Tyr Leu Phe Gly Ile Leu Val Leu Val Gly Val Ala Ile Ala
1               5                   10                  15

Ile Gln Ile Leu Ala His Val Asp Ser Ser Ser Gly Asn His Gln Gly
                20              25                  30

Cys Phe Ile Arg Ala Thr Gly Glu Ser Ile Val Ile Glu Asn Cys Gly
            35              40                  45

Pro Ser Glu Ala Leu Ala Ala Thr Val Lys Glu Val Leu Gly Gly Leu
        50              55                  60

Lys Ala Leu Gly Val Ser Gln Lys Val Asp Glu Ile Asn Tyr Ser Cys
65              70              75                  80
```

```
ATGGCAAGTC AAGTTGGAAA ATTGCCTGGC GAATCAAATG AAGCATATGA GGCTAGACTC    60

AAGGCTTTAG AGTTAGCAAG GGCCCAAAAA GCTCCAGAAG TCTCCAACCA ACCTCCCACA   120

CTTGGAGGCA TTCTAGCCAA AAGGAAAAGA GTGATTGAGA ATGCACTCTC AAAGACAGTG   180

GATATGCGTG AAGTCTTAAG GCATGAATCT GTTGTACTCT CCCCGAATGT AATGGACGAG   240

GGAGCAATAG ACGAGCTGAT TCGTGCCTTT GGGGAGTCGG GCATAGCTGA AAATGTGCAG   300

TTTGATCTTG CAATAGACAT TGCTCGCCAC TGTTCTGATG TGGGGAGCTC TCAGAGGTCA   360

ACCCTTATTG GTAAAAGCCC CTTCTGTGAG TTAAATAGGT CTGAAATTGC CGGAATAATA   420

AGGGAGGTGA CCACGCTGCG CACATTTTGC ATGTACTACG CAAAGATTGT GTGGAACATC   480

CATTTGGAGA CGGGAATACC ACCAGCTAAT TGGGCCAAGA AAGGATTTAA TGAGAATGAA   540

AAGTTTGCAG CCTTTGACTT CTTCCTTGGA GTCACAGATG AAAGCGCGCT TGAGCCTAAG   600

GGTGGAGTCA AGAGAGCTCC AACAAAAGCA G                                 631
```

The polypeptide has a deduced amino acid sequence corresponding to SEQ. ID. No. 22 as follows:

```
Met Ala Ser Gln Val Gly Lys Leu Pro Gly Glu Ser Asn Glu Ala Tyr
1               5                   10                  15

Glu Ala Arg Leu Lys Ala Leu Glu Leu Ala Arg Ala Gln Lys Ala Pro
            20                  25                  30

Glu Val Ser Asn Gln Pro Pro Thr Leu Gly Gly Ile Leu Ala Lys Arg
        35                  40                  45

Lys Arg Val Ile Glu Asn Ala Leu Ser Lys Thr Val Asp Met Arg Glu
50                  55                  60

Val Leu Arg His Glu Ser Val Val Leu Ser Pro Asn Val Met Asp Glu
65                  70                  75                  80

Gly Ala Ile Asp Glu Leu Ile Arg Ala Phe Gly Glu Ser Gly Ile Ala
                85                  90                  95

Glu Asn Val Gln Phe Asp Val Ala Ile Asp Ile Ala Arg His Cys Ser
            100                 105                 110

Asp Val Gly Ser Ser Gln Arg Ser Thr Leu Ile Gly Lys Ser Pro Phe
        115                 120                 125

Cys Glu Leu Asn Arg Ser Glu Ile Ala Gly Ile Ile Arg Glu Val Thr
130                 135                 140

Thr Leu Arg Arg Phe Cys Met Tyr Tyr Ala Lys Ile Val Trp Asn Ile
145                 150                 155                 160

His Leu Glu Thr Gly Ile Pro Pro Ala Asn Trp Ala Lys Lys Gly Phe
                165                 170                 175

Asn Glu Asn Glu Lys Phe Ala Ala Phe Asp Phe Phe Leu Gly Val Thr
            180                 185                 190

Asp Glu Ser Ala Leu Glu Pro Lys Gly Gly Val Lys Arg Ala Pro Thr
        195                 200                 205

Lys Ala
    210
```

The DNA molecule which constitutes a substantial portion of the RSPaV strain RSP158 genome comprises the nucleotide sequence corresponding to SEQ. ID. No. 23 as follows:

```
GAAGCTAGCA CATTTCTGTT CAACACTATG GCTAACATGT TGTTCACTTT TCTGAGATAT      60
GAACTGACGG GTTCAGAGTC AATAGCATTT GCAGGGGATG ATATGTGTGC TAATAGAAGG     120
TTGCGGCTTA AAACGGAGCA TGAGGGTTTT CTGAACATGA TCTGCCTTAA GGCCAAGGTT     180
CAGTTTGTTT CCAACCCCAC ATTCTGTGGA TGGTGCTTAT TTAAGGAGGG AATCTTCAAG     240
AAACCTCAAC TAATTTGGGA GCGAATATGC ATAGCCAGAG AGATGGGCAA TCTGGAGAAC     300
TGTATTGACA ATTATGCGAT AGAAGTGTCC TATGCATATA GATTGGGTGA GCTATCAATT     360
GAAATGATGA CAGAAGAAGA AGTGGAGGCA CACTACAATT GTGTGAGGTT CCTGGTTAGG     420
AACAAGCATA AGATGAGGTG CTCAATTTCA GGCCTGTTTG AAGTGGTTGA TTAGGCCTTA     480
AGTATTTGGC GTTGTTCGAG TTATTATGAA TAATTTAGTT AAAGCATTAT CAGCCTTCGA     540
GTTTATAGGT GTTTTCAATG TGCTCAAATT TCCAGTTGTT ATACATAGTG TGCCTGGTAG     600
TGGTAAGAGT AGCTTAATAA GGGAATTAAT CTCAGAGGAC GAGAGTTTCG TGCCTTTCAC     660
AGCAGGTGTT CCAGACAGTC CTAACCTCAC AGGGAGGTAC ATCAAGCCTT ACTCACCAGG     720
ATGCGCAGTG CAAGGAAAAG TGAATATACT TGATGAGTAC TTGTCCGTTC AAGACATTTC     780
GGGTTTTGAT GTACTGTTTT CAGACCCGTA CCAGAATATC AGTATTCCCC AAGAGGCGCA     840
TTTCATTAAG TCCAAGACTT GTAGGTTTGG TGTGAACACT TGCAAATACC TTTCCTCTTT     900
CGGTTTCGAA GTTAGCAGCG ACGGGCTGGA CGACGTCATT GTGGGATCGC CCTTCACTCT     960
AGATGTTGAA GGGGTGCTGA TATGTTTTGG CAAGGAGGCG GTAGATCTCG CTGTTGCGCA    1020
CAACTCTGAA TTCAAGTTGC CGTGTGAGGT TCGAGGTTCA ACCTTCAATG TGGTAACCCT    1080
TTTGAAATCA AGAGACCCAA CCCCAGAGGA CAGGCACTGG TTTTACATCG CTGCCACAAG    1140
ACATAGGAAG AAATTGGTCA TTATGCAGTA AAATGCCTTT TCAGCAGCCT GCTAATTGGG    1200
CAAAAACCAT AACTCCATTG ACTATTGGCT TAGGAATTGG ACTTGTGCTG CATTTCTGA     1260
GAAAGTCAAA TCTACCATAT TCAGGAGACA ACATCCATCA ATTTCCTCAC GGGGGGCGTT    1320
ACCGGGACGG CACAAAAAGT ATAACTTACT GTGGCCCTAA GCAGTCCTTC CCCAGTTCAG    1380
GAATATTTGG TCAGTCTGAG AATTTTGTGC CCTTAATGCT TGTCATAGGT CTAATTGCAT    1440
TCATACATGT ATTGTCTGTT TGGAATTCTG GTCTTGGTAG GAATTGCAAT TGCCATCCAA    1500
ATCCTTGCTC ATGTAGACAA CAGTAGTGGC AGTCACCAAG GTTGCTTTAT CAGGGCCACT    1560
GGAGAGTCTA TTTTGATTGA AAATTGTGGC CCAAGCGAGG CCCTTGCATC AACAGTGAGG    1620
GAGGTGTTGG GGGGTTTGAA GGCTTTAGGA ATTAGCCATA CTACTGAAGA AATTGATTAT    1680
CGTTGTTAAA TTGGTTAAAT GGCGAGTCAA GTTGGTAAGC TCCCCGGAGA ATCAAATGAG    1740
GCATTTGAAG CCCGGCTGAA ATCACTGGAG TTGGCTAGAG CTCAAAAGCA GCCAGAAGGT    1800
TCAAACACAC CGCCTACTCT CAGTGGTGTG CTTGCCAAAC GTAAGAGGGT TATTGAGAAT    1860
GCACTCTCAA AGACAGTGGA CATGAGGGAG GTGTTGAAAC ACGAAACGGT TGTAATTTCC    1920
CCAAATGTCA TGGATGAGGG TGCAATAGAT GAACTGATTC GTGCATTCGG AGAATCAGGC    1980
ATAGCTGAGA GCGCACAATT TGATGTGGC                                     2009
```

The RSP158 strain contains five open reading frames (i.e., ORF1–5). ORF1 and ORF5 are only partially sequenced. The nucleotide sequence of RSP158 is 87.6% identical to the corresponding region of RSPaV-1 (type strain). The numbers of amino acid residues of corresponding ORFs of RSP158 and RSPaV-1 (type strain) are exactly the same. In addition, the amino acid sequences of these ORFs have high identities to those of RSPaV-1: 99.3% for ORF1, 95% for ORF2, 99.1% for ORF3, 88.8% for ORF4, and 95.1% for ORF5. The nucleotide and amino acid sequence information of the RSP158 ORFs are described below.

Another DNA molecule of the present invention (RSP158 incomplete ORF 1) includes nucleotides 1–447 of SEQ. ID. No. 23. This DNA molecule is believed to code for a polypeptide portion of a RSP158 replicase and comprises a nucleotide sequence corresponding to SEQ. ID. No. 24 as follows:

```
GAAGCTAGCA CATTTCTGTT CAACACTATG GCTAACATGT TGTTCACTTT TCTGAGATAT    60

GAACTGACGG GTTCAGAGTC AATAGCATTT GCAGGGGATG ATATGTGTGC TAATAGAAGG   120

TTGCGGCTTA AAACGGAGCA TGAGGGTTTT CTGAACATGA TCTGCCTTAA GGCCAAGGTT   180

CAGTTTGTTT CCAACCCCAC ATTCTGTGGA TGGTGCTTAT TTAAGGAGGG AATCTTCAAG   240

AAACCTCAAC TAATTTGGGA GCGAATATGC ATAGCCAGAG AGATGGGCAA TCTGGAGAAC   300

TGTATTGACA ATTATGCGAT AGAAGTGTCC TATGCATATA GATTGGGTGA GCTATCAATT   360

GAAATCATCA CAGAAGAAGA AGTGGAGGCA CACTACAATT GTGTGAGGTT CCTGGTTAGG   420

AACAAGCATA AGATGAGGTG CTCAATT                                      447
```

The polypeptide encoded by the nucleotide sequence of SEQ. ID. No. 24 has a deduced amino acid sequence corresponding to SEQ. ID. No. 25 as follows:

This DNA molecule codes for a first protein or polypeptide of the RSP158 triple gene block and comprises a nucleotide sequence corresponding to SEQ. ID. No. 26 as follows:

```
Glu Ala Ser Thr Phe Leu Phe Asn Thr Met Ala Asn Met Leu Phe Thr
1               5                   10                  15

Phe Leu Arg Tyr Glu Leu Thr Gly Ser Glu Ser Ile Ala Phe Ala Gly
                20                  25                  30

Asp Asp Met Cys Ala Asn Arg Arg Leu Arg Leu Lys Thr Glu His Glu
            35                  40                  45

Gly Phe Leu Asn Met Ile Cys Leu Lys Ala Lys Val Gln Phe Val Ser
    50                  55                  60

Asn Pro Thr Phe Cys Gly Trp Cys Leu Phe Lys Glu Gly Ile Phe Lys
65                  70                  75                  80

Lys Pro Gln Leu Ile Trp Glu Arg Ile Cys Ile Ala Arg Glu Met Gly
                85                  90                  95

Asn Leu Glu Asn Cys Ile Asp Asn Tyr Ala Ile Glu Val Ser Tyr Ala
                100                 105                 110

Tyr Arg Leu Gly Glu Leu Ser Ile Glu Met Met Thr Glu Glu Glu Val
            115                 120                 125

Glu Ala His Tyr Asn Cys Val Arg Phe Leu Val Arg Asn Lys His Lys
    130                 135                 140

Met Arg Cys Ser Ile
145
```

Another DNA molecule of the present invention (RSP158 ORF2) includes nucleotides 506–1171 of SEQ. ID. No. 23.

```
                              ATGAATAATT TAGTTAAAGC ATTATCAGCC TTCGAGTTTA TAGGTGTTTT CAATGTGCTC    60

AAATTTCCAG TTGTTATACA TAGTGTGCCT GGTAGTGGTA AGAGTAGCTT AATAAGGGAA   120

TTAATCTCAG AGGACGAGAG TTTCGTGGCT TCACAGCAG GTGTTCCAGA CAGTCCTAAC   180

CTCACAGGGA GGTACATCAA GCCTTACTCA CCAGCATGCG CAGTGCAACC AAAAGTCAAT   240

ATACTTGATG AGTACTTGTC CGTTCAAGAC ATTTCGGGTT TTGATGTACT GTTTTCAGAC   300

CCGTACCAGA ATATCAGTAT TCCCCAAGAG GCGCATTTCA TTAAGTCCAA GACTTGTAGG   360

TTTGGTGTGA ACACTTGCAA ATACCTTTCC TCTTTCGGTT TCGAAGTTAG CAGCGACGGG   420

CTGGACGACG TCATTGTGGG ATCGCCCTTC ACTCTAGATG TTGAAGGGGT GCTGATATGT   480

TTTGGCAAGG AGCCGGTACA TCTCCCTGTT CCGCACAACT CTGAATTCAA GTTCCCGTGT   540

GAGGTTCGAG GTTCAACCTT CAATGTGGTA ACCCTTTTGA AATCAAGAGA CCCAACCCCA   600
```

-continued

```
GAGGACAGGC ACTGGTTTTA CATCGCTGCC ACAAGACATA GGAAGAAATT GGTCATTATG    660

CAGTAA                                                               666
```

The first protein or polypeptide of the RSP158 triple gene block has a deduced amino acid sequence corresponding to SEQ. ID. No. 27 as follows:

tide of the RSP158 triple gene block and comprises a nucleotide sequence corresponding to SEQ. ID. No. 28 as follows:

```
Met Asn Asn Leu Val Lys Ala Leu Ser Ala Phe Glu Phe Ile Gly Val
1               5                   10                  15

Phe Asn Val Leu Lys Phe Pro Val Val Ile His Ser Val Pro Gly Ser
            20                  25                  30

Gly Lys Ser Ser Leu Ile Arg Glu Leu Ile Ser Glu Asp Glu Ser Phe
            35                  40                  45

Val Ala Phe Thr Ala Gly Val Pro Asp Ser Pro Asn Leu Thr Gly Arg
    50                  55                  60

Tyr Ile Lys Pro Tyr Ser Pro Gly Cys Ala Val Gln Gly Lys Val Asn
65              70                  75                  80

Ile Leu Asp Glu Tyr Leu Ser Val Gln Asp Ile Ser Gly Phe Asp Val
            85                  90                  95

Leu Phe Ser Asp Pro Tyr Gln Asn Ile Ser Ile Pro Gln Glu Ala His
            100                 105                 110

Phe Ile Lys Ser Lys Thr Cys Arg Phe Gly Val Asn Thr Cys Lys Tyr
            115                 120                 125

Leu Ser Ser Phe Gly Phe Glu Val Ser Ser Asp Gly Leu Asp Asp Val
    130                 135                 140

Ile Val Gly Ser Pro Phe Thr Leu Asp Val Glu Gly Val Leu Ile Cys
145                 150                 155                 160

Phe Gly Lys Glu Ala Val Asp Leu Ala Val Ala His Asn Ser Glu Phe
                165                 170                 175

Lys Leu Pro Cys Glu Val Arg Gly Ser Thr Phe Asn Val Val Thr Leu
            180                 185                 190

Leu Lys Ser Arg Asp Pro Thr Pro Glu Asp Arg His Trp Phe Tyr Ile
    195                 200                 205

Ala Ala Thr Arg His Arg Lys Lys Leu Val Ile Met Gln
    210                 215                 220
```

The first protein or polypeptide of the RSP158 triple gene block has a molecular weight of about 20 to 26 kDa., preferably 24.4 kDa.

```
ATGCCTTTTC AGCAGCCTGC TAATTGGGCA AAAACCATAA CTCCATTGAC TATTGGCTTA    60

GGAATTGGAC TTGTGCTGCA TTTTCTGAGA AAGTCAAATC TACCATATTC AGGAGACAAC   120

ATCCATCAAT TTCCTCACGG GGGGCGTTAC CGGGACGGCA CAAAAAGTAT AACTTACTGT   180

GGCCCTAAGC AGTCCTTCCC CAGTTCAGGA ATATTTGGTC AGTCTGAGAA TTTTGTGCCC   240

TTAATGCTTG TCATAGGTCT AATTGCATTC ATACATGTAT TGTCTGTTTG GAATTCTGGT   300

CTTGGTAGGA ATTGCAATTG CCATCCAAAT CCTTGCTCAT GTAGACAACA GTAG         354
```

Another DNA molecule of the present invention (RSP158 ORF3) includes nucleotides 1173–1526 of SEQ. ID. No. 23. This DNA molecule codes for a second protein or polypep- The second protein or polypeptide of the RSP158 triple gene block has a deduced amino acid sequence corresponding to SEQ. ID. No. 29 as follows:

```
Met Pro Phe Gln Gln Pro Ala Asn Trp Ala Lys Thr Ile Thr Pro Leu
1               5                   10                  15

Thr Ile Gly Leu Gly Ile Gly Leu Val Leu His Phe Leu Arg Lys Ser
                20                  25                  30

Asn Leu Pro Tyr Ser Gly Asp Asn Ile His Gln Phe Pro His Gly Gly
            35                  40                  45

Arg Tyr Arg Asp Gly Thr Lys Ile Thr Tyr Cys Gly Pro Lys Gln Ser
        50                  55                  60

Phe Pro Ser Ser Gly Ile Phe Gly Gln Ser Glu Asn Phe Val Pro Leu
65                  70                  75                  80

Met Leu Val Ile Gly Leu Ile Ala Phe Ile His Val Leu Ser Val Trp
                85                  90                  95

Asn Ser Gly Leu Gly Arg Asn Cys Asn Cys His Pro Asn Pro Cys Ser
            100                 105                 110

Cys Arg Gln Gln
        115
```

The second protein or polypeptide of the RSP158 triple gene block has a molecular weight of about 10 to 15 kDa., preferably 12.9 kDa.

Another DNA molecule of the present invention (RSP158 ORF4) includes nucleotides 1447–1689 of SEQ. ID. No. 23. This DNA molecule codes for a third protein or polypeptide of the RSP158 triple gene block and comprises a nucleotide sequence corresponding to SEQ. ID. No. 30 as follows:

```
ATGTATTGTC TGTTTGGAAT TCTGGTCTTG GTAGGAATTG CAATTGCCAT CCAAATCCTT    60

GCTCATGTAG ACAACAGTAG TGGCAGTCAC CAAGGTTGCT TTATCAGGGC CACTGGAGAG   120

TCTATTTTGA TTGAAAATTG TGGCCCAAGC GAGGCCCTTG CATCAACAGT GAGGGAGGTG   180

TTGGGGGGTT TGAAGGCTTT AGGAATTAGC CATACTACTG AAGAAATTGA TTATCGTTGT   240

TAA                                                                 243
```

The third protein or polypeptide of the RSP158 triple gene block has a deduced amino acid sequence corresponding to SEQ. ID. No. 31 as follows:

```
Met Tyr Cys Leu Phe Gly Ile Leu Val Leu Val Gly Ile Ala Ile Ala
1               5                   10                  15

Ile Gln Ile Leu Ala His Val Asp Asn Ser Ser Gly Ser His Gln Gly
                20                  25                  30

Cys Phe Ile Arg Ala Thr Gly Glu Ser Ile Leu Ile Glu Asn Cys Gly
            35                  40                  45

Pro Ser Glu Ala Leu Ala Ser Thr Val Arg Glu Val Leu Gly Gly Leu
        50                  55                  60

Lys Ala Leu Gly Ile Ser His Thr Thr Glu Glu Ile Asp Tyr Arg Cys
65                  70                  75                  80
```

The third protein or polypeptide of the RSP158 triple gene block has a molecular weight of about 5 to 10 kDa., preferably 8.4 kDa.

Yet another DNA molecule of the present invention (RSP158 ORF5) includes nucleotides 1699–2009 of SEQ. ID. No. 23. This DNA molecule codes for a partial RSP158 coat protein or polypeptide and comprises a nucleotide sequence corresponding to SEQ. ID. No. 32 as follows:

```
ATGGCGAGTC AAGTTGGTAA GCTCCCCGGA GAATCAAATG AGGCATTTGA AGCCCGGCTG    60

AAATCACTGG AGTTGGCTAG AGCTCAAAAG CAGCCAGAAG GTTCAAACAC ACCGCCTACT   120

CTCAGTGGTG TGCTTGCCAA ACGTAAGAGG GTTATTGAGA ATGCACTCTC AAAGACAGTG   180

GACATGAGGG AGGTGTTGAA ACACGAAACG GTTGTAATTT CCCCAAATGT CATGGATGAG   240

GGTGCAATAG ATGAACTGAT TCGTGCATTC GGAGAATCAG GCATAGCTGA GAGCGCACAA   300

TTTGATGTGG C                                                       311
```

The polypeptide has a deduced amino acid sequence corresponding to SEQ. ID. No. 33 as follows:

```
Met Ala Ser Gln Val Gly Lys Leu Pro Gly Glu Ser Asn Glu Ala Phe
1               5                   10                  15

Glu Ala Arg Leu Lys Ser Leu Glu Leu Ala Arg Ala Gln Lys Gln Pro
                20                  25                  30

Glu Gly Ser Asn Thr Pro Pro Thr Leu Ser Gly Val Leu Ala Lys Arg
                35                  40                  45

Lys Arg Val Ile Glu Asn Ala Leu Ser Lys Thr Val Asp Met Arg Glu
        50                  55                  60

Val Leu Lys His Glu Thr Val Val Ile Ser Pro Asn Val Met Asp Glu
65                  70                  75                  80

Gly Ala Ile Asp Glu Leu Ile Arg Ala Phe Gly Glu Ser Gly Ile Ala
                85                  90                  95

Glu Ser Ala Gln Phe Asp Val
                100
```

The following seven cDNA clones are located at the central part of the ORF1 of RSPaV-1 and all have high identities (83.6–98.4%) in nucleotide sequence with the comparable regions of RSPaV-1. When their nucleotide sequences are aligned with MegAlign (DNAStar), a highly conserved region of ca. 600 nucleotides was found. The universal primers BM98-3F/BM98-3R (SEQ. ID. Nos. 51 and 52, infra) were designed based on the conserved nucleotide sequences of this region.

Portions of the genome from yet other strains of *Rupestris* stem pitting associated viruses have also been isolated and sequenced. These include strains designated 140/94-19 (T7+R1), 140/94-24 (T7+R1), 140/94-2 (T3+F1), 140/94+42 (T7+R1), 140/94-64 (T7+R1), 140-94-72 (T7+R1), and 140/94-6 (T3+BM98-3F+F2).

The nucleotide sequence of 140/94-19 (T7+R1) corresponds to SEQ. ID. No. 34 as follows:

```
GCAGGATTGA AGGCTGGCCA CTGTGTGATT TTTGATGAGG TCCAGTTGTT TCCTCCTGGA    60

TACATCGATC TATGCTTGCT TATTATACGT AGTGATGCTT TCATTTCACT TGCCGGTGAT   120

CCATGTCAAA GCACATATGA TTCGCAAAAG GATCGGGCAA TTTTGGGCGC TGAGCAGAGT   180

GACATACTTA GAATGCTTGA GGGCAAAACG TATAGGTATA ACATAGAAAG CAGGAGGTTT   240

GTGAACCCAA TCTTCGAATC AAGACTGCCA TGTCACTTCA AAAAGGGTTC GATGACTGCC   300

GCTTTCGCTG ATTATGCAAT CTTCCATAAT ATGCATGACT TTCTCCTGGC GAGGTCAAAA   360

GGTCCTTTGG ATGCCGTTTT GGTTTCCAGT TTTGAGGAGA AAAAGATAGT CCAGTCCTAC   420

TTTGGAATGA AACAGCTCAC ACTCACATTT GGTGAATCAA CTGGGTTGAA TTTCAAAAAT   480

GGGGGAATTC TCATATCACA TGATTCCTTT CACACAGATG ATCGGCCGGT GGCTTACTGC   540

TTTATCTCGC TTCAGCCACA ATTTGGATTT GGTGAACATT ACAGGTCTGA GGGTGGAAAG   600

TTTCCTCTCG CACTTTGCTG GCAAACCCCT CTACCATTTT TTAACAGCCA AAAGTGGGGA   660

GAATGTCATA CGAGATTTGC TCCCAGGTGA GCCTAACTTC TTCAGTGGCT TTAACGTTAG   720
```

```
                                            -continued
CATTGGAAAG AATGAAGGTG TTAGGGAGGA GAAGTTATGT GGTGACCCAT GGTTAAAAGT      780

CATGCTTTTC CTGGGTCAAG ATGAGGATTG TGAAGTTGAA GAGATGGAGT CAGAGTGCTC      840

AAATGAAGAA TGGTTTAAAA CCCACATTCC CCTGAGTAAT CTGGAGTCAA CCAGGGCTAG      900

GTGGGTGGGT AAAATGGCTT TGAAAGAGTA TCGCGAGGTG CGTTGTGGTT ATGAAATGAC      960

TCAACAATTC TTTGATGAGC ATAGGGGTGG AACTGGTGAG CAACTGAGCA ATGCATGTGA     1020

GAGGTTTGAA AGCATTTACC CAAGGCATAA AGGAAATGAT TCAATAACCT TCCTTATGGC     1080

TGTCCGAAAG CGTCTCAAAT TTTCGAAGCC CCAGGTTGAA GCTGCCAAAC TGAGGCGGGC     1140

CAAACCATAT GGGAAATTCT TATTAGACTT TCCTATCCAA AATCCCATTG AAAGCCAGTC     1200

ATAATT                                                                1206
```

The nucleotide sequence of 140/94-24 (T7+R1) corresponds to SEQ. ID. No. 35 as follows:

```
ATTAACCCAA ATGGTAAGAT TTCCGCCTTG TTTGATATAA CCAATGAGCA CATAAGGCAT       60

GTTGAGAAGA TCGGCAATGG CCCTCAGAGC ATAAAAGTAG ATGAGTTGAG GAAGGTTAAG      120

CGATCCGCCC TTGATCTTCT TTCAATGAAT GGGTCCAAAA TAACCTATTT TCCAAACTTT      180

GAGCGGGCTG AAAAGTTGCA AGGGTGCTTG CTAGGGGGCC TAACTGGTGT CATAAGTGAT      240

GAAAAGTTCA GTGATGCAAA ACCCTGGCTT TCTGGTATAT CAACTGCGGA TATAAAGCCA      300

AGAGAGCTAA CTGTCGTGCT TGGCACTTTT GGGGCTGGAA AGAGTTTCTT GTATAAGAGT      360

TTCATGAAGA GATCTGAGGG AAAATTTGTA ACTTTTGTTT CCCCTAGACG AGCCTTGGCA      420

AATTCAATCA AAAATGATCT TGAAATGGAT GATGGCTGCA AAGTTGCCAA AGCAGGCAAA      480

TCAAAGAAGG AAGGGTGGGA TGTAGTGACC TTTGAAGTTT TCCTTAGAAA AGTTTCTGGT      540

TTGAAAGCTG GTCATTGTGT GATTTTTGAT GAGGTTCAGT TGTTTCCCCC TGGATACATC      600

GATCTGTGTT TACTTGTCAT ACGAAGTGAT GCTTTCATTT CACTTGCTGG TGATCCATGC      660

CAGAGCACAT ATGATTCACA GAAGGATCGA GCAATTTTGG GAGCTGAGCA GAGTGACATA      720

CTCAGACTGC TTGAAGGAAA GACATATAGG TACAACATAG AAAGCAGACG TTTTGTGAAC      780

CCAATGTTTG AATCTAGACT ACCATGTCAC TTCAAAAAGG GTTCAATGAC TGCAGCCTTT      840

GCTGATTATG CAATCTTCCA CAATATGCAT GACTTCCTCC TGGCGAGGTC AAAAGGCCCC      900

TTGGATGCTG TTCTAGTTTC CAGTTTTGAG GAGAAGAAAA TAGTCCAATC CTACTTTGGG      960

ATGAAGCAAC TCACTCTCAC ATTTGGTGAA TCAACTGGGT TGAACTTCAA AAATGGAGGA     1020

ATTCTCATAT CACATGACTC CTTTCATACT GACGATCGAC GGTGGCTTAC TGCTTTATCT     1080

CGATTCAGCC ATAATTTGGA TTTGGTGAAC ATCACAGGTC TTGAGGGTGG AAAGTTTTCT     1140

CTCACATTTT GCTGGTAAAC CCCTTTACCA CTTTTTGACG GCTTAAAAGT GGAGAGAATG     1200

TCATACGAGA CCTGCTTCAG GTGAGCCTAA CTTCTTTTAG GGGTTCAATG TCAGCATTGG     1260

AAAAAAATGG AAGGGGTTAG AGAA                                            1284
```

The nucleotide sequence of 140/94-2 (T3+F1) corresponds to SEQ. ID. No. 36 as follows:-

```
CATTTTTAAA ATTTAATCCA GTCGACTCAC CAAATGTGAG CGTAAGCTGT TTCATCCCAA      60
AGTAGGACTG GACTATTTTC TTCTCCTCAA AACTAGAAAC CAGAATGGCA TCCAAAGGAC     120
CTTTTGACCT TGCCAGGAGG AAATCATGCA TATTGTGGAA AATGGCATAA TCAGCAAAGG     180
CAGCAGTCAT TGTACCCTTT TTGAAGTGAC ATGGCAGTCG AGATTCAAAC ATTGGGTTCA     240
CAAATCTTCT GCTTTCTATG TTGTACCTAT ACGTCTTGCC TTCAAGTATT TTGAGTATGT     300
CACTCTGCTC AGCGCCCAAA ATCGCCCGAT CTTTTTGTGA GTCATATGTG CTCTGACATG     360
GGTCACCAGC AAGTGAAATG AAAGCATCAC TACGTATAAT AAGCAAACAT AGATCGATGT     420
ATCCAGGGGG AAACAACTGG ACCTCATCGA AAATTACACA GTGACCAGCT TTTAGACCTG     480
CAACTTTTCT AAGGAAGACT TCAAAAGTCA CAACATCCCA TCCTTCCTTC TTTGACCTGC     540
CTGCTTTGGC AACTTTGCAG CTATCATCCA TTTCAAGATC ATTTTTGATT GAATTCGCTA     600
GAGCCCGTCT GGGGGAAACA AAAGTTACGA ATTTACCCTC AGATCTTTTC ATAAAGCTCT     660
TGTACAAAAA GCTTTTTCCG GCTCCAAATG TGCCAAGCAC AACAGTTAGC TCCCTCGGCT     720
TAATGTCAGT AGTTGATATA CCAGAAAGCC AGGGCTTTGC ATCACTGAAC TTCTCATCAC     780
TTATGACACC AGTAGGCCT CCTAGCAGAC ACCCTTGCAA CTTTTCAGCC CGCTCAAAAC     840
TTGGGAAGTA GGTTACCTTG GACCCATTAA TTGAAAGAAG ATCAAGGGCG GATCGCTTGA     900
CCTTTCGCAA TTCATCTACT TTAATGCTCT GAGGGCCATT ACCTATCTTT TCAACATGCC     960
TTATGTGCTC ATTAGTTATG TCAAACAGAG CGGAAAACTT GCCATGTGGA TTAATCACCT    1020
CAATTTCCCC ATTTATGTCA CACTTAGCGC AAATGTCAAA AGCCTCAAAG GCTTCAGCTA    1080
AGTTACATCA TGTTGAGCCT CCCCCTTGGC AAAGCTCCTC AAAAATGTGG TTAGTGCTAG    1140
GCCTGCACAA TAATTAACAC ATCAACTTCA CCCTGCCAAT GCTGAACAAT ACTGTTATCA    1200
TGCAACCATC CATGGGCAC ATGGTTGGAA TTGATTGATT TAAGGCAAAA ATCCCCACAG    1260
GGGGCATCCC CTTCCCCAAT TTCCACTGAT TCATACTCTG GCGTTATCAT ATCAACCCAA    1320
TGTGTCAAAT ACAAATAATG CAATCTCTCA TCTCCGATAA CATTTCCCCC ATTTTTTAAA    1380
AATGGTGGGG TGAAAATTGG AA                                            1402
```

The nucleotide sequence of 140/94-42 (T7+R1) corresponds to SEQ. ID. No. 37 as follows:

```
GTGGTTTTTG CAACAACAGG CCCAGGTCTA TCTAAGGTTT TGGAAATGCC TCGAAGCAAG      60
AAGCAATCTA TTCTGGTTCT TGAGGGAGCC CTATCCATAG AAACGGACTA TGGCCCAAAA     120
GTTCTGGGAT CTTTTGAAGT TTTCAAAGGG GATTTCAACA TTAAAAAAAT GGAAGAAAGT     180
TCCATCTTTG TAATAACATA CAAGGCCCCA GTTAGATCTA CTGGCAAGTT GAGGGTCCAC     240
CAATCAGAAT GCTCATTTTC TGGATCCAAG GAGGTATTGC TGGGTTGTCA GATTGAGGCA     300
TGTGCTGATT ATGATATTGA TGATTTCAAT ACTTTCTTTG TACCTGGTGA TGGTAATTGC     360
TTTTGGCATT CAGTTGGTTT CTTACTCAGT ACTGACGGAC TTGCTTTGAA GGCCGGCATT     420
CGTTCTTTCG TGGAGAGTGA ACGCCTGGTG AGTCCAGATC TTTCAGCCCC AACCATTTCT     480
AAACAACTGG GGGAAAATGC TTATGCCGAG AATGAGATGA TTGCATTATT TTGTATTCGA     540
CACCATGTGA GGCTGATAGT GATTACGCCA GAGTATGAAG TCAGTTGGAA ATTTGGGGAA     600
GGTGAATGGC CCCTGTGCGG AATTCTTTGC CTTAAATCAA ATCACTTCCA ACCATGTGCC     660
CCATTGAATG GTTGCATGAT TACAGCTATT GCTTCAGCAC TTGGTAGGCG TGAAGTTGAT     720
```

-continued

```
GTGCTTAATT ATCTGTGCAG GCCTAGCACT AACCACATTT TTGAGGAGCT TTGCCAAGGG      780
GGAGGCCTCA ACATGATGTA CTTAGCTGAA GCCTTTGAGG CTTTTGACAT TTGCGCTAAG      840
TGTGACATAA ATGGGGAAAT TGAGGTGATT AATCCACATG GCAAGTTTTC CGCTCTGTTT      900
GACATAACTA ATGAGCACAT AAGGCATGTT GAAAAGATAG GTAATGGCCC TCAGAGCATT      960
AAAGTAGATG AATTGCGAAA GGTCAAGCGA TCTGCCCTTG ATCTTCTTTC AATTAATGGG     1020
TCCAAGGTAA CCTACTTCCC AAGTTTTGAG CGGGCTGAAA AGTTGCAAGG GTGTCTGCTA     1080
GGAGGCCTAA CTGGTGTCAT AAGTGATGAG AAAGTCAGTG ATGCAAAGCC CTGCTTTTTG     1140
GTATATCAAC TACTGACATT AAGCCGAGGG AGCTAACTGT TGTGCTTTGG CACATTTGGA     1200
GCCCGGAAAA AGCCTTTTGT ACCAAGAGCT TTATTG                               1236
```

The nucleotide sequence of 140/94-6 (T3 +BM98–3F +F2) corresponds to SEQ. ID. No. 38 as follows:

```
GTCTAACTGG CGTTATAAGT GATGAGAAAT TCAGTGATGC AAAACCTTGG CTTTCTGGTA       60
TATCTACTAC AGATATTAAG CCAAGGGAAT TAACTGTTGT GCTTGGTACA TTTGGGGCTG      120
GGAAGAGTTT CTTGTACAAG AGTTTCATGA AAAGGTCTGA GGGTAAATTC GTAACCTTTG      180
TTTCTCCCAG ACGTGCTTTA GCAAATTCAA TCAAAAATGA TCTTGAAATG GATGATAGCT      240
GCAAAGTTGC CAAAGCAGGT AGGTCAAAGA AGGAAGGGTG GGATGTAGTA ACTTTTGAGG      300
TCTTCCTCAG AAAAGTTGCA GGATTGAAGG CTGGCCACTG TGTGATTTTT GATGAGGTCC      360
AGTTGTTTCC TCCTGGATAC ATCGATCTAT GCTTGCTTAT TATACGTAGT GATGCTTTCA      420
TTTCACTTGC CGGTGATCCA TGTCAAAGCA CATATGATTC GCAAAAGGAT CGGGCAATTT      480
TGGGCGCTGA GCAGAGTGAC ATACTTAGAA TGCTTGAGGG CAAAACGTAT AGGTATAACA      540
TAGAAAGCAG GAGGTTTGTG AACCCAATGT TCGAATCAAG ACTGCCATGT CACTTCAAAA      600
AGGGTTCGAT GACTGCCGCT TTCGCTGATT ATGCAATCTT CCATAATATG CATGACTTTC      660
TCCTGGCGAG GTCAAAAGGT CCTTTGGATG CCGTTTTGGT TTCCAGTTTT GAGGAGAAAA      720
AGATAGTCCA GTCCTACTTT GGAATGAAAC AGCTCACACT CACATTTGGT GAATCAACTG      780
GGTTGAATTT CAAAAATGGG GGAATTCTCA TATCACATGA TTCCTTTCAC ACAGATGATC      840
GGCGGTGGCT TACTGCTTTA TCTCGCTTCA GCCACAATTT GGATTTGGTG AACATTACAG      900
GTCTGAGGTG GAAAGTTTCC TCTCGCACTT TGCTGGCAAA CCCCTCTACC ATTTTTTAAC      960
AGCCAAAAGT GGGGAGAATG TCATACGAGA TTTGCTCCCA GGTGAGCCTA ACTTCTTCAG     1020
TGGCTTTAAC GTTAGCATTG GAAAGAATGA AGGTGTTAGG GAGGAGAAGT TATGTGGTGA     1080
CCCATGGTTA AAAGTCATGC TTTTCCTGGG TCAAGATGAG GATTGTGAAG TTGAAGAGAT     1140
GGAGTCAGAG TGCTCAAATG AAGAATGGTT TAAAACCCAC ATTCCCCTGA GTAATCTGGA     1200
GTCAACCAGG GCTAGGTGGG TGGGTAAAAT GGCCTTGAAA GAGTATCGGG AGGTGCGTTG     1260
TGGTTATGAA ATGACTCAAC AATTCTTTGA TGACAT                               1296
```

The nucleotide sequence of 140/94-64 (T7+R1) corresponds to SEQ. ID. No. 39 as follows:

```
ATGTTCACCA AATCCAAATT ATGGCTGAAG CGAGATAAAG CAGTAAGCCA CCGCCGATCA       60
TCTGTGTGAA AGGAATCATG TGATATGAGA ATTCCCCCAT TTTTGAAATT CAACCCAGTT      120
```

```
GATTCACCAA ATGTGAGTGT GAGCTGTTTC ATTCCAAAGT AGGACTGGAC TATCTTTTTC     180

TCCTCAAAAC TGGAAACCAA AACGGCATCC AAAGGACCTT TTGACCTCGC CAGGAGAAAG     240

TCATGCATAT TATGGAAGAT TGCATAATCA GCGAAAGCGG CAGTCATTGA GCCCTTTTG      300

AATTGACATG GCAGTCTTGA TTCGAACATT GGATTCACAA ACCTCCTGCT TTCAATGTTA     360

TACCTATACG TCTTGCCCTC AAGCAGTCTA AGTATGTCAC TCTGCTCAGC GCCCAAAATT     420

GCCCGATCCT TTTGCGAATC ATATGTGCTT TGACATGGAT CACCGGCAAG TGAAATGAAA     480

GCATCACTAC GTATAATAAG CAAGCATAGA TCGATGTATC CAGGAGGAAA CAACTGGACC     540

TCATCGAAAA TCACACAGTG GCCAGCCTTC AATCCTGCAA CTTTTCTGAG GAAAACCTCA     600

AAAGTTACTA CATCCCACCC TTCCTTCTTT GACCTACCTG CTTTAGCAAC TTTGCAGCTA     660

TCATCCATTT CAAGATCATT TTTGATTGAA TTTGCTAAAG CACGTCTGGG AGAAACAAAG     720

GTTACGAATT TACCCTCAGA CCTTTTCATG AAACTCTTGT ACAAGAAACT CTTCCCAGCC     780

CCAAATGTAC CAAGCACGAC AGTCAACTCC CTTGGCTTAA TATCAGTAGT AGATATACCA     840

GAAAGCCAAG GTTTTGCATC ACTGAACTTC TCATCACTTA AACGCCAGT TAGGCCCCCT      900

AGCAAAC                                                                907
```

The nucleotide sequence of 140-94-72 (T7+R1) corresponds to SEQ. ID. No. 40 as follows:

```
AGAATGCTTA TGCTGAGAAT GAGATGATTG CATTATTTTG CATCCGGCAC CATGTAAGGC      60

TTATAGTAAT AACACCGGAA TATGAAGTTA GTTGGAAATT TGGGGAAAGT GAGTGGCCCC     120

TATGTGGAAT TCTTTGCCTG AGGTCCAATC ACTTCCAACC ATGCGCCCCG CTGAATGGTT     180

GCATGATCAC GGCTATTGCT TCAGCACTTG GGAGGCGTGA GGTTGATGTG TTAAATTATC     240

TGTGTAGGCC TAGCACTAAT CACATCTTTG AGGAGCTGTG CCAGGGCGGA GGGCTTAATA     300

TGATGTACTT GGCTGAAGCT TTTGAGGCCT TTGACATTTG TGCAAAGTGC GACATAAATG     360

GGGAAATTGA GGTCATTAAC CCAAATGGCA AGATTTCCGC CTTGTTTGAT ATAACTAATG     420

AGCACATAAG GCATGTTGAG AAGATCAGCA ATGGCCCTCA GAGCATAAAA ATAGATGAGT     480

TGAGGAAGGT TAAGCGATCC CGCCTTGACC TTCTTTCAAT GAATGGGTCC AAAATAACCT     540

ATTTTCCAAA CTTTGAGCGG GCTGAAAAGT TGCAAGGGTG CTTGCTAGAG GGCCTGACTG     600

GTGTCATAAG TGATGAAAAG TTCAGTGATG CAAAACCTTG GCTTTCTGGT ATATCAACTG     660

CGGATATTAA GCCAAGAGAG CTAACTGTCG TGCTTGGCAC ATTTGGTGCT GGAAAGAGTT     720

TCTTGTATAA GAGTTTCATG AACAGATCTG AAGGAAAATT TGTAACTTTT GTTTCCCCTA     780

GGCGAGCTTT GGCCAATTCG ATCAAGAATG ATCTTGAAAT GGATGATGGC TGCAAAGTTG     840

CCAAAGCAGG CAAGTCAAAG AAGGAAGGGT GGGATGTGGT AACATTTGAG GTTTTCCTTA     900

GAAAAGTTTC TGGTTTGAAG GCTGGTCATT GTGTGATTTT CGATGAGGTT CAGTTGTTTC     960

CCCCTGGATA TATCGATCTA TGTTTACTTG TCATACGCAG TGATGCTTTT ATTTCACTTG    1020

CCGGTGATCC ATGCCAGAGC ACATATGATT CACAAAAGGA TCGGGCAATT TTGGGAGCTG    1080

AGCAGAGTGA CATACTCAGA TTGCTTGAAG GAAAGACGTA TAGGTACAAC ATAGAAAGCA    1140

GACGTTTTGT GAACCCAATG TTTGAATTTA GACTACCATG TCACTTCAAA AAAGGGTTCA    1200

ATGACTGCTG CCTTTGCTGA TTATGCAATC TT
```

Also encompassed by the present invention are fragments of the DNA molecules of the present invention. Suitable fragments capable of imparting RSP resistance to grape plants are constructed by using appropriate restriction sites, revealed by inspection of the DNA molecule's sequence, to: (i) insert an interposon (Felley et al., "Interposon Mutagenesis of Soil and Water Bacteria: A Family of DNA Fragments Designed for in vitro Insertion Mutagenesis of Gram-negative Bacteria," *Gene,* 52:147-15 (1987), which is hereby incorporated by reference) such that truncated forms of the RSP virus polypeptide or protein, that lack various amounts of the C-terminus, can be produced or (ii) delete various internal portions of the protein. Alternatively, the sequence can be used to amplify any portion of the coding region, such that it can be cloned into a vector supplying both transcription and translation start rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecules encoding the various *Rupestris* stem pitting associated virus proteins or polypeptides, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention also relates to RNA molecules which encode the various RSP virus proteins or polypeptides described above. The transcripts can be synthesized using the host cells of the present invention by any of the conventional techniques. The mRNA can be translated either in vitro or in vivo. Cell-free systems typically include wheat-germ or reticulocyte extracts. In vivo translation can be effected, for example, by microinjection into frog oocytes.

One aspect of the present invention involves using one or more of the above DNA molecules encoding the various proteins or polypeptides of a RSP virus to transform grape plants in order to impart RSP resistance to the plants. The mechanism by which resistance is imparted in not known. In one hypothetical mechanism, the transformed plant can express the coat protein or polypeptide, and, when the transformed plant is inoculated by a RSP virus, such as RSPaV-1, the expressed coat protein or polypeptide surrounds the virus, thereby preventing translation of the viral DNA.

In this aspect of the present invention, the subject DNA molecule incorporated in the plant can be constitutively expressed. Alternatively, expression can be regulated by a promoter which is activated by the presence of RSP virus. Suitable promoters for these purposes include those from genes expressed in response to RSP virus infiltration.

The isolated DNA molecules of the present invention can be utilized to impart RSP virus resistance for a wide variety of grapevine plants. The DNA molecules are particularly well suited to imparting resistance to Vitis scion or rootstock cultivars. Scion cultivars which can be protected include those commonly referred to as Table or Raisin Grapes, such as Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono, Chardonnay, Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, and Zinfandel. Rootstock cultivars which can be protected include Couderc 1202, Couderc 1613, Couderc 1616, Couderc 3309, Dog Ridge, Foex 33 EM, Freedom, Ganzin 1 (A×R#1), Harmony, Kober 5BB, LN33, Millardet & de Grasset 41B, Millardet & de Grasset 420A, Millardet & de Grasset 101-14, Oppenheim 4 (SO4), Paulsen 775, Paulsen 1045, Paulsen 1103, Richter 99, Richter 110, Riparia Gloire, Ruggeri 225, Saint-George, Salt Creek, Teleki 5A, *Vitis rupestris* Constantia, *Vitis california*, and *Vitis girdiana*.

Plant tissue suitable for transformation include leaf tissue, root tissue, meristems, zygotic and somatic embryos, and anthers. It is particularly preferred to utilize embryos obtained from anther cultures.

The expression system of the present invention can be used to transform virtually any plant tissue under suitable conditions. Tissue cells transformed in accordance with the present invention can be grown in vitro in a suitable medium to impart RSPaV resistance. Transformed cells can be regenerated into whole plants such that the protein or polypeptide imparts resistance to RSPaV in the intact transgenic plants. In either case, the plant cells transformed with the recombinant DNA expression system of the present invention are grown and caused to express that DNA molecule to produce one of the above-described RSPaV proteins or polypeptides and, thus, to impart RSPaV resistance.

In producing transgenic plants, the DNA construct in a vector described above can be microinjected directly into plant cells by use of micropipettes to transfer mechanically the recombinant DNA. Crossway, *Mol. Gen. Genetics*, 202:179–85 (1985), which is hereby incorporated by reference. The genetic material may also be transferred into the plant cell using polyethylene glycol. Krens, et al., *Nature*, 296:72–74 (1982), which is hereby incorporated by reference.

One technique of transforming plants with the DNA molecules in accordance with the present invention is by contacting the tissue of such plants with an inoculum of a bacteria transformed with a vector comprising a gene in accordance with the present invention which imparts RSPaV resistance. Generally, this procedure involves inoculating the plant tissue with a suspension of bacteria and incubating the tissue for 48 to 72 hours on regeneration medium without antibiotics at 25–28° C.

Bacteria from the genus Agrobacterium can be utilized to transform plant cells. Suitable species of such bacterium include *Agrobacterium tumefaciens* and *Agrobacterium rhizogenes*. *Agrobacterium tumefaciens* (e.g., strains C58, LBA4404, or EHA105) is particularly useful due to its well-known ability to transform plants.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science*, 237:1176–83 (1987), which is hereby incorporated by reference.

After transformation, the transformed plant cells must be regenerated.

Plant regeneration from cultured protoplasts is described in Evans et al., *Handbook of Plant Cell Cultures, Vol. 1*: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure so that the DNA construct is present in the resulting plants. Alternatively, transgenic seeds are recovered from the transgenic plants. These seeds can then be planted in the soil and cultivated using conventional procedures to produce transgenic plants.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," Plant Cell Reports, 14:6–12 (1995) ("Emerschad (1995)"), which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Once a grape plant tissue is transformed in accordance with the present invention, it is regenerated to form a transgenic grape plant. Generally, regeneration is accomplished by culturing transformed tissue on medium containing the appropriate growth regulators and nutrients to allow for the initiation of shoot meristems. Appropriate antibiotics are added to the regeneration medium to inhibit the growth of Agrobacterium and to select for the development of transformed cells. Following shoot initiation, shoots are allowed to develop tissue culture and are screened for marker gene activity.

The DNA molecules of the present invention can be made capable of transcription to a messenger RNA that does not translate to the protein. This is known as RNA-mediated resistance. When a Vitis scion or rootstock cultivar is transformed with such a DNA molecule, the DNA molecule can be transcribed under conditions effective to maintain the messenger RNA in the plant cell at low level density readings. Density readings of between 15 and 50 using a Hewlet ScanJet and Image Analysis Program are preferred.

A portion of one or more DNA molecules of the present invention as well as other DNA molecules can be used in a transgenic grape plant in accordance with U.S. patent application Ser. No. 09/025,635, which is hereby incorporated herein by reference.

The RSPaV protein or polypeptide can also be used to raise antibodies or binding portions thereof or probes. The antibodies can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature*, 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents. (See Milstein and Kohler, *Eur. J. Immunol.*, 6:511 (1976), which is hereby incorporated by reference.) This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbital 150 mg/Kg IV. This and other procedures for raising polyclonal antibodies are disclosed in Harlow et. al., editors, *Antibodies: A Laboratory Manual* (1988), which is hereby incorporated by reference.

In addition to utilizing whole antibodies, binding portions of such antibodies can be used. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice,* New York: Academic Press, pp. 98–118 (1983), which is hereby incorporated by reference.

The present invention also relates to probes found either in nature or prepared synthetically by recombinant DNA procedures or other biological procedures. Suitable probes are molecules that bind to RSP viral antigens identified by the polyclonal antibodies of the present invention or bind to the nucleic acid of RSPaV. Such probes can be, for example, proteins, peptides, lectins, or nucleic acids.

The antibodies or binding portions thereof or probes can be administered to RSPaV infected scion cultivars or rootstock cultivars. Alternatively, at least the binding portions of these antibodies can be sequenced, and the encoding DNA synthesized. The encoding DNA molecule can be used to transform plants together with a promoter which causes expression of the encoded antibody when the plant is infected by an RSPaV. In either case, the antibody or binding portion thereof or probe will bind to the virus and help prevent the usual stem pitting response.

Antibodies raised against the proteins or polypeptides of the present invention or binding portions of these antibodies can be utilized in a method for detection of RSPaV in a sample of tissue, such as tissue from a grape scion or rootstock. Antibodies or binding portions thereof suitable for use in the detection method include those raised against a replicase, proteins or polypeptides of the triple gene block, or a coat protein or polypeptide in accordance with the present invention. Any reaction of the sample with the antibody is detected using an assay system which indicates the presence of RSPaV in the sample. A variety of assay systems can be employed, such as enzyme-linked immunosorbent assays, radioimmunoassays, gel diffusion precipitin reaction assays, immunodiffusion assays, agglutination assays, fluorescent immunoassays, protein A immunoassays, or immunoelectrophoresis assays.

Alternatively, the RSPaV can be detected in such a sample using the DNA molecules of the present, RNA molecules of the present invention, or DNA or RNA fragments thereof, as probes in nucleic acid hybridization assays for detecting the presence of complementary virus DNA or RNA in the various tissue samples described above. The nucleotide sequence is provided as a probe in a nucleic acid hybridization assay or a gene amplification detection procedure (e.g., using a polymerase chain reaction procedure). The nucleic acid probes of the present invention may be used in any nucleic acid hybridization assay system known in the art, including, but not limited to, Southern blots (Southern, E. M., "Detection of Specific Sequences Among DNA Fragments Separated by Gel Electrophoresis," *J. Mol. Biol.*, 98:503–17 (1975), which is hereby incorporated by reference), Northern blots (Thomas, P. S., "Hybridization of Denatured RNA and Small DNA Fragments Transferred to Nitrocellulose," *Proc. Nat'l Acad. Sci. USA*, 77:5201–05 (1980), which is hereby incorporated by reference), and Colony blots (Grunstein, M., et al., "Colony Hybridization: A Method for the Isolation of Cloned cDNAs that Contain a Specific Gene," *Proc. Nat'l Acad. Sci. USA*, 72:3961–65 (1975), which is hereby incorporated by reference). Alternatively, the isolated DNA molecules of the present invention or RNA transcripts thereof can be used in a gene amplification detection procedure (e.g., a polymerase chain reaction). Erlich, H. A., et. al., "Recent Advances in the Polymerase Chain Reaction," *Science* 252:1643–51 (1991), which is hereby incorporated by reference. Any reaction with the probe is detected so that the presence of RSP virus in the sample is indicated. Such detection is facilitated by providing the DNA molecule of the present invention with a label. Suitable labels include a radioactive compound, a fluorescent compound, a chemiluminescent compound, an enzymatic compound, or other equivalent nucleic acid labels.

Depending upon the desired scope of detection, it is possible to utilize probes having nucleotide sequences that correspond with conserved or variable regions of the ORF or UTR. For example, to distinguish RSPaV from other related viruses (as described herein), it is desirable to use probes which contain nucleotide sequences that correspond to sequences more highly conserved among all RSPaV strains. Also, to distinguish between different RSPaV strains (e.g., RSPaV-1, RSP47-4, RSP158), it is desirable to utilize probes containing nucleotide sequences that correspond to sequences less highly conserved among the RSP virus strains.

Nucleic acid (DNA or RNA) probes of the present invention will hybridize to complementary RSPaV-1 nucleic acid under stringent conditions. Less stringent conditions may also be selected. Generally, stringent conditions are selected to be about 50° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ is dependent upon the solution conditions and the base composition of the probe, and may be calculated using the following equation:

$$T_m = 79.8° C. + (18.5 \times \text{Log}[\text{Na+}])$$
$$+ (58.4° C. \times \% \ [G + C])$$
$$- (820 / \# \text{bp in duplex})$$
$$- (0.5 \times \% \text{ formamide})$$

Nonspecific binding may also be controlled using any one of a number of known techniques such as, for example, blocking the membrane with protein-containing solutions, addition of heterologous RNA, DNA, and SDS to the hybridization buffer, and treatment with RNase. Generally, suitable stringent conditions for nucleic acid hybridization assays or gene amplification detection procedures are as set forth above. More or less stringent conditions may also be selected.

The development of a rapid detection method for RSP is a major breakthrough, because the only detection method now available is through inoculation of St. George grape indicators, which takes two to three years to develop symptoms. A serological or nucleic acid based detection tests developed for RSP will take only 1 to 2 days and it is less expensive. The woody indicator test on St. George costs $250 per sample, while a serological or nucleic acid based test would cost $30–50 per sample. Moreover, the rapid tests will speed up the introduction of grape imports into the US from the current three years to about six months. These applications will be valuable wherever grapes are grown. Since RSP is part of the rugose wood complex, development of rapid detection methods will be invaluable in determining the significance of RSP in the rugose wood complex. This will allow an investigator to determine whether RSP alone can cause the rugose wood complex or if other components are needed. In addition, these rapid detection methods are very useful to evaluate the resistance of transgenic plants to *Rupestris* stem pitting associated virus.

EXAMPLES

The following examples are provided to illustrate embodiments of the present invention but are by no means intended to limit its scope.

Example 1—Grapevine Materials for dsRNA Analysis

Samples from 15 accessions that induced pitting on graft-inoculated St. George were collected from the National Grapevine Germplasm Repository of the USDA Plant Genetic Resources Unit (PGRU) at Geneva and used for dsRNA analysis. Positive controls used included Thompson Seedless (RSP105) (Golino, "The Davis Grapevine Virus Collection," *Am. J. Enology Viticulture*, 43:200–05 (1992), which is hereby incorporated by reference) from the FPMS, University of California (Davis) and Pinot Noir (SVP1186-09A2), which was kindly provided by Dr. R. Johnson of Center for Plant Health, Agriculture Canada, Sidney, British Columbia. Negative controls as judged by indexing on St. George included Freedom from the PGRU at Geneva, New York, and Verduzzo 233A. The latter was kindly provided by Dr. P. Silvano of the Sezione di Fitovirologia, ERSA Servizio Chimico-Agrario e della Certificazione, Pozzuolo del Friuh (UD), Italy.

Example 2—Grapevine Materials for RT-PCR

Dormant cuttings of 138 grapevine selections were collected from USA, Canada, Italy, and Portugal over three years. Samples included *Vitis vinifera* cultivars, hybrids, *V. riparia*, and rootstocks. 117 grapevine selections were indexed on St. George for RSP and other RW diseases. Pinot noir (1186-9A2) from Agriculture Canada, Center for Plant Health (Sidney, Canada) and Thompson seedless (RSP105) from University of California (Davis) were included as positive controls. Sauvignon blanc, generated from shoot tip tissue culture and tested free of viruses and viroids was provided by Dr. J. Semancik (University of California at Riverside) and used as a healthy control. In addition, six seedlings of five Vitis species were also included as negative controls.

Example 3—dsRNA Isolation and Analysis

Methods for isolating dsRNA were described by Hu et al., "Characterization of Closterovirus-like Particles Associated with Grapevine Leafroll Disease," *J. Phytopathology*, 128:1–14 (1990), which is hereby incorporated by reference, except that 1 X STE with 15% ethanol (instead of 16.5%) was used to wash CF-11 cellulose columns prior to elution of dsRNAs. The dsRNAs were isolated from leaves, petioles, and the phloem tissue of dormant canes, electrophoresed on 1% agarose or low melting temperature agarose gels, and analyzed by staining with ethidium bromide (EtBr). Hind EII digested lambda DNA was used as markers to estimate the sizes of the dsRNA molecules.

Example 4—cDNA Synthesis and Cloning

The extremely low yield of dsRNA and the limited quantity of RSP-infected grape materials precluded the use of a single RSP-infected grapevine accession as the source of dsRNA for cloning purpose. Therefore, dsRNA preparations from Colobel 257, Ravat 34, Couderc 28–112, and Seyval were pooled and used as templates for cDNA synthesis. In order to get pure templates for cloning, dsRNA bands were excised from low melting temperature agarose gels after electrophoresis and recovered by extraction with phenol and chloroform (Sambrook et al., *Molecular Cloning: A Laboratory Manual*, 2nd ed., Cold Spring Harbor Laboratory Press, Cold Spring Harbor, N.Y. (1989), which is hereby incorporated by reference). The same recovery procedure was repeated once more. The purified dsRNA was denatured with 20 mM methyl mercuric hydroxide and cDNAs were synthesized using slightly modified methods of Jelkmann et al., "Cloning of Four Viruses from Small Quantities of Double-Stranded RNA," *Phytopathology*, 79:1250–53 (1989), which is incorporated herein be reference. The cDNA fragments were first blunt-ended with T4 DNA polymerase at 12° C. T4 DNA ligase was used to add EcoR I adapters to both ends of the cDNAs. Subsequently, the cDNA molecules with cohesive ends were ligated to EcoR I-prepared arms of lambda ZAP II. Finally, the resulting recombinant phages were packed into Gigapack II packaging extract following manufacturer's instructions (Stratagene, La Jolla, Calif.).

Example 5—Identification of cDNA Clones Specific to the dsRNA

Plaque hybridization was used to screen cDNA clones by transferring recombinant cDNA plaques to nylon membranes and hybridizing to $^{32}$P-labeled first-strand cDNA probes generated from the dsRNA according to manufacturer's recommendations (Du Pont, 1987). Clones with strong hybridization signals were converted into pBluescript SK through in vivo excision (Stratagene, 1991). After digestion of the resulting plasmids with EcoR I, 20 clones were selected and further analyzed in Southern hybridization with radio labeled first strand cDNA probes synthesized from the dsRNA. The specificity of two selected clones to the dsRNA was confirmed by Northern analysis using $^{32}$P labeled inserts of the two clones.

Example 6—Bridging Gaps Between Clones

To bridge the gap between clones RSP3 and RSP94, a pair of specific primers were used in RT-PCR to generate cDNA fragments from the dsRNA. RSP3-RSP94 primer 1 (sense, nt 3629–3648) has a nucleotide sequence corresponding to SEQ. ID. No. 41 as follows:

```
GCTTCAGCAC TTGGAAGGCG                               20
```

RSP3-RSP94 primer 2 (antisense, nt 4350–4366) has a nucleotide sequence corresponding to SEQ. ID. No. 42 as follows:

```
CACACAGTGG CCAGCCT                                  17
```

After gel electrophoresis, PCR amplified cDNA bands were excised from gels and recovered with the phenol/chloroform method (Sambrook et al., *Molecular Cloning: A Laboratory Manual*, 2nd ed., Cold Spring Harbor Laboratory Press, Cold Spring Harbor, N.Y. (1989), which is hereby incorporated by reference).

The same strategy was employed to bridge the gap between clones RSP94 and RSP95. RSP94–RSP95 primer 1 (sense, nt 5272–5291) has a nucleotide sequence corresponding to SEQ. ID. No. 43 as follows:

```
GGAGGTGCGT TGTGGTTATG                               20
```

RSP94–RSP95 primer 2 (antisense, nt 6791–6808) has a nucleotide sequence corresponding to SEQ. ID. No. 44 as follows:

```
CCCTGGCACT GCACACCC                                 17
```

Example 7—Obtaining Nucleotide Sequences on Both Termini of RSPaV-1 Genome

To obtain the terminal 3' end sequences, a primer (sense, nt 8193–8210) having a nucleotide sequence corresponding to SEQ. ID. No. 45 as follows:

```
GGAGGTGACC ACATTACG                                 18
``` and a (dT) 18 primer were used in RT-PCR to amplify cDNA from the dsRNA. Resulting PCR products were cloned into TA vector pCRII (Invitrogen) and sequenced. This approach was based on the assumption that the RSP associated dsRNA contained a poly (A) tail. For the terminal 5' end, the dsRNA was first tagged with poly (A) using yeast Poly (A) polymerase (USB) (Pappu et al., "Nucleotide Sequence and Organization of Eight 3' Open Reading Frames of the Citrus tristeza Closterovirus Genome," *Virology* 199:35–46 (1994), which is hereby incorporated by reference) and then used as templates to generate cDNA fragments by RT-PCR using (dT) 18 primer and primer (antisense, nt 429–449) having a nucleotide sequence corresponding to SEQ. ID. NO. 46 as follows:

CATCACGACT TGTCACAAAC C                    21

Example 8—Nucleotide Sequencing

CsCl or alkaline/PEG (polyethylene glycol) purified plasmids (Sambrook et al., *Molecular Cloning: A Laboratory Manual,* 2nd ed., Cold Spring Harbor Laboratory Press, Cold Spring Harbor, N.Y. (1989), which is hereby incorporated by reference; Applied Biosystems, Inc.) and RT-PCR amplified cDNA fragments were sequenced for completion on both strands. Nucleotide sequencing was done manually with Sequenase version 2.0 kit (USB) or automatically on ABI 373 automated sequencer with Taq DyeDeoxy™ terminator cycle sequencing kit (Applied Biosystems, Inc.). Vector primers (T3, T7, M13 Forward, and M13 Reverse) were used in initial sequencing and sequences were completed by primer walking strategy.

Example 9—Reverse Transcription-Polymerase Chain Reaction (RT-PCR)

Two pairs of primers were designed for RT-PCR: (1) RSP95F1 and RSP95R1; and (2) RSP149F1 and RSP149R1. Primer RSP95F1, an antisense strand primer, has a nucleotide sequence corresponding to SEQ. ID. NO. 47 as follows:

TGGGCCTCCA CTTCTTC                         17

Primer RSP95R1, a sense strand primer, has a nucleotide sequence corresponding to SEQ. ID. No. 48 as follows:

GGGGTTGCCT GAAGAT                          16

Primer RSP149F1, an antisense strand primer, has a nucleotide sequence corresponding to SEQ. ID. No. 49 as follows:

ACACCTGCTG TGAAAGC                         17

Primer RSP149R1, a sense strand primer, has a nucleotide sequence corresponding to SEQ. ID. No. 50 as follows:

GGCCAAGGTT CAGTTTG                         17

RSP95F1/R1 were used in RT-PCR to test samples collected in 1994. RSP149R1/F1, alone or together with RSP95F1/R1, were used to test samples collected in 1995 and 1996. To avoid bias in the judgment of RT-PCR results, blind tests were conducted for samples from Canada in 1995 and 1996. The indexing results of these samples were kept untold until the RT-PCR tests were complete.

dsRNAs were denatured with methylmercuric hydroxide (CH4HgOH) and reverse transcribed into cDNAs with Moloney murine leukemia virus (MMLV) or Avian Myeloblastosis Virus (AMV) reverse transcriptases (Promega) at 42° C. for 1 to 3 h. Five of 20 µl of the RT reactions were added to PCR mix and amplified in thermal cycler (HYBAID OmniGene, National Labnet Company) with Taq DNA polymerase (buffer B, Promega) using the following parameters: initial denaturation at 94° C. for 5 min, 40 cycles of amplification at 94° C. for 45 s, 52° C. for 1 min, and 72° C. for 1 min, and a final extension at 72° C. for 10 min. PCR products were analyzed by electrophoresis on 1% agarose gels containing ethidium bromide. Hae III digested Phix 174 fragments were used as molecular weight markers.

Example 10—Southern Blot

DNA fragments amplified by PCR from cDNA clone RSP149 with primers RSP149F1/R1 were labeled with 32P by random priming and used as probes. Products of RT-PCR of randomly selected grapevines including 26 positives and 6 negatives by RT-PCR were electrophoresed on an 0.8% agarose gel, transferred to nylon membranes, and hybridized to the probes following manufacturer's instructions (Du Pont).

Example 11—Computer Assisted Analysis of Sequences and Genome Structure of RSPaV-1

Sequences were assembled with SeqMan program and potential open reading frames were generated with MapDraw program (DNASTAR, Madison, Wis.). BLAST program of the NCBI (the National Center for Biotechnology Information) was used to search for homologies in DNA and protein databases. Clustal analysis (with identity weight table) of MegAlign (DNASTAR) was employed to reveal sequence similarities between the putative proteins of RSPaV-1 and the analogous proteins of ASPV (Jelkmann, "Nucleotide Sequences of Apple Stem Pitting Virus and of the Coat Protein of a Similar Virus from Pear Associated with Vein Yellows Disease and Their Relationship with Potex- and Carlaviruses," *J. General Virology,* 75:1535–42 (1994), which is hereby incorporated by reference) and PVM (Zavriev et al., "Complete Nucleotide Sequence of Genomic RNA of the Potato M-Virus," *Molecular Biology* (*Mosk.*) 25:761–69 (1991), which is hereby incorporated by reference). In addition, nucleotide sequences of the untranslated regions (UTR) of these three viruses were also compared using MagAlign, as shown in FIGS. 6A and 6B.

Example 12—Consistent Association of a High Molecular Weight dsRNA with RSP

Figure 2A:
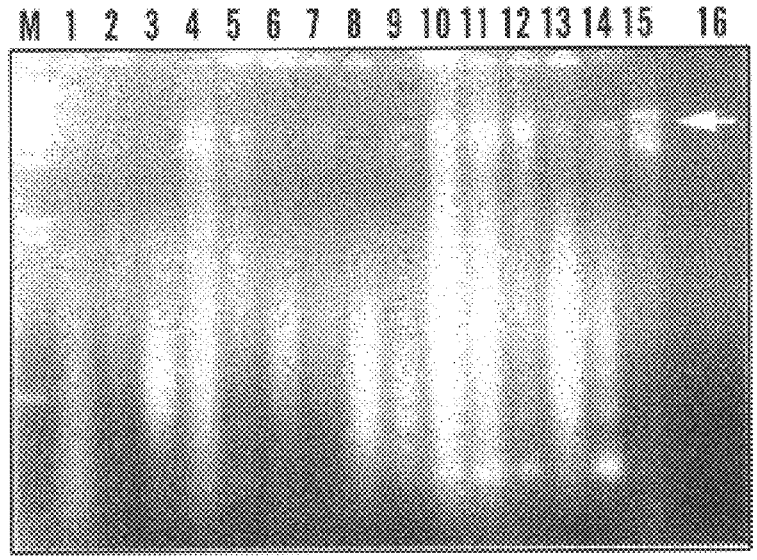
FIGS. 2A and 2B are photographs which respectively display the results of dsRNA analysis and Northern hybridization for dsRNA. Together the photographs may be used to correlate the dsRNA analysis of FIG. 2A with the Northern hybridization (for dsRNA isolated from grapevines indexed positive for *Rupestris* stem pitting (RSP)) of FIG. 2B. M. Hind III digested lambda DNA maker: lane 1, Aminia; lane 2, Bertille Seyve 5563; lane 3, Canandaigua; lane 4, Colobel 257; lane 5, Couderc 28–112; lane 6, Freedom; lane 7, Grande Glabre; lane 8, M 344-1; lane 9, Joffre; lane 10, Ravat 34; lane 11, Seyval; lane 12, Seyve Vinard 14–287; lane 13, Verdelet; lane 14, Pinot Noir (positive control); lane 15, Verduzzo 233A (negative control for RSP as judged by indexing on St. George); lane 16, insert of clone RSP149. Arrows indicate the position of the 8.7 kb dsRNA. With respect to lane 15 of FIG. 2A, the two dsRNA bands are larger or smaller than the 8.7 kb dsRNA associated with RSP and they did not hybridize with the RSP specific probe in Northern analysis. Thus, they are not specific to RSP.
Figure 2B:
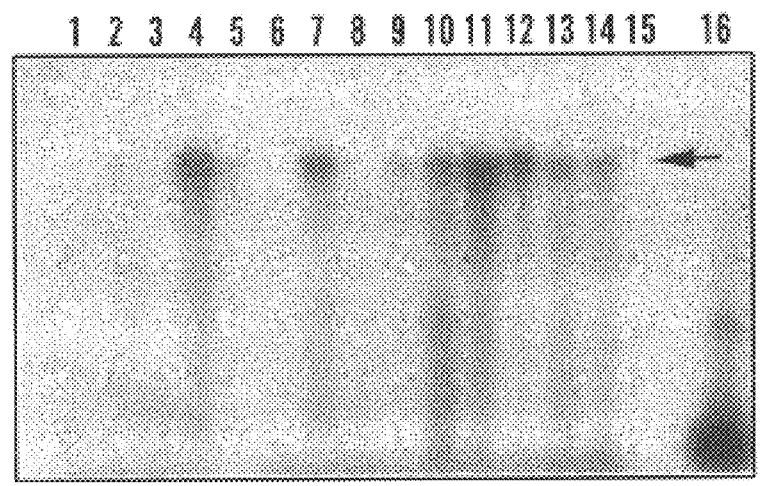

The 15 grapevine accessions used in this study were previously indexed on St. George where 12 accessions induced typical RSP symptoms (i.e., a narrow strip of small pits below the inoculum bud). FIG. 1A illustrates these typical RSP symptoms. A good correlation was found between the presence of the specific dsRNA and the indexing results on St. George. As shown in FIG. 2A and recorded in Table 1 below, twelve grapevine accessions with typical RSP symptoms revealed a dsRNA of ca. 8.7 kb with gel electrophoresis. In addition, a smaller dsRNA of about 6.6 kb was observed in Colobel 257 and Seyval. In contrast, although Aminia and Canandaigua elicited deep pits and grooves around the woody cylinder of St. George, they did not reveal visible dsRNA of expected size in repeated experiments. Freedom, which indexed negative for RSP on St. George, did not reveal visible dsRNA. Although two dsRNA bands were observed in Verduzzo 233A (which was indexed free of RSP on St. George), they were not specific to RSP based on the fact that they were larger or smaller than the 8.7 kb dsRNA associated with RSP (FIG. 2A) and that they did not hybridize to the RSP-specific probe in Northern analysis (FIG. 2B). In addition, the two dsRNA species isolated from Verduzzo 233A were not observed in other healthy grapevines such as Cabernet Franc and LN 33.

TABLE 1

| Accessions and Parentage | St. George Indicator | dsRNA | Northern |
|---|---|---|---|
| Aminia (Carter X Black Hamburg) | + | − | − |
| Bertille Seyve 3408 (BS 872 X Seibel 5410) | + | + | + |
| Bertille Seyve 5563 (Seibel 6905 X BS 3445) | + | + | + |
| Canandaigua (V. labrusca X V. vinifera) | + | − | − |
| Colobel 257 (Seibel 6150 X Seibel 5455) | + | + | + |
| Couderc 28-112 (Emily X V. rupestris) | + | + | + |
| Freedom (Couderc 1613 X Dog Ridge) | − | − | − |
| Grande Glabre (V. riparia) | + | + | + |
| Ill 344-1 (BS 2667 X Seibel 6905) | + | +† | −† |
| Joffre (V. vinifera X V. riparia X V. rupestris) | + | + | + |
| Ravat 34 (Berlandieri X Chardonnay) | + | + | + |
| Seyval (Seibel 4995 X Seibel 4986) | + | + | + |
| Seyve Villard 14-287 (V. labrusca X V. rupestris X V. aestiv X V. cinerea X V. vinifera) | + | + | + |
| Seyve Villard 3160 (Seibel 5163 X Seibel 2049) | + | + | + |
| Verdelet (Seibel 5455 X Seibel 4938) | + | + | + |
| Controls | | | |
| Pinot Noir (V. vinifera) | + | + | + |
| Thompson seedless (V. vinifera) | + | NT | + |
| Verduzzo 233A | − | −‡ | − |

Symbols:
*Probe used was insert from cDNA clone RSP149.
†A faint dsRNA band could be observed on the gel after electrophoresis but no hybridization signal could be seen in Northern analysis.
‡Although two dsRNA bands were observed in Verduzzo 233A, they were not specific to RSP, because they were either larger or smaller than the RSP-associated 8.7 kbp dsRNA and they did not hybridize to the probe in Northern analysis.

The yield of dsRNA was low and varied significantly among different accessions. When a comparable amount of phloem tissue (14 g for Bertille Seyve 5563 and Couderc 28–112; 18.5 g for the others) was used to isolate dsRNA, Colobel 257, Seyval, Ravat 34, Grande Glabre, and Seyve Villard 14–287 displayed strong dsRNA bands, while Bertille Seyve 5563, Couderc 28–112, Joffre, and Verdelet showed weak bands after staining with EtBr, as shown in FIG. 2A. Bertille Seyve 3408 and Seyve Villard 3160 were analyzed in separate experiments and dsRNA bands of the same size were observed.

Example 13—Selection and Specificity of cDNA Clones

A total of 182 clones were selected after plaque hybridization. Eighty clones with strong hybridization signals were subcloned into pBluescript SK through in vivo excision. Resulting plasmids were shown to have inserts ranging from 0.3 to 3.0 kb. A total of 20 clones with inserts of ca. 0.8 kb or larger were selected. Southern analysis of these 20 clones to radio labeled first strand cDNA probes derived from the dsRNA resulted in 15 clones with strong hybridization signals. Several of these clones were used to determine the genome sequence of the dsRNA: RSP3, RSP28, RSP94, RSP140, RSP95, and TA5. Another clone (RSP149), which was 97% similar in nucleotide sequence to RSP95, was used as one of the two probes in Northern hybridization.

Northern hybridization was employed to confirm the specific relationship of clones RSP95 and RSP149 to the isolated dsRNA. These two clones gave the strongest reaction in Southern analysis described above. Initial experiments showed that RSP95 insert hybridized with the dsRNA isolated from three accessions (Colobel 257, Seyval, and Ravat 34), from which the template dsRNAs used in cDNA synthesis were isolated. As shown in FIG. 2B and indicated in Table 1, use of RSP149 insert as the probe showed that this clone hybridized with the dsRNA of ca. 8.7 kb isolated from RSP infected grapevines. Furthermore, the intensity of hybridization signals corresponded to that of the dsRNA bands observed on agarose gels stained with EtBr. Colobel 257, Seyval, Ravat 34, Grande Glabre, and Serve Villard 14-287 reacted strongly; Bertille Seyve 5563, Couderc 28-112, Joffre, and Verdelet had weak hybridization signals. The result for Ill 344-1 was not conclusive. Aminia and Canandaigua did not show visible dsRNAs or hybridization in Northern analysis. Bertille Seyve 3408, which was tested in a separate experiment, did show a ca. 8.7 kb dsRNA which hybridized to the probe from RSP149. Freedom and Verduzzo 233A, which had indexed negative for RSP on St. George, were also negative in Northern blot.

Example 14

Nucleotide Sequence and Genome Structure of RSPaV-1

Figures 3A, 3B:
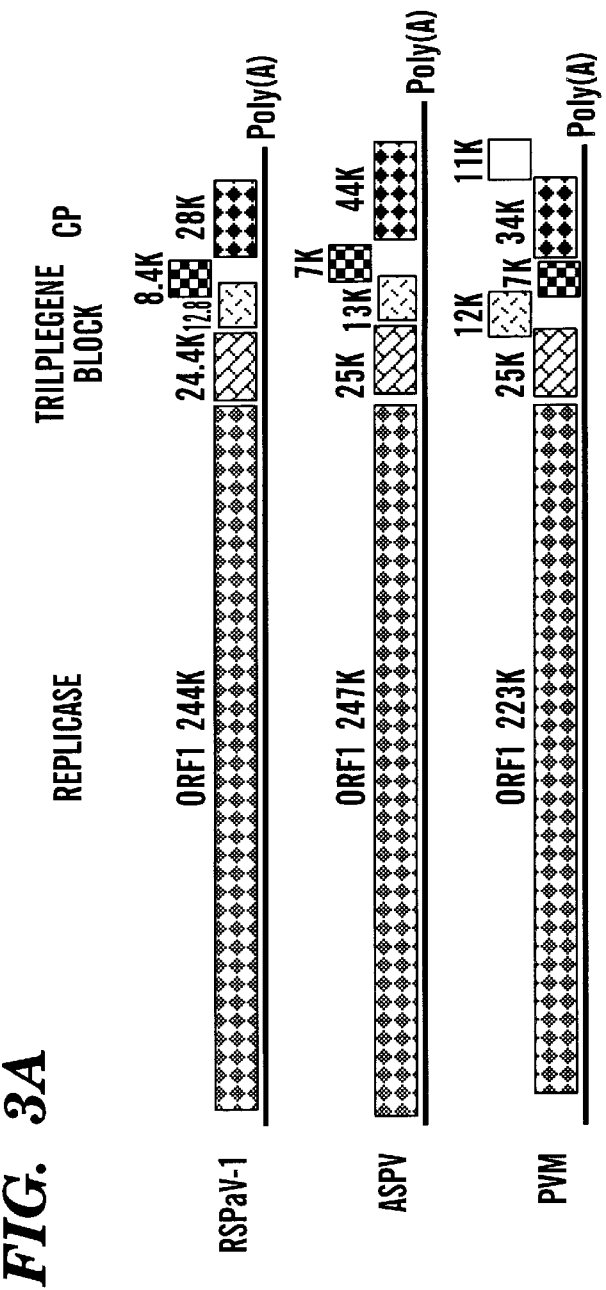
FIG. 3A is an illustration which depicts the strategy for obtaining the complete nucleotide sequence of RSPaV-1. The overlapping regions of the nucleotide sequences of the sequenced clones and RT-PCR-amplified cDNA fragments are as follows: 52–375 for RSPA/RSP28; 677–1474 for RSP28/RSP3; 3673–3766 for RSP3/RSPB; 4009–4320 for RSPB/RSP94; 5377–5750 for RSP94/RSPC; 5794–6537 for RSPC/RSP95; 6579–6771 for RSPC/RSP140; and 8193–8632 for RSP140/TA5.
FIG. 3B is an illustration which comparatively depicts the genome structures of RSPaV-1, ASPV, PVM, and PVX. Boxes with the same patterns represent the comparable ORFS.

Six cDNA clones and three RT-PCR amplified cDNA fragments (identified as RSPA, RSPB, and RSPC) were sequenced on both strands and used to obtain the complete nucleotide sequence of a viral agent, which is shown in FIG. 3A. The genome of RSPaV-1 consisted of 8726 nts excluding a poly (A) tail on the 3' end. The sequence of RSPA indicated that the 5' first base of the RSPaV-1 genome appeared to be a cytosine (C). Clone TA5, which represented the 3' end of the RSPaV-1 genome, contained a stretch of adenines (A) preceded by a cytosine.

MapDraw analysis, shown at FIG. 3B, indicated that the genome of RSPaV-1 had five potential ORFs on its positive strand, while no ORFs were observed on the negative strand (data not shown). ORF1 (nt 62 to 6547 of SEQ. ID. No. 1) has a nucleotide sequence corresponding to SEQ. ID. NO. 2. ORF1 believed to encode a protein or polypeptide having a molecular weight of about 244 kDa and an amino acid sequence corresponding to SEQ. ID. No. 3. According to Lutcke et al., "Selection of AUG Initiation Codons Differs in Plants and Animals," Eur. Mol. Biol. J., 6:43–48 (1987), which is hereby incorporated by reference, the start codon of ORF1 was in a favorable context: GCAAUGGC, where the "GC" after the start codon is important for initiating translation in a plant system. ORF2 (nt 6578 to 7243 of SEQ. ID. No. 1) has a nucleotide sequence corresponding to SEQ. ID. No. 4. ORF2 is believed to encode a protein or polypeptide having a molecular weight of about 24.4 kDa and an amino acid sequence corresponding to SEQ. ID. NO. 5. The first two ORFs were separated by an intergenic region of 30 nts. ORF3 (nt 7245 to 7598 of SEQ. ID. NO. 1) has a nucleotide sequence corresponding to SEQ. ID. No. 6. ORF3 is believed to encode a protein or polypeptide having a molecular weight of about 12.8 kDa and an amino acid sequence corresponding to SEQ. ID. NO. 7. ORF4 (nt 7519 to 7761 of SEQ. ID. NO. 1), which overlapped with ORF3 by 80 nts, has a nucleotide sequence corresponding to SEQ. ID. No. 8. ORF3 is believed to encode a protein or polypeptide having a molecular weight of about 8.4 kDa and an amino acid sequence corresponding to SEQ. ID. No. 9. Nine nucleotides downstream of ORF4 was the start of ORF5 (nt 7771 to 8550 of SEQ. ID. No. 1), which has a nucleotide sequence corresponding to SEQ. ID. No. 10. ORF5 is believed to encode a protein or polypeptide having a molecular weight of about 28 kDa and an amino acid sequence corresponding to SEQ. ID. No. 11. Downstream of ORF5 was the 3' end LJTR of 176 nts. Although computer assisted analysis indicated that two shorter ORFs may exist as alternatives to ORF1 and ORF5, neither of them were in good contexts for translation initiation.

Example 15

Comparison of the RSPaV-1 Genome with ASPV and PVM Carlavirus Genomes

The arrangement of the ORFs and the amino acid sequences of RSPaV-1 showed similarities to those of PVX (Skryabin et al., "The Nucleotide Sequence of Potato Virus X RNA," *Nucleic Acids Res.* 16: 10929–30 (1988), which is hereby incorporated by reference), PVM (Zavriev et al., "Complete Nucleotide Sequence of Genomic RNA of the Potato M-Virus," *Molecular Biology* (*Mosk.*) 25:761–69 (1991), which is hereby incorporated by reference), and ASPV (Jelkmann, "Nucleotide Sequences of Apple Stem Pitting Virus and of the Coat Protein of a Similar Virus from Pear Associated with Vein Yellows Disease and Their Relationship with Potex- and Carlaviruses," *J. General Virology* 75:1535–42 (1994), which is hereby incorporated by reference), with the latter two being the most similar to RSPaV-1. A representation of the sequence comparison is shown in FIG. 3B and the percent identities in amino acid sequences of the ORF of RSPaV-1 and the corresponding ORF of ASPV, PVM, and PVX are shown in Table 2 below. These analyses suggest that the ORFs of RSPaV-1 are compared with those of PVM and ASPV.

Figure 4A:
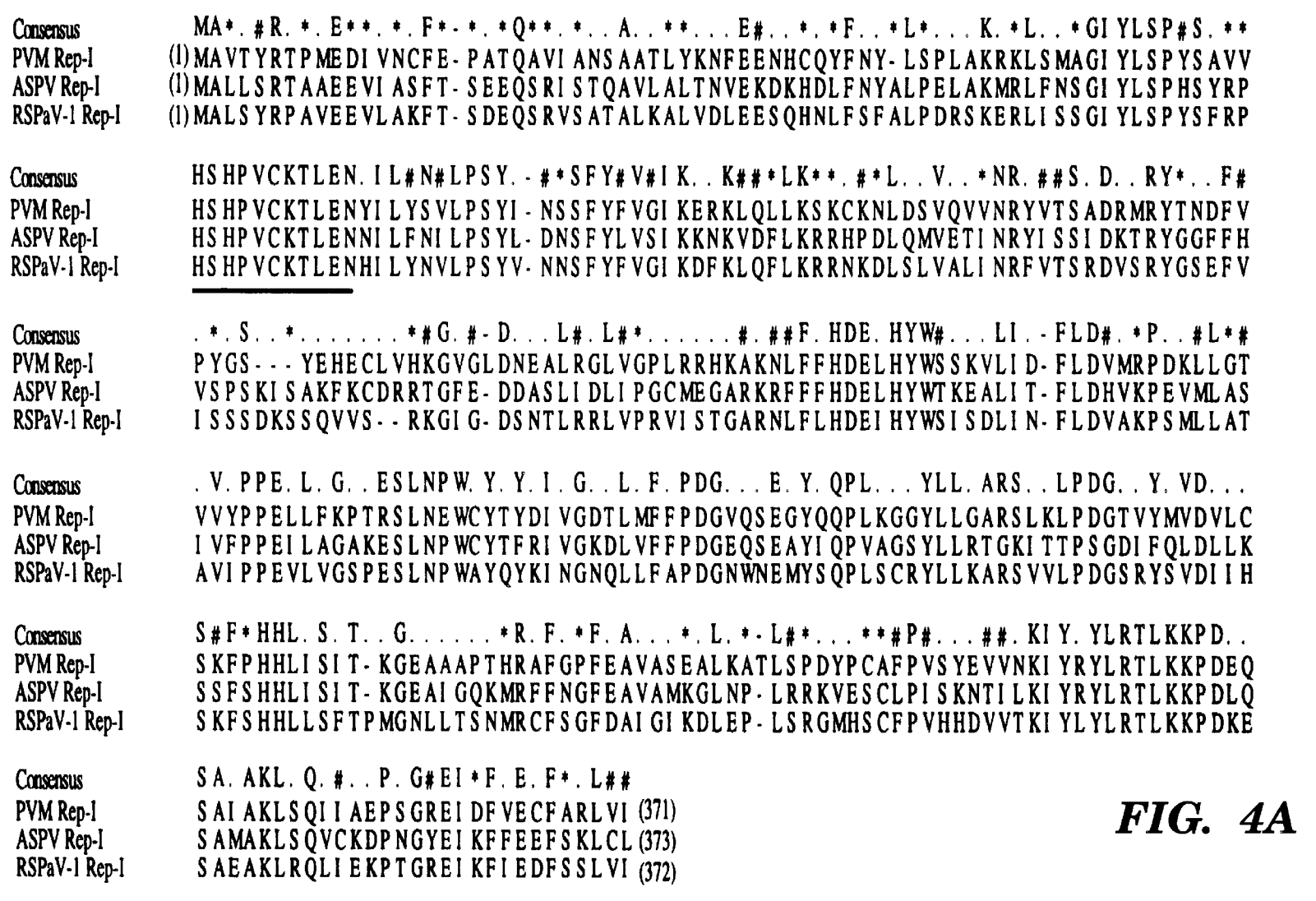

When the total amino acid sequence of RSPaV-1 ORF1 was used for comparison, it showed 39.6% and 37.6% identities with the replicases of ASPV and PVM respectively (Table 2). These homologies were mainly found in regions I (aa 1 to 372) and II (aa 1354–2161), which are at the N and C terminal portions of the putative replicase, respectively, shown at FIGS. 4A and 4B. Within region I, the identities of RSPaV-1 with ASPV and PVM were 49.2% and 47.2%, respectively (Table 2). The methyltransferase domain, which is conserved in Sindbis-like superfamily of plant viruses (Rozanov et al., "Conservation of the Putative Methyltransferase Domain: A Hallmark of the "Sindbis-like" Supergroup of Positive-Strand RNA Viruses," *J. General Virology* 73:2129–34 (1992), which is hereby incorporated by reference), was found in this region (FIG. 4A). Region II, on the other hand, showed even higher identities: 57.5% with ASPV and 53.2% with PVM (Table 2). A NTP binding motif "GXXXXGKS/T" (aa 1356 to 1363) ("X" stands for any amino acid residue), which is conserved in helicase proteins and helicase domains of eukaryotic positive strand RNA viruses (Gorbalenya et al., "A Novel Superfamily of Nucleotide Triphosphate-Binding Motif Containing Proteins which are Probably Involved in Duplex Unwinding in DNA and RNA Replication and Recombination," *FEBS Letters,* 235:16–24 (1988), which is hereby incorporated by reference), was found in the beginning of region II (FIG. 4B). The amino acid sequences of this motif in ASPV and PVM were identical to that of RSPaV-1 except for one position. Furthermore, amino acid sequence surrounding the GDD motif, which is conserved in all RNA dependent RNA polymerases of positive strand RNA viruses (Koonin, "The Phylogeny of RNA-Dependent RNA Polymerases of Positive-Strand RNA Viruses," *J. Gen. Virology* 72:2197–2206 (1991), which is hereby incorporated by reference), was located near the C terminus of the RSPaV-1 replicase protein and showed high identities to those of ASPV and PVM (FIG. 4B). Other conserved residues of positive strand RNA viruses as described by Koonin, "The Phylogeny of RNA-Dependent RNA Polymerases of Positive-Strand RNA Viruses," *J. Gen. Virology* 72:2197–2206 (1991), which is hereby incorporated by reference, were also found in this region. Based on these information, it was concluded that ORF1 of RSPaV-1 codes for the putative replicase protein.

The triple gene block is a common feature of several groups of plant viruses including carlaviruses, potexviruses, and ASPV. Comparison of RSPaV-1 ORF2 with those of PVM and ASPV showed evenly distributed homologies in

TABLE 2

| | Replicase | | | | | | | Coat Protein ORF5 |
|---|---|---|---|---|---|---|---|---|
| | ORF1 | | | | | | | |
| | Region I | Region II | | Triple Gene Block | | | | |
| | aa 1-372 | aa 1354-2161 | Total | ORF2 | ORF3 | ORF4 | Total | aa 142-245 |
| ASPV | 49.2 | 57.5 | 39.6 | 38.0 | 39.3 | 27.1 | 31.3 | 49.5 |
| PVM | 47.2 | 53.2 | 37.6 | 34.8 | 31.2 | 19.0 | 21.2 | 33.3 |
| PVX | 18.9 | 20.4 | 15.7 | 23.5 | 31.3 | 22.9 | 27.4 | 42.9 | amino acid sequence: 38.0% identity to ASPV and 34.8% to PVM (Table 2). The N terminal region of the 24.4 K protein (ORF2) contained the consensus sequence "GXGKS S/T" (aa 31 to 36) (FIG. 5A), which is observed in its counterparts in carlaviruses (Zavriev et al., "Complete Nucleotide Sequence of Genomic RNA of the Potato M-Virus," *Molecular Biology* (*Mosk.*) 25:761–69 (1991), which is hereby incorporated by reference) and a number of ATP and GTP binding proteins (Zimmem, "Evolution of RNA Viruses," in *RNA Genetics,* Holland et al., eds., CRC Press, Boca Raton, Fla., USA (1987), which is hereby incorporated by reference). The 12.8 K protein of RSPaV-1 encoded by ORF3 had 39.3% and 31.2% identities with its counterparts in ASPV and PVM respectively (Table 2). However, most of the matching occurred in a region from aa 29 to 62, among which 18 aa were fully conserved in all three viruses (FIG. 5B). These 12–13 K proteins may function in membrane binding (Morozov et al., "Nucleotide Sequence of the Open Reading Frames Adjacent to the Coat Protein in Potato Virus X Genome," *FEBS Letters* 213:438–42 (1987), which is hereby incorporated by reference). The 8.4 K protein encoded by RSPaV-1 ORF4, in contrast, showed much lower identities: 27.1% with that of ASPV and 19.0% with that of PVM (Table 2). However, four residues "TGES" (aa 38 to 41) were conserved in all three viruses (FIG. 5C). In vitro studies indicated that the analogous 7 K protein of PVM may bind to single or double stranded nucleic acids (Gramstat et al., "The 12 kDa Protein of Potato Virus M Displays Properties of a Nucleic Acid-Binding Regulatory Protein," *FEBS Letters,* 276:34–38 (1990), which is hereby incorporated by reference) and to plasma membrane (Morozov et al., "In vitro Membrane Binding of the Translation Products of the Carlavirus 7-kDa Protein Genes," *Virology* 183:782–85 (1991), which is hereby incorporated by reference).

A sequence similarity search in a DNA database revealed identities between the putative protein encoded for by RSPaV-1 ORF5 to the coat proteins (CPs) of several groups of plant viruses, indicating that RSPaV-1 ORF5 may code for the coat protein. MegAlign analysis revealed that RSPaV-1 ORF5 had 31.3% and 21.2% identities with the CPs of ASPV and PVM, respectively (Table 2). Most of the identities were found in the C terminal portion of the coat proteins (aa 142 to 245 for RSPaV-1), while the N terminal portions were quite variable in the numbers and sequences of amino acid residues. When the C terminal portion of RSPaV-1 CP was compared to the corresponding regions of ASPV and PVM, it showed 49.5% and 33.3% identities with ASPV and PVM, respectively (Table 2). In addition, the "RR/QX-XFDF" motif was found in the central region of RSPaV-1 CP (FIG. 5D). This motif is conserved in the CPs of positive strand RNA viruses with filamentous morphology and were reported to be involved in salt bridge formation (Dolja et al., "Phylogeny of Capsid Proteins of Rod-Shaped and Filamentous RNA Plant Virus: Two Families with Distinct Patterns of Sequence and Probably Structure Conservation," *Virology,* 184:79–86 (1991), which is hereby incorporated by reference). Therefore, it is believed that ORF5 encodes a putative coat protein.

MegAlign analysis, shown in FIGS. 6A and 6B, revealed that the 3' UTR of RSPaV-1 is more similar to that of PVM than to that of ASPV. For example, in a 75 nts stretch, RSPaV-1 had 68% identity with PVM. Within this region, 21 consecutive nucleotides were identical between these two viruses. The significance of this conservation in nucleotide sequence remains to be explored. In contrast, the 5' UTR of RSPaV-1 did not reveal significant similarities with those of PVM and ASPV.

It has been have shown that an 8.7 kbp dsRNA is consistently associated with grapevines that indexed positively on St. George for RSP. Sequence analyses of the dsRNA provide evidence that a virus is involved in RSP, which has now been named RSPaV-1. The complete nucleotide sequence of RSPaV-1 was determined from overlapping cDNA clones and RT-PCR-amplified cDNA fragments generated from the dsRNA. The RSPaV-1 genome has five ORFs coding for the putative replicase (ORF1), the triple gene block (ORF2–4), and the CP (ORF5). The existence of these ORFs and their potential to code for structural and non-structural viral proteins were further supported by the identification of conserved motifs which are the signatures of various viral proteins.

This work confirms and extends the findings of Walter and Cameron ("Double-stranded RNA Isolated from Grapevines Affected by Rupestris Stem Pitting Disease," *Am. J. Enology and Viticulture* 42:175–79 (1991), which is hereby incorporated by reference), and Azzam and Gonsalves ("Detection of dsRNA in Grapevines Showing Symptoms of Rupestris Stem Pitting Disease and the Variabilities Encountered," *Plant Disease* 75:960–64 (1991), which is hereby incorporated by reference), who observed a major dsRNA species of about 8.0–8.3 kbp in RSP-infected grapevines. In addition, such work also observed a smaller dsRNA of ca. 6.6 kbp. A dsRNA of similar size was also observed here, but it was consistently detected in only Colobel 257 and Seyval. The relationship, if any, of this smaller dsRNA to RSP remains to be determined. The small dsRNA of ca. 0.359 kbp, which Monette et al. ("Double-stranded RNA from Rupestris Stem Pitting-Affected Grapevines," *Vitis* 28:137–44 (1989), which is hereby incorporated by reference) isolated from RSP-infected grapevines growing in tissue culture, was not observed.

Electron microscopy evidence also suggests that RSP is caused by filamentous virus(es). Tzeng et al. ("Anatomical and Tissue Culture Studies of Rupestris Stem Pitting-Affected Grapevines," *Botan. Bulletin of Acad. Sinica* (*Taipei*) 34:73–82 (1993), which is hereby incorporated by reference) observed flexuous filamentous virus aggregates in the phloem parenchyma cells of young shoots of Sylvner grapevines that had indexed positively for RSP. Monette and Godkin ("Detection of Capillovirus-like Particles in a Grapevine Affected with Rugose Wood," *Vitis* 34:241–42 (1995), which is hereby incorporated by reference) observed a filamentous virus in Sauvignon blanc infected by RSP and LNSG. The relationship of these virus particles to RSP disease remains to be studied.

Evidence suggests that the cDNA library generated from the isolated dsRNA templates is not homogeneous for only RSPaV-1. During the process of sequencing cDNA clones, several clones (e.g., RSP47-4 and RSP158) were identified with high, but not identical, sequence similarities to RSPaV-1.

RSPaV-1 has the most similarities to ASPV, which has not yet been grouped into a virus genus. Both viruses have the same genome organization and their ORFs code for putative proteins of similar sizes, except that the coat protein of ASPV is significantly larger (44 kDa) than that of RSPaV-1 (28 kDa). Comparisons of RSPaV-1 with PVM carlavirus show some similarities in genome organization except that RSPaV-1 lacks ORF6 which is located at the 3' end of PVM genome. Although the genome organization of RSPaV-1 is similar to PVX potexvirus, the latter has a much smaller putative replicase. RSPaV-1 has no relation to grape viruses whose genomes have been sequenced so far. The closest possibilities, GVA (Minafra et al., "Grapevine virus A: Nucleotide Sequence, Genome Organization, and Relationship in the Trichovirus Genus," *Arch. Virology* 142:417–23 (1997), which is hereby incorporated by reference) and GVB (Saldarelli et al., "The Nucleotide Sequence and Genomic Organization of Grapevine Virus B," *J. General Virology* 77:2645–52 (1996), which is hereby incorporated by reference), have different genome structures than RSPaV-1.

Example 16

Specific and Universal Primers and the Detection of Different Strains of RSPaV by Reverse Transcription-Polymerase Chain Reaction (RT-PCR)

Among the 138 grapevine entries collected, 25 indexed negatively and 93 indexed positively for RSP on St. George, while the others were not indexed (see Tables 3–7 below). Symptoms induced by RSP on the woody cylinder of St. George after graft inoculation with chip-buds can be divided into two types. The first type is called "specific", that is, pits and/or grooves being restricted to the area on the woody cylinder below the inoculation sites. The other is called "nonspecific", that is, pits and/or grooves being present above, around, and below the inoculation sites.

TABLE 3

| Cultivar/Accession | ID | Index St. G | RT-PCR | Source |
| --- | --- | --- | --- | --- |
| Almeria K3 P 661 | 1483-13D1 | – | – | C |
| Auxerrois CL 56 | 658-1A2 | – | –a | C |
| Auxerrois CL 56 | 658-1A1-1A2 | – | – | C |
| GM 32458 | 604-8A2-2A2 | – | – | C |
| GM 7117-10 | 1347-16A1 | – | –a | C |
| Italia | 1186-5B1 | – | – | C |
| Pslanka (H) | 23-10A2-2A2 | – | – | C |
| Ventura (V. 51061) (H) | 1166-2A1 | – | – | C |
| Verdelet (H) | 1170-3C2-2S1 | – | – | C |
| Verduzzo (V) | 233A | – | – | I |
| Vivant (V. 63331) (H) | 1166-3A1 | – | – | C |
| Control | | | | |
| Sauvignon Blanc (V) | AV-4 #2 | – | –a | U |

Symbols:
V., *Vitis vinefera*; R., *Vitis riparia*; H., hybrid; C., Canada; I., Italy; U., USA; P., Portugal;
a, tested by RSP149F1/R1 and 95F1/R1 and results agree to each other; b, tested by 95F1/R1 only

TABLE 4

| Cultivar/Accession | ID | Index St. G | RT-PCR | Source |
| --- | --- | --- | --- | --- |
| Aragonez (Temperanillo) | 238 | – | + | P |
| Albalonga | 1058-4A2-2A1 | – | + | C |
| Cabernet Franc (V) | 147A | – | + | I |
| Chardonnay (V) | 80A | – | + | I |
| Ehrenfelser PM 1 (V) | 1169-1A1 | – | + | C |
| Freedom (H) | PI 588370 | – | +a | U |
| Harslevellu P 679 | 1483-2B1 | – | + | C |
| Heroldrebe | 1318-2A1 | – | + | C |
| Malvasia Fina | 340 | – | + | P |
| Perle of Zala | 1407-5A1 | – | + | C |
| Refosco (V) | 181A | – | + | I |
| San Giovese Brunello CL BBS 11 | 1497-2A1 | – | + | C |
| Touriga Francesa | 313 | – | + | P |

Symbols:
V., *Vitis vinefera*; R., *Vitis riparia*; H., hybrid; C., Canada; I., Italy; U., USA; P., Portugal;
a, tested by RSP149F1/R1 and 95F1/R1 and results agree to each other; b, tested by 95F1/R1 only

TABLE 5

| Cultivar/Accession | ID | Index St. G | RT-PCR | Source |
| --- | --- | --- | --- | --- |
| Albalonga | 1058-4A2-1A2 | + | + | C |
| Aminia (H) | PI 588306 | + | + | U |
| Antao Vaz | CL 245 | + | + | P |
| Aragonez (Temperanillo) | 350 | + | + | P |
| Auxerrois CL 56 | 658-1A1 | + | + | C |
| Badacsony-10 | 1407-1A1 | + | + | C |
| Bertille Seyve 3408 (H) | GVIT 348 | + | +b | U |
| Bertille Seyve 5563 (H) | PI 181647 | + | +a | U |
| Blauer Spatburgunder | Q1378-1 | + | +b | C |
| Blauer Zwiegelt/5BB | 1240-1A1 | + | +a | C |
| Bonbino B 9 | 1586-17P3 | + | + | C |
| Brant (H) | 1078-1A1 | + | + | C |
| Cabernet Franc (V) | 151A | + | + | I |
| Cabernet Sauvignon (V) | 124A | + | + | I |
| Cardinal | Q390-13 | + | +b | C |
| Chardonnay (V) | Q661-4 | + | +b | C |
| Chardonnay CL 116 (V) | 1021-13A2 | + | +a | C |
| Chardonnay (V) | 128B | + | +b | I |
| Chardonnay (V) | 72A | + | +b | I |
| Chardonnay (V) | 73A | + | +b | I |
| Chardonnay (V) | 83A | + | + | I |
| Chazan CL 538 | 1346-6A1 | + | +a | C |
| Chenin Blanc CL 220 | 1555-6A1 | + | + | C |
| Colobel 257 (Seibel 8357) (H) | PI 588062 | + | +a | U |
| Couderc 28-112 (H) | PI 588248 | + | +a | U |
| De Chaunac S9549 (H) | Q659-1 | + | +b | C |
| Durella 3 | 1586-13P1 | + | + | C |
| Esgana cao | 276 | + | + | P |
| Egri Csillagok-30 | 1407-3A1 | + | + | C |
| Gamay Precoce | 1500-2A1 | + | + | C |
| GM 31875 | 782-18A1 | + | +a | C |
| GM 32458 | 604-8A1 | + | + | C |
| GM 32458 | 782-21B1 | + | + | C |
| GM 6417-7 | 1347-7A1 | + | + | C |
| GM 6497-4 | 1347-14A1 | + | + | C |
| GM 7116-10 | 1362-4A1 | + | + | C |
| GM 7117-13 | 1347-17A2 | + | + | C |
| Grande Glabre (R) | 279897 | + | +a | U |
| Gyongyriziling | 1407-4A1 | + | + | C |
| ILL 344-1 (H) | GVIT 658 | + | +a | U |
| Joffre (Kuhlmann 187-1) (H) | GVIT 381 | + | +a | U |
| Koret (H) | Q1179-7 | + | +b | C |
| Malvasia (V) | 153A | + | + | I |
| Malvasia (V) | 161A | + | + | T |
| Merlot CL 447 (V) | 1236-17A1 | + | + | C |
| Moureto | 87 | + | + | P |
| Moureto | 96 | + | + | P |

TABLE 5-continued

| Cultivar/Accession | ID | Index St. G | RT-PCR | Source |
|---|---|---|---|---|
| Muscat De Hambourg CL 202 | 1346-5A1 | + | + | C |
| Perle of Csaba | Q806-1 | + | +b | C |
| Pinot Chardonnay CL 76 (V) | 949-3A2 | + | +a | C |
| Pinot Chardonnay CL 277 (V) | 949-8B1 | + | + | C |
| Pinot Grigio (V) | 104A | + | +b | I |
| Pinot Grigio (V) | 108A | + | +b | T |
| Pinot Grigio (V) | 114A | + | + | I |
| Pollux B6-18 | 1357-4A1 | + | + | C |
| Pslanka (H) | 23-10A2 | + | + | C |
| Ravat 34 | PI 588247 | + | +a | U |
| Refosco (V) | 199A | + | +? | I |
| Refosco (V) | 195A | + | + | I |
| Riesling CL 49 (V) | 1555-2A1 | + | +a | C |
| San Giovese Brunello CL E BS 4 | 1497-3B1 | + | + | C |
| Schew-Rebe | 778-6A1 | + | +a | C |
| Semillon CL 299 (V) | 1555-7A1 | + | +a | C |
| Seyval Blanc (Seyve Villard 5-276) (H) | PI 588309 | + | +a | U |
| Seyve Villard 14-287 (H) | PI 588246 | + | +a | U |
| Seyve Villard 3160 (H) | PI 181630 | + | +a | U |
| Titan | Q1235-1 | + | +b | C |
| Verdelet (H) | PI 186260 | + | +a | U |
| Verdelho | 274 | + | + | P |
| Verduzzo (V) | 222A | + | +b | I |
| Verduzzo (V) | 226A | + | +b | I |
| Verduzzo (V) | 239A | + | + | I |
| Vidal Blanc | 1200-5A1 | + | +a | C |
| Weiser Burgunder | Q782-40 | + | +b | C |
| 3309 C | 330-4A1 | + | + | C |
| 420 A | 1483-4A1 | + | + | C |
| 7542 | Q1386-1 | + | +b | C |
| Pinot Noir (V) | 1186-9A2 | + | +a | C |
| Thompson Seedless (V) | RSP105 | + | +a | U |

Symbols:
V., *Vitis vinefera*; R., *Vitis riparia*; H., hybrid; C., Canada; I., Italy; U., USA; P., Portugal;
a, tested by RSP149F1/R1 and 95F1/R1 and results agree to each other; b, tested by 95F1/R1 only.

TABLE 6

| Cultivar/Accession | ID | Index St. G | RT-PCR | Source |
|---|---|---|---|---|
| Aligote | Q637-2B2 | + | -b | C |
| Aragonez (Temperanillo) | 232 | + | - | P |
| Canandaigua (H) | GVIT 566 | + | -a | U |
| Challenger (H) | Q1338-1 | + | -b | C |
| Fercal CL 242 | 1551-4A1 | + | -a | C |
| GM 7746-6 | 1362-6A1 | + | - | C |
| Gravesac CL 264 | 1551-3A1 | + | -a | C |
| Honey Red | 1339-6A1 | + | - | C |
| Kee-Wah-Din (R) | 1278-1A1 | + | - | C |
| Periquita | 72 | + | - | P |
| Tajoznyt Izumrud (H) | Q2-2 | + | -b | C |
| Thurling | 1047-4A2-1A2 | + | - | C |
| Verdelet | 1170-3D2-2A1 | + | - | C |
| 5BB CL 114 | 1236-2A1 | + | - | C |
| Alphonse Lavalle | | NI | + | I |
| Ancellotta | | NI | + | I |
| Chardonnay (V) | 127 | NI | + | I |
| Kober 5BB? | 100 | NI | + | I |
| Moscato d'Adda | 7 | NI | + | I |
| Periquita | 624 | NI | + | P |
| Periquita | 633 | NI | + | P |
| Riesling (V) | 3 | NI | + | I |
| Seyval (H) | Peterson | NI | + | U |
| Terrano | 1/1/3/K | NI | + | I |
| Thurling | 1047-4A2-2A1 | NI | - | C |
| Tocai Rosso 19 | 1586-21P4 | NI | + | C |
| Trebbiano Toscano | 67 | NI | - | I |
| Vidal | Peterson | NI | + | U |

Symbols:
V., *Vitis vinefera*; R., *Vitis riparia*; H., hybrid; NI, not indexed; C., Canada; I., Italy; U., USA; P., Portugal;
a, tested by RSP149F1/R1 and 95F1/R1 and results agree to each other; b, tested by 95F1/R1 only

TABLE 7

| Cultivar/Accession | ID | Index St. G | RT-PCR | Source |
|---|---|---|---|---|
| V. acerifolia | PI 588448 | NI | - | U |
| V. acerifolia | PI 588449 | NI | - | U |
| V. cinerea | PI 588446 | NI | - | U |
| V. monticola | PI 588454 | NI | - | U |
| V. riparia | PI 495622 | NI | - | U |
| V. sp. yenshanesis | PI 588421 | NI | - | U |

Symbols:
V., *Vitis vinefera*; R., *Vitis riparia*; H., hybrid; NI, not indexed; C., Canada; I., Italy; U., USA; P., Portugal;
a, tested by RSP149F1/R1 and 95F1/R1 and results agree to each other; b, tested by 95F1/R1 only Among the 93 RSP-infected grapevines, 79 (85%) produced cDNA fragments of expected sizes in repeated RT-PCR using RSP149F1/R1 primers (SEQ. ID. Nos. 49 and 50) and/or RSP95F1/R1 primers (SEQ. ID. Nos. 47 and 48), while the other 14 were negative (see Tables 5 and 6). Interestingly, 12 of 14 (85.7%) grapevine accessions which were not indexed for RSP also produced cDNA fragments of expected size in RT-PCR (see Table 6). Sauvignon blanc (healthy control) was negative in repeated RT-PCR (see Table 3).

Results of RT-PCR for grapevines indexed negatively for RSP were surprising (see Tables 3 and 4). While 11 were negative in RT-PCR tests (excluding Sauvignon blanc healthy control), the other 13 produced cDNA fragments of expected sizes.

Since RSPaV-1 was detected not only from grapevines which indexed positively for RSP but also from some of the grapevines indexed negatively for RSP, a search for more healthy materials for RT-PCR tests became necessary. As the majority of plant viruses do not pass on through seeds, grapevine seedlings are probably free of RSPaV-1. Based on this assumption, six seedlings from five Vitis species were included in RT-PCR (see Table 7). None of them produce cDNA of expected size in RT-PCR using RSP149R1/F1 primers (SEQ. ID. Nos. 49 and 50).

The data described above (and shown in Tables 3–7) indicate that RSPaV-1 is closely associated with RSP and that it is likely the causal agent of RSP. RT-PCR detected RSPaV-1 specific sequences from most of the RSP-infected grapevines collected from a wide range of viticultural regions of the world. Among the 93 grapevine accessions indexed positively for RSP on St. George, 85% were positive in RT-PCR (see Table 5). The data also suggests that RT-PCR has the potential to be used as a standard method for diagnosing RSP. This method is advantageous over the biological indexing on indicator St. George, because it is simpler, quicker, and more sensitive.

RT-PCR did not detect RSPaV-1 sequences from 14 of the grapevine accessions indexed positively for RSP (see Table 6). The discrepancy between RT-PCR and indicator indexing can be attributed to the existence in grapevines of different viruses or strains of the same virus which may all induce similar pitting and/or grooving symptoms on St. George upon graft-inoculation. It is believed these agents are only slightly different from RSPaV-1 at the level of their nucleotide sequences, but significant enough to hinder them from being detected by RT-PCR using RSPaV-1 specific primers.

Figure 9:
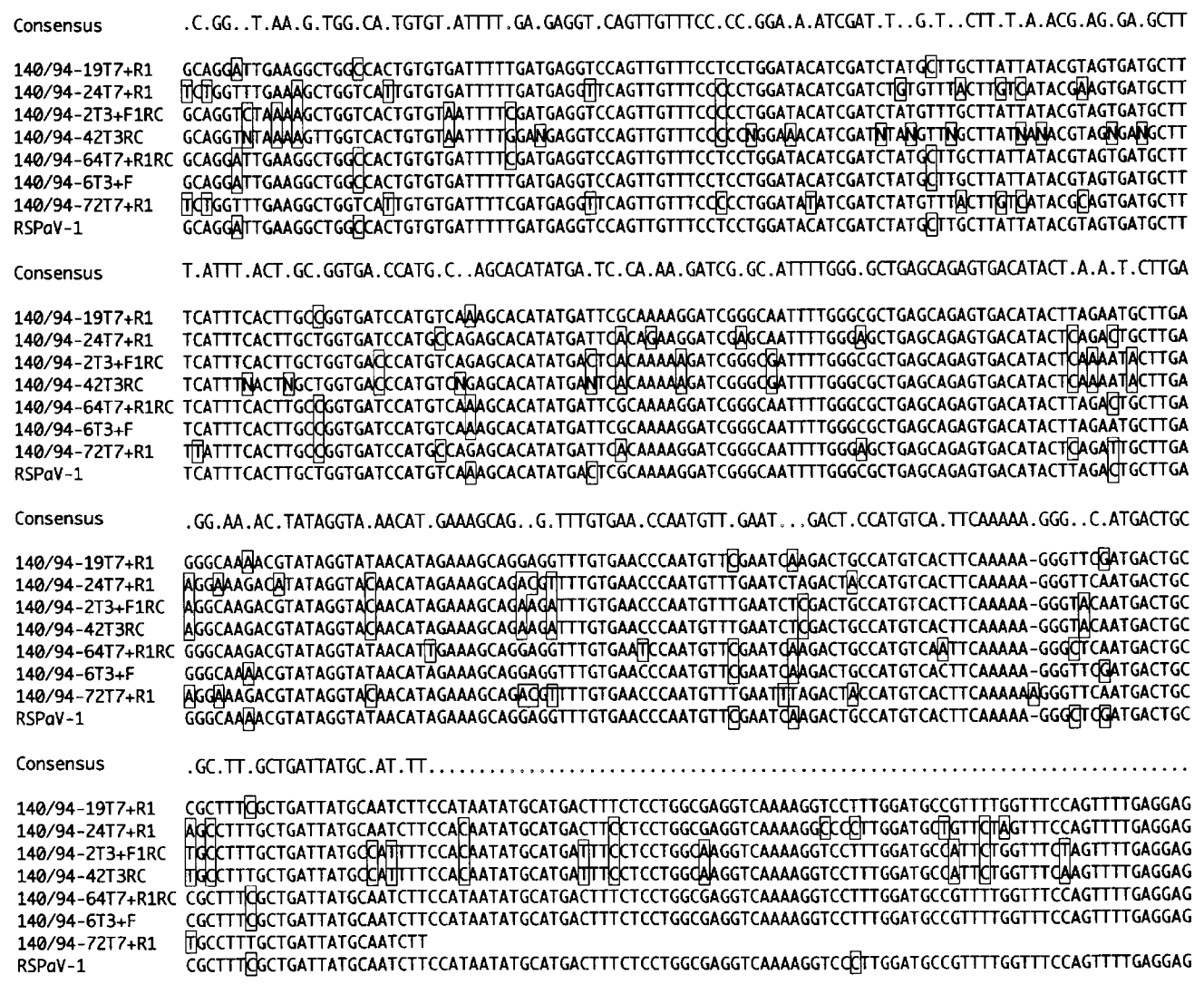

It is likely that many RSPaV strains have genomes with nucleotide sequences that are highly similar to the nucleotide sequence of the RSPaV-1 genome. Evidence that supports this hypothesis includes the finding of a highly conserved region of ca. 600 bps among the nucleotide sequences of RSPaV-1 (type strain) and seven other cDNA clones, as shown in FIG. 9. The nucleotide sequence identities of these strains to RSPaV-1 (type strain) range from 83.6% to 98.4%. If oligonucleotides are chosen which are conserved among all these strains (i.e., with one or only a few mismatches), then the oligonucleotides should function as universal primers, allowing all of the strains to be detected by RT-PCR. Based on this theory, a primer pair (BM98-3F/BM98-3R) can be designed to amplify a DNA fragment of 320 bps from all these clones. BM98-3F has a nucleotide sequence corresponding to SEQ. ID. No. 51 as follows:

GATGAGGTCCAGTTGTTTCC                    20

BM98-3R has a nucleotide sequence corresponding to SEQ. ID. No. 52 as follows:

ATCCAAAGGACCTTTTGACC                    20

Primers BM98-3F/BM98-3R can be used in RT-PCR to test further some of the grapevine samples which were negative for RSPaV in RT-PCR using RSP95F1/RSP95R1 primers (SEQ. ID. Nos. 47 and 48, respectively) or RSP149F1/RSP149R1 primers (SEQ. ID. Nos. 49 and 50, respectively). Results show that 6 of the 9 samples included were positive for RSPaV in RT-PCR using BM98-3F/BM98-3R primers. This indicates that these universal primers can be used to achieve even higher detection rates.

Another pair of primers (BM98-1F/BM98-1R) can be designed in a way that they can amplify DNA of 760 bps from RSPaV-1, RSP47-4, and RSP158. BM98-1F has a nucleotide sequence corresponding to SEQ. ID. No. 53 as follows:

CTTGATGAGTACTTGTC                       17

BM98-1R has a nucleotide sequence corresponding to SEQ. ID. No. 54 as follows:

GCAAGGATTTGGATGGC                       17

Other "universal primers" can be designed manually or with computer programs (such as PrimerSelect) in the same way so that they contain conserved regions of nucleotide sequences for different strains of RSPaV-1.

RT-PCR detected RSPaV-1 sequences from 54% of grapevines negative for RSP as judged by indexing on St. George (see Tables 3 and 4). Several possibilities may account for this discrepancy. First, RT-PCR is much more sensitive than indicator indexing. Virus(es) of extremely low concentration may not induce visible symptoms on St. George within the standard indexing period, while they can be detected by RT-PCR. Second, judging indexing results can, in some cases, be very subjective. For example, it is very difficult to reach a conclusion on whether a grapevine is infected with RSP when only one or a few small pits are present on the woody cylinder of St. George. Third, uneven distribution of virus(es) within grapevines and the relatively limited number of replicates of St. George indicators may result in the failure to detect RSP-infection.

RSP seems to be widespread in different types of grapevines including V. vinifera, hybrids, V. riparia, and rootstocks. It occurs in a wide range of geographic regions including North America, Europe, Australia, and possibly many other countries as well. Testing grapevines from other areas of the world using RSPaV-1 specific primers will provide definitive information on the exact distribution of RSP throughout the world. It is also interesting to investigate whether RSP is transmitted by any vectors in nature.

RSP is a disease under quarantine in Washington and New York of the USA. Since this work and the work of others (Golino and Butler, "A Preliminary Analysis of Grapevine Indexing Records at Davis, Calif.," in *Proceedings of the 10th Meeting of the ICVG*, pp. 369–72, Rumbos et al., eds., Volos, Greece (1990); Azzam and Gonsalves, "Detection of dsRNA in Grapevines Showing Symptoms of Rupestris Stem Pitting Disease and the Variabilities Encountered," *Plant Disease*, 75:96–964 (1991); Garau, "Kober Stem Grooving and Grapevine Virus A: A Possible Relationship," in *Extended Abstracts of the 11th Meeting of the International Council for the Study of Viruses and Virus Diseases of the Grapevine*, p. 54, Montreux, Switzerland (1993); Credi, "Characterization of Grapevine Rugose Wood Sources from Italy," *Plant Disease*, 82:1288–92 (1997), all of which are hereby incorporated by reference) showed that RSP is so wide-spread, it is questionable whether or not RSP should be kept under plant quarantine any longer. The devlopment and advance of rapid diagnostic methods will also allow us to investigate on the economic damage caused by RSP.

According to Goheen ("Rupestris Stem Pitting," in *Compendium of Grape Diseases*, p. 53, Pearson and Goheen, eds., American Phytopathological Society Press, St. Paul, Minn., USA (1988), which is hereby incorporated by reference), RSP is a disease which induces, after graft-inoculation with a chip bud from an infected grapevine, a row of small pits on the woody cylinder of St. George below the point of inoculation. This definition may not be comprehensive. Indexing record indicated that two types of stem pitting (specific vs. nonspecific) were often observed on the woody cylinder of St. George upon graft inoculation with chip buds. For example, among 16 RSP-positive grapevines collected from Canada in 1995, eight developed specific type symptoms, while the others produced nonspecific symptoms. Credi ("Characterization of Grapevine Rugose Wood Sources from Italy," *Plant Disease*, 82:1288–92 (1997), which is hereby incorporated by reference) also observed these two types of stem pitting in his indexing work. However, from the primers used in RT-PCR, as described above, RSPaV-1 was detected in grapevines showing both types of symptoms on St. George.

Thus, RT-PCR detected RSPaV-1 sequences from a wide range of grapevines collected from a number of major grapevine growing countries. The data clearly suggest that RSPaV-1 is closely associated with Rupestris stem pitting of grapevines and that it is likely the causal virus of RSP. Use of "universal" primers which can detect multiple agents which are highly similar to RSPaV-1 in nucleotide sequences would improve the detection rate by RT-PCR. In addition, antibodies produced against bacteria-expressed coat proteins of RSPaV-1 will help in finding the viral particles from RSP infected grapevines and in rapid detection of RSP.

Example 17

Southern Hybridization

Figure 7A:
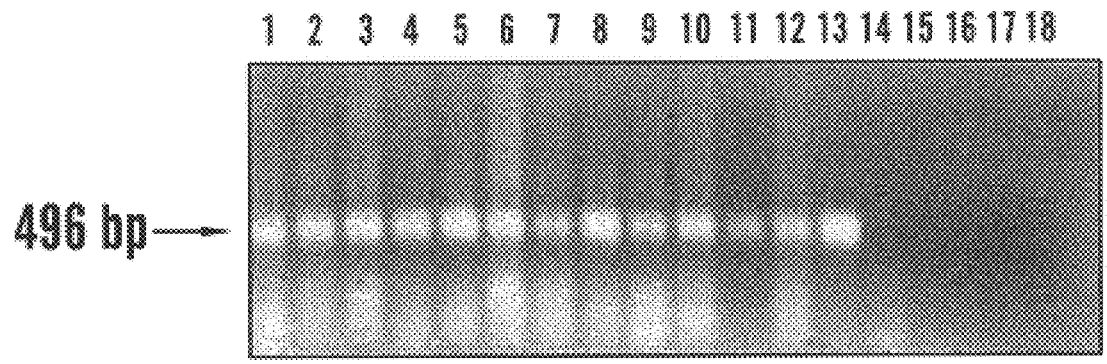
FIGS. 7A–B are photographs comparing the results of RT-PCR of grapevines using RSP149 primers (FIG. 7A) and Southern blot hybridization of RT-PCR amplified cDNA fragments to RSPaV-1 specific probe (FIG. 7B). MMLV-RT (Promega) was used in reverse transcription. Taq DNA polymerase (Promega) was used in PCR. For the RT-PCR and Southern blot hybridization: lane 1, Ehrenfelser PM1 (1169-1A1); lane 2, Cabernet franc 147A; lane 3, Chardonnay 80A; lane 4, Refosco 181A; lane 5, Touriga francesa 313; lane 6, 3309C (330-4A1); lane 7, 420A (1483-4A1); lane 8, Chardonnay 83A; lane 9, Malsavia 153A; lane 10, Aragnonex 350; lane 11, Aminia; lane 12, Chardonnay 127; lane 13, Kober 5BB 100; lane 14, Verduzzo 233A; lane 15, *V. riparia*; lane 16, *V. monticola*; lane 17, H$_2$O.
Figure 7B:
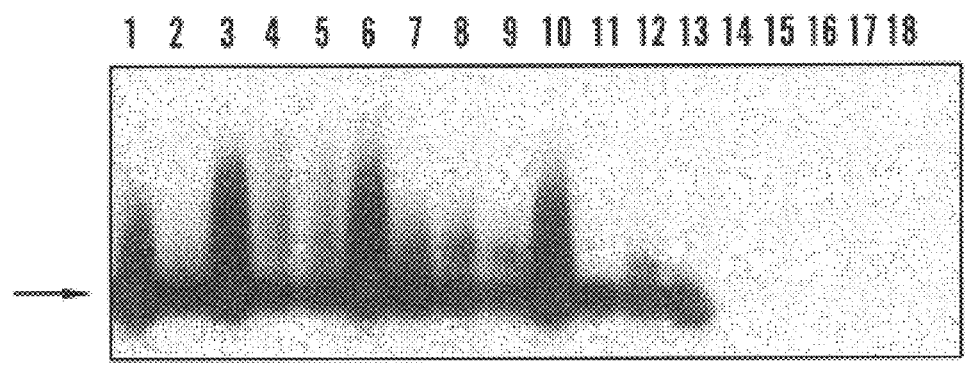
Figure 8:
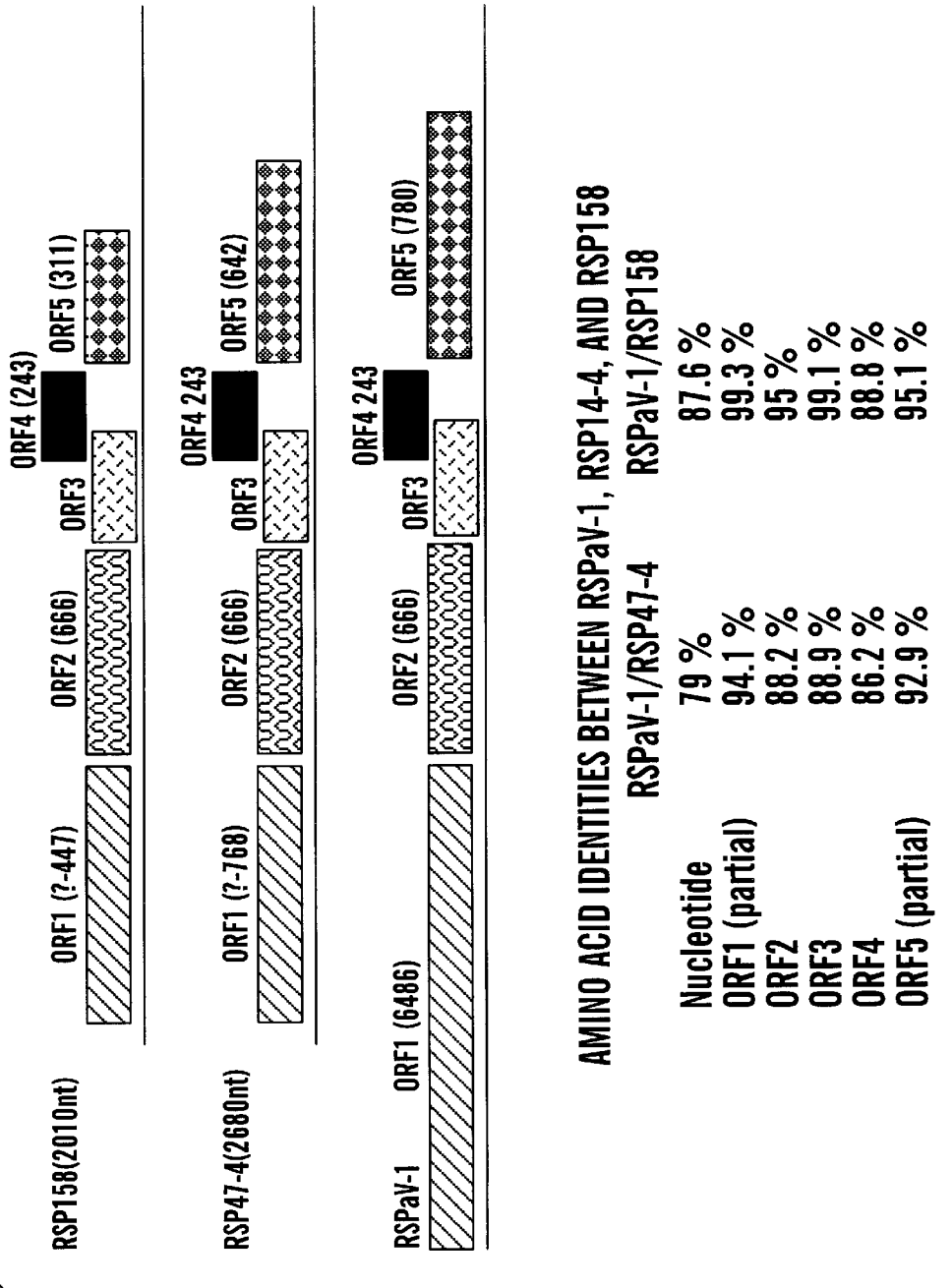
FIG. 8 is a schematic representation of the identical genome organization among RSPaV-1 (the type strain), RSP47-4, and RSP158. The number of amino acid residues of the comparable ORFs (boxes shaded with the same pattern) among these three strains are the same (note: ORF1 and ORF5 of RSP47-4 and RSP158 are incomplete). The comparable ORFs also have high nucleotide and amino acid sequence identities, which are indicated on the bottom. Only the C-terminal portion of the ORF1 of RSPaV-1 is shown in this diagram.
Figure 10:
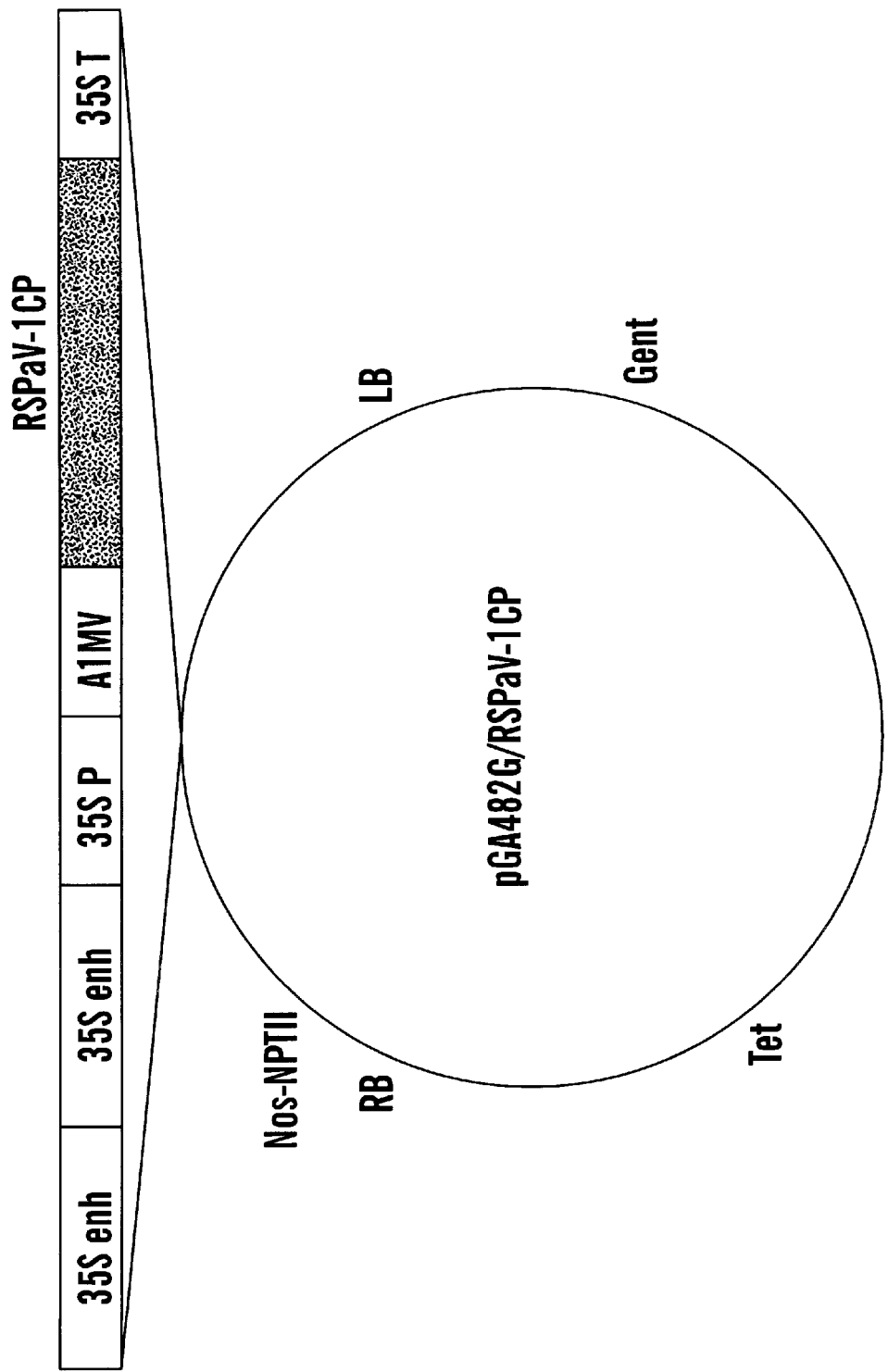
FIG. 10 is a schematic representation of a plant transformation vector containing the RSPaV-1 coat protein gene. This vector is designated pGA482G/RSPaV-1CP, which has the double CaMV 35S enhancers, the 35S promoter, the leader sequence of A1MV, and the 35S terminator sequence. RB, right border; LB, left border; Tet, tetracycline resistance gene; and Gent, gentamycin resistance gene.

To confirm the specificity of the RT-PCR products to RSPaV-1, Southern blot hybridization was conducted using 32P labeled probe specific to RSPaV-1. As shown in FIG. 7, the Southern blot hybridization confirmed the results of the RT-PCR in each of the tested samples. Specifically, cDNA fragments amplified by RT-PCR from 16 selected RT-PCR positive samples hybridized with the probe.

Example 18

Constructing Expression Systems, Expression of a Fusion Protein Containing the RSPaV-1 Coat Protein, Production of Antibodies Against the Fusion Protein and Their Use in Detecting RSPaV-1 from Grapevines The coat protein gene (SEQ. ID. No. 10) of RSPaV-1 was cloned into the EcoRI and HindIII sites of the polylinker region of a protein expression vector pMAL-c2 which, upon induction by inducer IPTG, produces a fusion protein containing maltose binding protein (MBP) and the coat protein of RSPaV-1. The fusion protein of expected size (ca. 71 KDa) was produced in E. coli bacteria after induction with IPTG. This fusion protein was purified through affinity chromatography using an amylose column. Purified fusion protein was used as an antigen to immunize a rabbit (by subcutaneous injection along the back) with the following scheme:

first injection, 400 μg fusion protein in 0.5 ml column buffer with Freund's complete adjuvant;
second injection, 100 μg of protein in 0.5 ml column buffer with Freund's incomplete adjuvant; and
third injection, 100 μg of protein in 0.5 ml buffer with Freund's incomplete adjuvant.

Blood containing the antibodies was collected 70 days after the first injection. The antibodies were recovered and successfully used in an enzyme linked immunoabsorbent assay to detect the presence of virus particles (i.e., coat protein) of RSPaV-1 from a variety of tissue types of grapevines infected with RSP.

The antibodies produced against the expressed RSPaV-1 coat protein, therefore, are useful in the identification of the particles associated with RSP disease of grapevines, in the purification of the particles of RSPaV-1, and in the development of a serological diagnosis for RSP in grapevine. The use of the antibodies is suitable for detecting different strains of RSPaV-1. Because the coat proteins for strains RSP47-4 and RSP158 have high amino acid identities with the coat protein of RSPaV-1, it is very likely that the antibodies raised against RSPaV-1 coat protein will also detect other strains. Antibodies can be used in an ELISA to assay rapidly a large number of samples, thus making commercial development and utilization of diagnostic kits possible.

Example 19

Transformation of Grapevines with a Vector Containing RSPaV-1 Coat Protein Gene and Analysis of Transgenic Grapevines for Resistance to RSP The DNA molecule coding for the RSPaV-1 coat protein (e.g., SEQ. ID. No. 10) was cloned into a pEPT8 plant expression vector that contains the double 35S enhancer at restriction sites SalI and BamHI. The resulting recombinant plasmid, designated pEPT8/RSPaV-1 coat protein, was then cloned into the plant transformation vector pGA482G, which has resistance genes to gentamycin and tetracycline as selection markers. The resultant pGA482G containing pEPT8/RSPaV-1CP was used to transform grapevines using the Agrobacterium method.

The rootstock Vitis rupestris Scheele St. George was used in genetic transformation. Anthers were excised aseptically from flower buds. The pollen was crushed on a microscope slide with acetocarmine to observe the cytological stage (Bouquet et al., "Influence du Gentype sur la Production de cals: Dembryoides et Plantes Entieres par Culture Danthers in vitro dans le Genre Vitis," C.R. Acad. Sci. Paris III 295:560–74 (1982), which is hereby incorporated by reference). This was done to determine which stage was most favorable for callus induction.

Anthers were plated under aseptic condition at a density of 40 to 50 per 9 cm diameter Petri dish containing MSE. Plates were cultured at 28° C. in the dark. After 60 days, embryos were induced and transferred to hormone-free medium (HMG) for differentiation. Torpedo stage embryos were transferred to MGC medium to promote embryo germination. Cultures were maintained in the dark at 26–28° C. and transferred to fresh medium at 3–4 week intervals. Elongated embryos were transferred to rooting medium (5–8 embryos per jar). The embryos were grown in a tissue culture room at 25° C. with a daily 16 h photoperiod (76 μmol. s) to induce shoot and root formation. After plants developed roots, they were transplanted to soil in the greenhouse.

The protocols used for transformation were modified from those described by Scorza et al., "Transformation of Grape (Vitis vinifera L.) Zygotic-Derived Somatic Embryos and Regeneration of Transgenic Plants," Plant Cell Rpt. 14:589–92 (1995), which is hereby incorporated by reference. Overnight cultures of Agrobacterium strain C58Z707 or LBA4404 were grown in LB medium at 28° C. in a shaking incubator. Bacteria were centrifuged for 5 minutes at 3000–5000 rpm and re-suspended in MS liquid medium (OD 1.0 at A600 nm). Calli with embryos were immersed in the bacterial suspension for 15–30 minutes, blotted dry, and transferred to HMG medium with or without acetosyringone (100 μM). Embryogenic calli were co-cultivated with the bacteria for 48 h in the dark at 28° C. The plant material was then washed in MS liquid plus cefotaxime (300 mg/ml) and carbenicillin (200 mg/ml) 2–3 times. To select transgenic embryos, the material was transferred to HMG medium containing either 20 or 40 mg/L kanamycin, 300 mg/L cefotaxime, and 200 mg/L carbenicillin. Alternatively, after co-cultivation, embryogenic calli were transferred to initiation MSE medium containing 25 mg/l kanamycin plus the same antibiotics listed above. All plant materials were incubated in continuous darkness at 28° C. After growth on selection medium for 3 months, embryos were transferred to HMG or MGC without kanamycin to promote elongation of embryos. They were then transferred to rooting medium without antibiotics. Non-transformed calli were grown on the same media with and without kanamycin to verify the efficiency of the kanamycin selection process.

The X-gluc (5-bromo-4-chloro-3-indoyl-β-glucuronidase) histochemical assay was used to detect GUS (β-glucuronidase) activity in embryos and plants that were transformed with constructs containing the GUS gene that survived kanamycin selection. All propagated plants were screened using an enzyme linked immunoabsorbent assay (ELISA) system (5 Prime-3 Prime, Boulder, Colo.) to detect the NPTII (neomycin phosphotransferase II) protein in leaf extracts. ELISA tests with respective coat protein (CP)-specific antibodies were used to assay for CP. ELISA results were read on an SLT Spectra ELISA reader (Tecan U.S. Inc., Research Triangle Park, N.C.) 15–60 minutes after the substrate was added.

PCR analysis was carried out to detect the presence of transgene sequences in grape plants. Genomic DNA was isolated from transformed and non-transformed grape plants according to the method of Lodhi et al., "A Simple and Efficient Method for DNA Extraction from Grapevine Cultivars and Vitis Species," *Plant Mol. Biol. Rpt.* 12:6–13 (1994), which is hereby incorporated by reference. Primer sets included those of specific primers to the transgene. DNA was initially denatured at 94° C. for 3 minutes, then amplified by 35 cycles of 1 minute at 94° C. (denaturing), 1 minute at 52° C. (annealing), and 2 minutes at 72° C. (polymerizing). Reaction samples were directly loaded and electrophoresed in 1.5% agarose gels.

Southern analysis of transformants was accomplished by extracting genomic DNA from young leaves of transformed and non-transformed plants (3309C) as described above. DNA (10 μg) was digested with the restriction enzyme Bgl II, electrophoresed on a 0.8% agarose gel in TAE buffer and transferred to a Genescreen Plus membrane by capillary in 10× SSC. A probe was prepared by random primer labeling of a PCR amplified gene coding sequence with radioisotope $^{32}$P-dATP (Dupont, NEN). Pre-hybridization and hybridization steps were carried out at 65° C. following the manufacturer's instruction. The autoradiograph was developed after overnight exposure.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method for detecting a Rupestris stem pitting associated virus in a sample, said method comprising:

providing a primer that binds to Rupestris stem pitting associated virus nucleic acid molecule as a probe in a gene amplification detection procedure under conditions that permit gene amplification to occur;

contacting the sample with the primer; and detecting a gene amplification product indicating that Rupestris stem pitting associated virus is present in the sample.

2. A method according to claim 1, wherein the gene amplification detection procedure is selected from the group consisting of polymerase chain reaction and immunocapture polymerase chain reaction.

3. A method according to claim 1, wherein said method detects RSPaV-1, RSP47-4, or RSP158.

4. A method according to claim 3, wherein the primer has a nucleotide sequence selected from the group consisting of SEQ. ID. No. 53, SEQ. ID. No. 54, SEQ. ID. No. 51, and SEQ. ID. No. 52.

* * * * *

UNITED STATES PATENT AND TRADEMARK OFFICE
CERTIFICATE OF CORRECTION

PATENT NO. : 6,093,544
DATED : July 25, 2000
INVENTOR(S) : Dennis Gonsalves and Baozhong Meng It is certified that error appears in the above-identified patent and that said Letters Patent is hereby corrected as shown below:

Title page, Item [54] and Column 1, lines 1-3,
Title, replace "RUPESTRIS STEM PITTING ASSOCIATED VIRUS NUCLEIC ACIDS, PROTEINS, AND THEIR USES" with -- *RUPESTRIS* STEM PITTING ASSOCIATED VIRUS NUCLEIC ACIDS AND USES THEREOF --;

Item [56], OTHER PUBLICATIONS, replace "Portyvirus" with -- Potyvirus --;

Column 4,
Line 31, replace "specifics" with -- specific --;

Column 72,
Line 7, replace "*Acad. Press, Orlando, Vol. I,*" with -- Acad. Press, Orlando, Vol. I, --;

Column 77,
Line 53, replace "be" with -- by --;

Column 84,
Line 45, replace "this" with -- these --;

Column 88,
Line 64, replace "T" with -- I --;

Column 89,
Line 12, replace "T" with -- I --;
Line 17, replace "199" with -- 190 --;
Line 53, replace "Kee-Wah-Din (R)" with -- Kee-Wah-Din (H) --.

Signed and Sealed this

Eighth Day of October, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
      (A) LENGTH: 8743 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
CGATAAACAT AACAACAGAA TCTGCATTGC AGTAATATTC CTTGAATATA ATTGCAACGC      60

AATGGCCCTC TCTTATAGGC CTGCTGTTGA AGAGGTGCTC GCAAAATTCA CCTCTGATGA     120

ACAATCCAGG GTTTCTGCTA CAGCTCTCAA GGCATTAGTA GACTTAGAGG AAAGTCAGCA     180

CAATTTGTTC TCTTTCGCAT TGCCTGATAG AAGCAAAGAA AGGCTGATAT CTTCTGGCAT     240

TTACTTAAGT CCTTACAGTT TCAGACCCCA CTCACATCCA GTTTGTAAAA CTTTAGAAAA     300

TCACATTTTG TACAATGTTT TACCTAGTTA TGTTAATAAT TCATTTTACT TTGTAGGAAT     360

CAAGGATTTT AAGCTGCAGT TCTTGAAAAG GAGGAATAAG GATCTCAGCT TGGTAGCACT     420

CATAAATAGG TTTGTGACAA GTCGTGATGT TAGTAGGTAT GGGTCTGAGT TCGTTATAAG     480

TTCTAGTGAC AAATCAAGTC AGGTTGTCAG TAGAAAGGGC ATTGGTGATT CTAACACACT     540
```

-continued

```
CCGGAGATTG GTCCCACGTG TAATTTCCAC AGGTGCCAGG AATCTTTTTC TGCATGATGA    600
GATTCACTAC TGGTCAATTA GTGATCTGAT CAATTTTTTG GACGTTGCCA AGCCAAGCAT    660
GCTCTTGGCA ACTGCAGTAA TCCCTCCAGA AGTGCTGGTT GGCTCTCCAG AGAGTCTTAA    720
CCCTTGGGCC TACCAGTATA AAATCAATGG CAACCAACTG CTCTTCGCAC AGATGGCAA     780
CTGGAATGAG ATGTACTCAC AACCTTTGTC ATGCAGATAC CTGCTCAAGG CCAGATCTGT    840
AGTTCTGCCC GATGGCTCAC GCTACTCGGT TGACATCATT CACTCAAAAT TTAGTCACCA    900
CTTGCTTAGT TTCACCCCTA TGGGTAATCT TTTGACTTCA AACATGCGAT GTTTTTCTGG    960
CTTCGATGCA ATAGGCATAA AAGATCTTGA ACCTCTAAGC CGCGGCATGC ACAGTTGCTT   1020
CCCAGTACAT CATGATGTTG TAACTAAGAT ATATCTTTAT TTGAGAACTC TCAAGAAGCC   1080
AGATAAGGAG TCTGCCGAGG CAAAGCTTCG ACAACTCATA GAAAAACCCA CAGGGAGGGA   1140
GATAAAGTTT ATCGAGGATT TTTCCTCACT AGTAATAAAT TGTGGGAGGA GTGGCTCTTT   1200
GCTTATGCCC AACATTTCTA AGTTGGTCAT ATCATTCTTT TGCCGGATGA TGCCAAATGC   1260
ACTCGCCAGG CTCTCTTCTA GCTTTCGAGA GTGTTCGCTA GATTCATTTG TGTACTCACT   1320
TGAGCCCTTT AATTTTTCCG TTAATTTAGT GGATATAACT CCTGATTTCT TTGAGCATTT   1380
ATTTCTCTTC TCCTGCCTAA ATGAGTTGAT CGAGGAGGAC GTTGAAGAGG TCATGGACAA   1440
TTCTTGGTTT GGACTTGGGG ACTTACAATT CAATCGCCAG AGGGCCCCGT TCTTTCTTGG   1500
GTCTTCATAT TGGCTCAACT CCAAATTTTC AGTTGAGCAC AAGTTTTCAG GCACCATCAA   1560
TTCTCAAATC ATGCAAGTTA TTTTATCTTT GATCCCATTT TCTGATGATC CCACTTTTAG   1620
GCCATCTTCT ACAGAGGTTA ACCTTGCACT ATCAGAGGTT AAGGCTGCGC TAGAAGCTAC   1680
TGGGCAGTCA AAATTGTTCA GGTTTTTGGT GGACGACTGT GCTATGCGTG AGGTTAGAAG   1740
TTCCTATAAG GTGGGCCTTT TTAAGCACAT AAAAGCCCTC ACTCATTGCT TTAATTCTTG   1800
TGGCCTCCAA TGGTTCCTCC TTAGGCAAAG GTCCAACCTC AAATTTCTGA AGGACAGGGC   1860
ATCGTCCTTT GCTGATCTTG ATTGTGAGGT TATCAAAGTT TATCAGCTTG TAACATCACA   1920
GGCAATACTT CCTGAGGCTC TGCTTAGCTT GACCAAAGTC TTTGTCAGGG ATTCTGACTC   1980
AAAGGGTGTT TCCATTCCCA GATTGGTCTC GAGAAATGAG CTAGAGGAAC TAGCTCACCC   2040
AGCTAATTCA GCCCTTGAGG AGCCTCAATC AGTTGATTGT AATGCAGGCA GGGTTCAAGC   2100
AAGCGTTTCA AGTTCCCAGC AGCTTGCCGA CACCCACTCT CTTGGTAGCG TTAAGTCATC   2160
AATTGAGACA GCTAACAAGG CTTTTAACTT GGAGGAGCTA AGGATCATGA TTAGAGTCTT   2220
GCCGGAGGAT TTTAACTGGG TGGCGAAGAA CATTGGTTTT AAAGACAGGC TGAGAGGCAG   2280
GGGTGCATCA TTCTTCTCAA AACCAGGAAT TTCATGTCAT AGTTACAATG GTGGGAGCCA   2340
CACAAGCTTA GGGTGGCCAA AGTTCATGGA TCAGATTCTA AGCTCCACTG GTGGACGTAA   2400
TTACTACAAT TCATGCCTGG CTCAGATCTA TGAGGAAAAT TCAAAATTGG CTCTTCATAA   2460
GGATGATGAG AGTTGCTATG AAATTGGGCA CAAAGTTTTG ACTGTTAATT TAATCGGCTC   2520
AGCAACTTTC ACTATTAGTA AGTCGCGAAA TTTGGTTGGG GGTAATCATT GCAGCCTGAC   2580
AATTGGGCCA AATGAGTTTT TCGAAATGCC TAGGGGCATG CAATGCAATT ACTTCCATGG   2640
GGTTTCCAAT TGTACGCCAG GGCGGGTATC GCTGACCTTT AGGCGCCAAA AGTTGGAAGA   2700
TGATGATTTG ATCTTCATAA ATCCACAGGT GCCCATTGAG CTCAATCATG AAAAGCTTGA   2760
CCGAAGTATG TGGCAGATGG GCCTTCATGG AATTAAGAAA TCTATTTCTA TGAATGGCAC   2820
GAGTTTTACC TCAGACCTAT GCTCTTGTTT CTCTTGCCAC AACTTTCATA AATTCAAGGA   2880
```

-continued

```
TCTCATCAAT AACTTGAGAT TGGCCCTAGG AGCACAAGGG CTAGGTCAGT GTGACAGGGT    2940
TGTGTTTGCA ACAACAGGTC CTGGTCTATC TAAGGTTTTA GAAATGCCTC GGAGCAAAAA    3000
GCAATCAATT TTGGTTCTTG AAGGTGCCCT ATCCATAGAA ACAGATTATG GTCCAAAAGT    3060
CCTGGGGTCT TTTGAAGTTT TCAAAGGGGA CTTTCACATT AAGAAGATGG AGGAAGGTTC    3120
AATTTTTGTA ATAACGTACA AGGCCCCAAT TAGATCCACT GGCAGGTTGA GGGTTCACAG    3180
TTCAGAATGC TCATTTTCCG GATCCAAAGA GGTATTGCTA GGCTGCCAGA TTGAGGCATG    3240
TGCTGATTAT GATATTGATG ATTTTAACAC TTTCTCTGTG CCTGGTGATG GCAATTGCTT    3300
TTGGCATTCT GTTGGTTTTT TACTTAGCAC TGATGGACTT GCCCTAAAGG CCGGTATTCG    3360
ATCTTTCGTG GAGAGTGAGC GCTTGGTAAG TCCAGATCTT TCAGCCCCAG CAATTTCTAA    3420
ACAATTGGAA GAGAATGCTT ATGCCGAGAA TGAGATGATC GCATTATTCT GCATTCGGCA    3480
CCACGTAAGG CCTATAGTGA TCACACCAGA ATATGAAGTT AGTTGGAAAT TCGGGGAAGG    3540
TGAGTGGCCC CTATGTGGAA TTCTTTGCCT TAAATCAAAT CACTTCCAAC CATGCGCCCC    3600
ACTGAATGGT TGCATGATCA CAGCCATTGC TTCAGCACTT GGAAGGCGTG AAGTTGATGT    3660
GTTAAATTAT CTGTGTAGAC CCAGCACTAA TCATATTTTT GAGGAGCTTT GTCAGGGAGG    3720
GGGCCTTAAC ATGATGTATT TAGCTGAAGC TTTTGAGGCC TTTGACATTT GCGCTAAATG    3780
TGATATAAAT GGAGAGATTG AAGTGATTAA TCCGTGTGGT AAAATTTCTG CATTGTTTGA    3840
CATAACTAAT GAGCACATAA GGCATGTTGA GAAATAGGT AATGGCCCTC AGAGCATAAA    3900
AGTGGATGAA TTGCGGAAGG TCAAGCGATC CGCCCTCGAT TTCCTTTCAA TGAATGGGTC    3960
TAAAATAACC TACTTCCCAA GCTTTGAGCG GGCTGAAAAG TTGCAAGGAT GTTTGCTAGG    4020
GGGCCTAACT GGCGTTATAA GTGATGAGAA GTTCAGTGAT GCAAAACCTT GGCTTTCTGG    4080
TATATCTACT ACTGATATTA AGCCAAGGGA ATTGACTGTC GTGCTTGGTA CATTTGGGGC    4140
TGGGAAGAGT TTCTTGTACA AGAGTTTCAT GAAAAGGTCT GAGGGTAAAT TCGTAACCTT    4200
TGTTTCTCCC AGACGTGCTT TAGCAAATTC AATCAAAAAT GATCTTGAAA TGGATGATAG    4260
CTGCAAAGTT GCTAAAGCAG GTAGGTCAAA GAAGGAAGGG TGGGATGTAG TAACTTTTGA    4320
GGTTTTCCTT AGAAAAGTTG CAGGATTGAA GGCTGGCCAC TGTGTGATTT TTGATGAGGT    4380
CCAGTTGTTT CCTCCTGGAT ACATCGATCT ATGCTTGCTT ATTATACGTA GTGATGCTTT    4440
CATTTCACTT GCTGGTGATC CATGTCAAAG CACATATGAC TCGCAAAAGG ATCGGGCAAT    4500
TTTGGGCGCT GAGCAGAGTG ACATACTTAG ACTGCTTGAG GGCAAAACGT ATAGGTATAA    4560
CATAGAAAGC AGGAGGTTTG TGAACCCAAT GTTCGAATCA AGACTGCCAT GTCACTTCAA    4620
AAAGGGCTCG ATGACTGCCG CTTTCGCTGA TTATGCAATC TTCCATAATA TGCATGACTT    4680
TCTCCTGGCG AGGTCAAAAG GTCCCTTGGA TGCCGTTTTG GTTTCCAGTT TGAGGAGAA    4740
AAAGATAGTC CAGTCCTACT TTGGAATGAA ACAGCTCACA CTCACATTTG GTGAATCAAC    4800
TGGGTTGAAT TTCAAAAATG GGGAATTCT CATATCACAT GATTCCTTTC ACACAGATGA    4860
TCGGCGGTGG CTTACTGCTT TATCTCGCTT CAGCCACAAT TTGGATTTGG TGAACATCAC    4920
AGGTCTGAGG GTGGAAAGTT TTCTCTCGCA CTTTGCTGGC AAACCCCTCT ACCATTTTTT    4980
AACAGCCAAA AGTGGGGAGA ATGTCATACG AGATTTGCTC CCAGGTGAGC CTAACTTCTT    5040
CAGTGGCTTT AACGTTAGCA TTGGAAAGAA TGAAGGTGTT AGGGAGGAGA AGTTATGTGG    5100
TGACCCATGG TTAAAAGTTA TGCTTTTCCT GGGTCAAGAT GAGGATTGTG AAGTTGAAGA    5160
GATGGAGTCA GAATGCTCAA ATGAAGAATG GTTTAAAACC CACATCCCCT TGAGTAATCT    5220
GGAGTCAACC AGGGCCAGGT GGGTGGGTAA AATGGCCTTG AAAGAGTATC GGGAGGTGCG    5280
```

```
TTGTGGTTAT GAAATGACTC AACAATTCTT TGATGAGCAT AGGGGTGGAA CTGGTGAGCA    5340

ACTGAGCAAT GCATGTGAGA GGTTTGAAAG CATTTACCCA AGGCATAAAG GAAATGATTC    5400

AATAACCTTC CTCATGGCTG TCCGAAAGCG TCTCAAATTT TCGAAGCCCC AGGTTGAAGC    5460

TGCCAAACTG AGGCGGGCCA AACCATATGG GAAATTCTTA TTAGATTCTT CCTATCCAA     5520

AATCCCATTG AAAGCCAGTC ATAATTCCAT CATGTTTCAT GAAGCGGTAC AGGAGTTTGA    5580

GGCGAAGAAG GCTAGTAAGA GTGCAGCAAC TATAGAGAAT CATGCAGGTA GGTCATGCAG    5640

GGATTGGTTA TTAGATGTTG CTCTGATTTT TATGAAGTCA CAACACTGTA CTAAATTTGA    5700

CAACAGGCTT AGAGTAGCTA AAGCTGGGCA AACCCTTGCT TGCTTCCAAC ATGCTGTTCT    5760

GGTTCGCTTT GCACCCTATA TGAGATACAT TGAGAAAAAG CTAATGCAAG CTCTGAAGCC    5820

TAACTTCTAC ATCCATTCAG GGAAAGGTCT GACGAGCTGA ACGAGTGGGT CAGAACTAGA    5880

GGATTCACTG GAATTTGCAC AGAATCAGAC TACGAAGCCT TGATGCTTC CCAAGACCAC     5940

TTCATCCTAG CATTCGAATT GCAGATAATG AAATTTTTGG GGTTACCTGA AGATTTAATT    6000

TTGGACTATG AATTCATAAA AATTCATTTG GGATCAAAGC TCGGATCATT CTCTATAATG    6060

AGGTTTACTG GGGAGGCCAG CACATTTCTG TTTAACACTA TGGCTAACAT GTTGTTCACC    6120

TTTCTGAGGT ACGAACTAAC AGGCTCTGAG TCAATAGCAT TTGCAGGTGA TGACATGTGT    6180

GCTAATCGAA GGTTGCGGCT TAAAACAGAG CATGAGGGTT TTCTGAACAT GATTTGCCTT    6240

AAGGCCAAGG TTCAGTTTGT TTCCAATCCC ACATTCTGCG GATGGTGTTT ATTTAAGGAA    6300

GGGATCTTCA AGAAGCCTCA ATTAATCTGG GAGCGGATAT GCATTGCTAG GGAGATGGGC    6360

AACCTGGAGA ATTGTATTGA CAATTATGCG ATAGAGGTCT CCTATGCATA CCGACTGGGA    6420

GAGCTAGCCA TTGAAATGAT GACCGAGGAA GAAGTGGAGG CCCATTATAA TTGTGTTAGA    6480

TTCTTGGTCA GGAACAAGCA TAAGATGAGA TGCTCAATTT CAGGCCTATT TGAAGCTATT    6540

GATTAGGCCT TAAGTATTTG GCATTATTTG AGTATTATGA ATAATTTAGT TAAAGCATTG    6600

TCAGCATTTG AGTTTGTAGG TGTTTTCAGT GTGCTTAAAT TTCCAGTAGT CATTCATAGT    6660

GTGCCTGGTA GTGGTAAAAG TAGTTTAATA AGGGAGCTAA TTTCCGAGGA TGAGAATTTC    6720

ATAGCTTTCA CAGCAGGTGT TCCAGACAGC CCTAATCTCA CAGGAAGGTA CATTAAGCCT    6780

TATTCTCCAG GGTGTGCAGT GCCAGGGAAA GTTAATATAC TTGATGAGTA CTTGTCCGTC    6840

CAAGATTTTT CAGGTTTTGA TGTGCTGTTC TCGGACCCAT ACCAAAACAT CAGCATTCCT    6900

AAAGAGGCAC ATTTCATCAA GTCAAAAACT TGTAGGTTTG GCGTGAATAC TTGCAAATAT    6960

CTTTCCTCCT TCGGTTTTAA GGTTAGCAGT GACGGTTTGG ACAAAGTCAT TGTGGGGTCG    7020

CCTTTTACAC TAGATGTTGA AGGGGTGCTA ATATGCTTTG GTAAGGAGGC AGTGGATCTC    7080

GCTGTTGCGC ACAACTCTGA ATTCAAATTA CCTTGTGAAG TTAGAGGTTC AACTTTTAAC    7140

GTCGTAACTC TTTTGAAATC AAGAGATCCA ACCCCAGAGG ATAGGCACTG GTTTTACATT    7200

GCTGCTACAA GACACAGGGA GAAATTGATA ATCATGCAGT AAGATGCCTT TTCAGCAGCC    7260

TGCGAATTGG GCAAAAACCA TAACTCCATT GACAGTTGGC TTGGGCATTG GCTTGTGCT     7320

GCATTTCTG AGGAAGTCAA ATCTACCTTA TTCAGGGGAC AACATCCATC AATTCCCTCA     7380

CGGTGGGCGT TACAGGGACG GTACAAAAAG TATAACTTAC TGTGGTCCAA AGCAATCCTT    7440

CCCCAGCTCT GGGATATTCG GCCAATCTGA GAATTTTGTG CCCTTAATGC TTGTCATAGG    7500

TCTAATCGCA TTCATACATG TATTGTCTGT TTGGAATTCT GGTCTTGGTA GGAATTGTAA    7560

TTGCCATCCA AATCCTTGCT CATGTAGACA GCAGTAGTGG CAACCACCAA GGTTGCTTCA    7620
```

```
TTAGGGCCAC TGGAGAGTCA ATTTTGATTG AAAACTGCGG CCCAAGTGAG GCCCTTGCAT      7680

CCACTGTGAA GGAGGTGCTG GGAGGTTTGA AGGCTTTAGG GGTTAGCCGT GCTGTTGAAG      7740

AAATTGATTA TCATTGTTAA ATTGGCTGAA TGGCAAGTCA AATTGGGAAA CTCCCCGGTG      7800

AATCAAATGA GGCTTTTGAA GCCCGGCTAA AATCGCTGGA GTTAGCTAGA GCTCAAAAGC      7860

AGCCGGAAGG TTCTAATGCA CCACCTACTC TCAGTGGCAT TCTTGCCAAA CGCAAGAGGA      7920

TTATAGAGAA TGCACTTTCA AAGACGGTGG ACATGAGGGA GGTTTTGAAA CACGAAACGG      7980

TGGTGATTTC CCCAAATGTC ATGGATGAAG GTGCAATAGA CGAGCTGATT CGTGCATTTG      8040

GTGAATCTGG CATAGCTGAA AGCGTGCAAT TTGATGTGGC CATAGATATA GCACGTCACT      8100

GCTCTGATGT TGGTAGCTCC CAGAGGTCAA CCCTGATTGG CAAGAGTCCA TTTTGTGACC      8160

TAAACAGATC AGAAATAGCT GGGATTATAA GGGAGGTGAC CACATTACGT AGATTTTGCA      8220

TGTACTATGC AAAAATCGTG TGGAACATCC ATCTGGAGAC GGGGATACCA CCAGCTAACT      8280

GGGCCAAGAA AGGATTTAAT GAGAATGAAA AGTTTGCAGC CTTTGATTTT TTCTTGGGAG      8340

TCACAGATGA GAGTGCGCTT GAACCAAAGG GTGGAATTAA AAGAGCTCCA ACGAAAGCTG      8400

AGATGGTTGC TAATATCGCC TCTTTTGAGG TTCAAGTGCT CAGACAAGCT ATGGCTGAAG      8460

GCAAGCGGAG TTCCAACCTT GGAGAGATTA GTGGTGGAAC GGCTGGTGCA CTCATCAACA      8520

ACCCCTTTTC AAATGTTACA CATGAATGAG GATGACGAAG TCAGCGACAA TTCCGCAGTC      8580

CAATAATTCC CCGATTTCAA GGCTGGGTTA AGCCTGTTCG CTGGAATACC GTACTAATAG      8640

TATTCCCTTT CCATGCTAAA TCCTATTTAA TATATAAGGT GTGGAAAGTA AAGAAGATT      8700

TGGTGTGTTT TTATAGTTTT CATTCAAAAA AAAAAAAAA AAA                        8743

(2) INFORMATION FOR SEQ ID NO:2:

(i) SEQUENCE CHARACTERISTICS:
        (A) LENGTH: 6485 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

ATGGCCCTCT CTTATAGGCC TGCTGTTGAA GAGGTGCTCG CAAAATTCAC CTCTGATGAA        60

CAATCCAGGG TTTCTGCTAC AGCTCTCAAG GCATTAGTAG ACTTAGAGGA AAGTCAGCAC       120

AATTTGTTCT CTTTCGCATT GCCTGATAGA AGCAAAGAAA GGCTGATATC TTCTGGCATT       180

TACTTAAGTC CTTACAGTTT CAGACCCCAC TCACATCCAG TTTGTAAAAC TTTAGAAAAT       240

CACATTTTGT ACAATGTTTT ACCTAGTTAT GTTAATAATT CATTTTACTT TGTAGGAATC       300

AAGGATTTTA AGCTGCAGTT CTTGAAAAGG AGGAATAAGG ATCTCAGCTT GGTAGCACTC       360

ATAAATAGGT TTGTGACAAG TCGTGATGTT AGTAGGTATG GGTCTGAGTT CGTTATAAGT       420

TCTAGTGACA AATCAAGTCA GGTTGTCAGT AGAAAGGGCA TTGGTGATTC TAACACACTC       480

CGGAGATTGG TCCCACGTGT AATTTCCACA GGTGCCAGGA ATCTTTTTCT GCATGATGAG       540

ATTCACTACT GGTCAATTAG TGATCTGATC AATTTTTTGG ACGTTGCCAA GCCAAGCATG       600

CTCTTGGCAA CTGCAGTAAT CCCTCCAGAA GTGCTGGTTG GCTCTCCAGA GAGTCTTAAC       660

CCTTGGGCCT ACCAGTATAA AATCAATGGC AACCAACTGC TCTTCGCACC AGATGGCAAC       720

TGGAATGAGA TGTACTCACA ACCTTTGTCA TGCAGATACC TGCTCAAGGC CAGATCTGTA       780

GTTCTGCCCG ATGGCTCACG CTACTCGGTT GACATCATTC ACTCAAAATT TAGTCACCAC       840
```

-continued

```
TTGCTTAGTT TCACCCCTAT GGGTAATCTT TTGACTTCAA ACATGCGATG TTTTTCTGGC    900
TTCGATGCAA TAGGCATAAA AGATCTTGAA CCTCTAAGCC GCGGCATGCA CAGTTGCTTC    960
CCAGTACATC ATGATGTTGT AACTAAGATA TATCTTTATT TGAGAACTCT CAAGAAGCCA   1020
GATAAGGAGT CTGCCGAGGC AAAGCTTCGA CAACTCATAG AAAAACCCAC AGGGAGGGAG   1080
ATAAAGTTTA TCGAGGATTT TTCCTCACTA GTAATAAATT GTGGGAGGAG TGGCTCTTTG   1140
CTTATGCCCA ACATTTCTAA GTTGGTCATA TCATTCTTTT GCCGGATGAT GCCAAATGCA   1200
CTCGCCAGGC TCTCTTCTAG CTTTCGAGAG TGTTCGCTAG ATTCATTTGT GTACTCACTT   1260
GAGCCCTTTA ATTTTTCCGT TAATTTAGTG GATATAACTC CTGATTTCTT TGAGCATTTA   1320
TTTCTCTTCT CCTGCCTAAA TGAGTTGATC GAGGAGGACG TTGAAGAGGT CATGGACAAT   1380
TCTTGGTTTG GACTTGGGGA CTTACAATTC AATCGCCAGA GGGCCCCGTT CTTTCTTGGG   1440
TCTTCATATT GGCTCAACTC CAAATTTTCA GTTGAGCACA AGTTTTCAGG CACCATCAAT   1500
TCTCAAATCA TGCAAGTTAT TTTATCTTTG ATCCCATTTT CTGATGATCC CACTTTTAGG   1560
CCATCTTCTA CAGAGGTTAA CCTTGCACTA TCAGAGGTTA AGGCTGCGCT AGAAGCTACT   1620
GGGCAGTCAA AATTGTTCAG GTTTTTGGTG GACGACTGTG CTATGCGTGA GGTTAGAAGT   1680
TCCTATAAGG TGGGCCTTTT TAAGCACATA AAAGCCCTCA CTCATTGCTT TAATTCTTGT   1740
GGCCTCCAAT GGTTCCTCCT TAGGCAAAGG TCCAACCTCA AATTTCTGAA GGACAGGGCA   1800
TCGTCCTTTG CTGATCTTGA TTGTGAGGTT ATCAAAGTTT ATCAGCTTGT AACATCACAG   1860
GCAATACTTC CTGAGGCTCT GCTTAGCTTG ACCAAAGTCT TTGTCAGGGA TTCTGACTCA   1920
AAGGGTGTTT CCATTCCCAG ATTGGTCTCG AGAAATGAGC TAGAGGAACT AGCTCACCCA   1980
GCTAATTCAG CCCTTGAGGA GCCTCAATCA GTTGATTGTA ATGCAGGCAG GGTTCAAGCA   2040
AGCGTTTCAA GTTCCCAGCA GCTTGCCGAC ACCCACTCTC TTGGTAGCGT TAAGTCATCA   2100
ATTGAGACAG CTAACAAGGC TTTTAACTTG GAGGAGCTAA GGATCATGAT TAGAGTCTTG   2160
CCGGAGGATT TTAACTGGGT GGCGAAGAAC ATTGGTTTTA AAGACAGGCT GAGAGGCAGG   2220
GGTGCATCAT TCTTCTCAAA ACCAGGAATT TCATGTCATA GTTACAATGG TGGGAGCCAC   2280
ACAAGCTTAG GGTGGCCAAA GTTCATGGAT CAGATTCTAA GCTCCACTGG TGGACGTAAT   2340
TACTACAATT CATGCCTGGC TCAGATCTAT GAGGAAAATT CAAAATTGGC TCTTCATAAG   2400
GATGATGAGA GTTGCTATGA AATTGGGCAC AAAGTTTTGA CTGTTAATTT AATCGGCTCA   2460
GCAACTTTCA CTATTAGTAA GTCGCGAAAT TTGGTTGGGG GTAATCATTG CAGCCTGACA   2520
ATTGGGCCAA ATGAGTTTTT CGAAATGCCT AGGGGCATGC AATGCAATTA CTTCCATGGG   2580
GTTTCCAATT GTACGCCAGG GCGGGTATCG CTGACCTTTA GGCGCCAAAA GTTGGAAGAT   2640
GATGATTTGA TCTTCATAAA TCCACAGGTG CCCATTGAGC TCAATCATGA AAAGCTTGAC   2700
CGAAGTATGT GGCAGATGGG CCTTCATGGA ATTAAGAAAT CTATTTCTAT GAATGGCACG   2760
AGTTTTACCT CAGACCTATG CTCTTGTTTC TCTTGCCACA ACTTTCATAA ATTCAAGGAT   2820
CTCATCAATA ACTTGAGATT GGCCCTAGGA GCACAAGGGC TAGGTCAGTG TGACAGGGTT   2880
GTGTTTGCAA CAACAGGTCC TGGTCTATCT AAGGTTTTAG AAATGCCTCG GAGCAAAAAG   2940
CAATCAATTT TGGTTCTTGA AGGTGCCCTA TCCATAGAAA CAGATTATGG TCCAAAAGTC   3000
CTGGGGTCTT TTGAAGTTTT CAAAGGGGAC TTTCACATTA AGAAGATGGA GGAAGGTTCA   3060
ATTTTTGTAA TAACGTACAA GGCCCCAATT AGATCCACTG GCAGGTTGAG GGTTCACAGT   3120
TCAGAATGCT CATTTTCCGG ATCCAAAGAG GTATTGCTAG GCTGCCAGAT TGAGGCATGT   3180
GCTGATTATG ATATTGATGA TTTTAACACT TTCTCTGTGC CTGGTGATGG CAATTGCTTT   3240
```

```
TGGCATTCTG TTGGTTTTTT ACTTAGCACT GATGGACTTG CCCTAAAGGC CGGTATTCGA    3300

TCTTTCGTGG AGAGTGAGCG CTTGGTAAGT CCAGATCTTT CAGCCCCAGC AATTTCTAAA    3360

CAATTGGAAG AGAATGCTTA TGCCGAGAAT GAGATGATCG CATTATTCTG CATTCGGCAC    3420

CACGTAAGGC CTATAGTGAT CACACCAGAA TATGAAGTTA GTTGGAAATT CGGGGAAGGT    3480

GAGTGGCCCC TATGTGGAAT TCTTTGCCTT AAATCAAATC ACTTCCAACC ATGCGCCCCA    3540

CTGAATGGTT GCATGATCAC AGCCATTGCT TCAGCACTTG GAAGGCGTGA AGTTGATGTG    3600

TTAAATTATC TGTGTAGACC CAGCACTAAT CATATTTTTG AGGAGCTTTG TCAGGGAGGG    3660

GGCCTTAACA TGATGTATTT AGCTGAAGCT TTTGAGGCCT TTGACATTTG CGCTAAATGT    3720

GATATAAATG GAGAGATTGA AGTGATTAAT CCGTGTGGTA AAATTTCTGC ATTGTTTGAC    3780

ATAACTAATG AGCACATAAG GCATGTTGAG AAAATAGGTA ATGGCCCTCA GAGCATAAAA    3840

GTGGATGAAT TGCGGAAGGT CAAGCGATCC GCCCTCGATT TCCTTTCAAT GAATGGGTCT    3900

AAAATAACCT ACTTCCCAAG CTTTGAGCGG GCTGAAAAGT TGCAAGGATG TTTGCTAGGG    3960

GGCCTAACTG GCGTTATAAG TGATGAGAAG TTCAGTGATG CAAAACCTTG GCTTTCTGGT    4020

ATATCTACTA CTGATATTAA GCCAAGGGAA TTGACTGTCG TGCTTGGTAC ATTTGGGGCT    4080

GGGAAGAGTT TCTTGTACAA GAGTTTCATG AAAAGGTCTG AGGGTAAATT CGTAACCTTT    4140

GTTTCTCCCA GACGTGCTTT AGCAAATTCA ATCAAAAATG ATCTTGAAAT GGATGATAGC    4200

TGCAAAGTTG CTAAAGCAGG TAGGTCAAAG AAGGAAGGGT GGGATGTAGT AACTTTTGAG    4260

GTTTTCCTTA GAAAAGTTGC AGGATTGAAG GCTGGCCACT GTGTGATTTT TGATGAGGTC    4320

CAGTTGTTTC CTCCTGGATA CATCGATCTA TGCTTGCTTA TTATACGTAG TGATGCTTTC    4380

ATTTCACTTG CTGGTGATCC ATGTCAAAGC ACATATGACT CGCAAAAGGA TCGGGCAATT    4440

TTGGGCGCTG AGCAGAGTGA CATACTTAGA CTGCTTGAGG GCAAAACGTA TAGGTATAAC    4500

ATAGAAAGCA GGAGGTTTGT GAACCCAATG TTCGAATCAA GACTGCCATG TCACTTCAAA    4560

AAGGGCTCGA TGACTGCCGC TTTCGCTGAT TATGCAATCT TCCATAATAT GCATGACTTT    4620

CTCCTGGCGA GGTCAAAAGG TCCCTTGGAT GCCGTTTTGG TTTCCAGTTT TGAGGAGAAA    4680

AAGATAGTCC AGTCCTACTT TGGAATGAAA CAGCTCACAC TCACATTTGG TGAATCAACT    4740

GGGTTGAATT TCAAAAATGG GGGAATTCTC ATATCACATG ATTCCTTTCA CACAGATGAT    4800

CGGCGGTGGC TTACTGCTTT ATCTCGCTTC AGCCACAATT TGGATTTGGT GAACATCACA    4860

GGTCTGAGGG TGGAAAGTTT TCTCTCGCAC TTTGCTGGCA AACCCCTCTA CCATTTTTTA    4920

ACAGCCAAAA GTGGGGAGAA TGTCATACGA GATTTGCTCC CAGGTGAGCC TAACTTCTTC    4980

AGTGGCTTTA ACGTTAGCAT TGGAAAGAAT GAAGGTGTTA GGGAGGAGAA GTTATGTGGT    5040

GACCCATGGT TAAAAGTTAT GCTTTTCCTG GGTCAAGATG AGGATTGTGA AGTTGAAGAG    5100

ATGGAGTCAG AATGCTCAAA TGAAGAATGG TTTAAAACCC ACATCCCCTT GAGTAATCTG    5160

GAGTCAACCA GGGCCAGGTG GGTGGGTAAA ATGGCCTTGA AGAGTATCG GGAGGTGCGT    5220

TGTGGTTATG AAATGACTCA ACAATTCTTT GATGAGCATA GGGGTGGAAC TGGTGAGCAA    5280

CTGAGCAATG CATGTGAGAG GTTTGAAAGC ATTTACCCAA GGCATAAAGG AAATGATTCA    5340

ATAACCTTCC TCATGGCTGT CCGAAAGCGT CTCAAATTTT CGAAGCCCCA GGTTGAAGCT    5400

GCCAAACTGA GGCGGGCCAA ACCATATGGG AAATTCTTAT TAGATTCTTT CCTATCCAAA    5460

ATCCCATTGA AAGCCAGTCA TAATTCCATC ATGTTTCATG AAGCGGTACA GGAGTTTGAG    5520

GCGAAGAAGG CTAGTAAGAG TGCAGCAACT ATAGAGAATC ATGCAGGTAG GTCATGCAGG    5580
```

```
GATTGGTTAT TAGATGTTGC TCTGATTTTT ATGAAGTCAC AACACTGTAC TAAATTTGAC      5640

AACAGGCTTA GAGTAGCTAA AGCTGGGCAA ACCCTTGCTT GCTTCCAACA TGCTGTTCTG      5700

GTTCGCTTTG CACCCTATAT GAGATACATT GAGAAAAAGC TAATGCAAGC TCTGAAGCCT      5760

AACTTCTACA TCCATTCAGG GAAAGGTCTG ACGAGCTGAA CGAGTGGGTC AGAACTAGAG      5820

GATTCACTGG AATTTGCACA GAATCAGACT ACGAAGCCTT TGATGCTTCC CAAGACCACT      5880

TCATCCTAGC ATTCGAATTG CAGATAATGA AATTTTTGGG GTTACCTGAA GATTTAATTT      5940

TGGACTATGA ATTCATAAAA ATTCATTTGG GATCAAAGCT CGGATCATTC TCTATAATGA      6000

GGTTTACTGG GGAGGCCAGC ACATTTCTGT TTAACACTAT GGCTAACATG TTGTTCACCT      6060

TTCTGAGGTA CGAACTAACA GGCTCTGAGT CAATAGCATT TGCAGGTGAT GACATGTGTG      6120

CTAATCGAAG GTTGCGGCTT AAAACAGAGC ATGAGGGTTT TCTGAACATG ATTTGCCTTA      6180

AGGCCAAGGT TCAGTTTGTT TCCAATCCCA CATTCTGCGG ATGGTGTTTA TTTAAGGAAG      6240

GGATCTTCAA GAAGCCTCAA TTAATCTGGG AGCGGATATG CATTGCTAGG GAGATGGGCA      6300

ACCTGGAGAA TTGTATTGAC AATTATGCGA TAGAGGTCTC CTATGCATAC CGACTGGGAG      6360

AGCTAGCCAT TGAAATGATG ACCGAGGAAG AAGTGGAGGC CCATTATAAT TGTGTTAGAT      6420

TCTTGGTCAG GAACAAGCAT AAGATGAGAT GCTCAATTTC AGGCCTATTT GAAGCTATTG      6480

ATTAG                                                                 6485

(2) INFORMATION FOR SEQ ID NO:3:

(i) SEQUENCE CHARACTERISTICS:
        (A) LENGTH: 2161 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

Met Ala Leu Ser Tyr Arg Pro Ala Val Glu Glu Val Leu Ala Lys Phe
    1               5                   10                  15

Thr Ser Asp Glu Gln Ser Arg Val Ser Ala Thr Ala Leu Lys Ala Leu
                20                  25                  30

Val Asp Leu Glu Glu Ser Gln His Asn Leu Phe Ser Phe Ala Leu Pro
            35                  40                  45

Asp Arg Ser Lys Glu Arg Leu Ile Ser Ser Gly Ile Tyr Leu Ser Pro
        50                  55                  60

Tyr Ser Phe Arg Pro His Ser His Pro Val Cys Lys Thr Leu Glu Asn
    65                  70                  75                  80

His Ile Leu Tyr Asn Val Leu Pro Ser Tyr Val Asn Asn Ser Phe Tyr
                    85                  90                  95

Phe Val Gly Ile Lys Asp Phe Lys Leu Gln Phe Leu Lys Arg Arg Asn
                100                 105                 110

Lys Asp Leu Ser Leu Val Ala Leu Ile Asn Arg Phe Val Thr Ser Arg
                115                 120                 125

Asp Val Ser Arg Tyr Gly Ser Glu Phe Val Ile Ser Ser Asp Lys
        130                 135                 140

Ser Ser Gln Val Val Ser Arg Lys Gly Ile Gly Asp Ser Asn Thr Leu
    145                 150                 155                 160

Arg Arg Leu Val Pro Arg Val Ile Ser Thr Gly Ala Arg Asn Leu Phe
                    165                 170                 175

Leu His Asp Glu Ile His Tyr Trp Ser Ile Ser Asp Leu Ile Asn Phe
```

```
                180                185                190
    Leu Asp Val Ala Lys Pro Ser Met Leu Leu Ala Thr Ala Val Ile Pro
                195                200                205
    Pro Glu Val Leu Val Gly Ser Pro Glu Ser Leu Asn Pro Trp Ala Tyr
                210                215                220
    Gln Tyr Lys Ile Asn Gly Asn Gln Leu Leu Phe Ala Pro Asp Gly Asn
    225                230                235                240
    Trp Asn Glu Met Tyr Ser Gln Pro Leu Ser Cys Arg Tyr Leu Leu Lys
                    245                250                255
    Ala Arg Ser Val Val Leu Pro Asp Gly Ser Arg Tyr Ser Val Asp Ile
                260                265                270
    Ile His Ser Lys Phe Ser His His Leu Leu Ser Phe Thr Pro Met Gly
                275                280                285
    Asn Leu Leu Thr Ser Asn Met Arg Cys Phe Ser Gly Phe Asp Ala Ile
                290                295                300
    Gly Ile Lys Asp Leu Glu Pro Leu Ser Arg Gly Met His Ser Cys Phe
    305                310                315                320
    Pro Val His His Asp Val Val Thr Lys Ile Tyr Leu Tyr Leu Arg Thr
                    325                330                335
    Leu Lys Lys Pro Asp Lys Glu Ser Ala Glu Ala Lys Leu Arg Gln Leu
                    340                345                350
    Ile Glu Lys Pro Thr Gly Arg Glu Ile Lys Phe Ile Glu Asp Phe Ser
                355                360                365
    Ser Leu Val Ile Asn Cys Gly Arg Ser Gly Ser Leu Leu Met Pro Asn
                370                375                380
    Ile Ser Lys Leu Val Ile Ser Phe Phe Cys Arg Met Met Pro Asn Ala
    385                390                395                400
    Leu Ala Arg Leu Ser Ser Ser Phe Arg Glu Cys Ser Leu Asp Ser Phe
                    405                410                415
    Val Tyr Ser Leu Glu Pro Phe Asn Phe Ser Val Asn Leu Val Asp Ile
                    420                425                430
    Thr Pro Asp Phe Phe Glu His Leu Phe Leu Phe Ser Cys Leu Asn Glu
                435                440                445
    Leu Ile Glu Glu Asp Val Glu Glu Val Met Asp Asn Ser Trp Phe Gly
                450                455                460
    Leu Gly Asp Leu Gln Phe Asn Arg Gln Arg Ala Pro Phe Phe Leu Gly
    465                470                475                480
    Ser Ser Tyr Trp Leu Asn Ser Lys Phe Ser Val Glu His Lys Phe Ser
                    485                490                495
    Gly Thr Ile Asn Ser Gln Ile Met Gln Val Ile Leu Ser Leu Ile Pro
                    500                505                510
    Phe Ser Asp Asp Pro Thr Phe Arg Pro Ser Ser Thr Glu Val Asn Leu
                515                520                525
    Ala Leu Ser Glu Val Lys Ala Ala Leu Glu Ala Thr Gly Gln Ser Lys
                530                535                540
    Leu Phe Arg Phe Leu Val Asp Asp Cys Ala Met Arg Glu Val Arg Ser
    545                550                555                560
    Ser Tyr Lys Val Gly Leu Phe Lys His Ile Lys Ala Leu Thr His Cys
                    565                570                575
    Phe Asn Ser Cys Gly Leu Gln Trp Phe Leu Leu Arg Gln Arg Ser Asn
                    580                585                590
    Leu Lys Phe Leu Lys Asp Arg Ala Ser Ser Phe Ala Asp Leu Asp Cys
                595                600                605
```

```
Glu Val Ile Lys Val Tyr Gln Leu Val Thr Ser Gln Ala Ile Leu Pro
    610                 615                 620
Glu Ala Leu Leu Ser Leu Thr Lys Val Phe Val Arg Asp Ser Asp Ser
625                 630                 635                 640
Lys Gly Val Ser Ile Pro Arg Leu Val Ser Arg Asn Glu Leu Glu Glu
                645                 650                 655
Leu Ala His Pro Ala Asn Ser Ala Leu Glu Glu Pro Gln Ser Val Asp
                660                 665                 670
Cys Asn Ala Gly Arg Val Gln Ala Ser Val Ser Ser Gln Gln Leu
    675                 680                 685
Ala Asp Thr His Ser Leu Gly Ser Val Lys Ser Ser Ile Glu Thr Ala
    690                 695                 700
Asn Lys Ala Phe Asn Leu Glu Glu Leu Arg Ile Met Ile Arg Val Leu
705                 710                 715                 720
Pro Glu Asp Phe Asn Trp Val Ala Lys Asn Ile Gly Phe Lys Asp Arg
                725                 730                 735
Leu Arg Gly Arg Gly Ala Ser Phe Phe Ser Lys Pro Gly Ile Ser Cys
                740                 745                 750
His Ser Tyr Asn Gly Gly Ser His Thr Ser Leu Gly Trp Pro Lys Phe
    755                 760                 765
Met Asp Gln Ile Leu Ser Ser Thr Gly Gly Arg Asn Tyr Tyr Asn Ser
    770                 775                 780
Cys Leu Ala Gln Ile Tyr Glu Glu Asn Ser Lys Leu Ala Leu His Lys
785                 790                 795                 800
Asp Asp Glu Ser Cys Tyr Glu Ile Gly His Lys Val Leu Thr Val Asn
                805                 810                 815
Leu Ile Gly Ser Ala Thr Phe Thr Ile Ser Lys Ser Arg Asn Leu Val
                820                 825                 830
Gly Gly Asn His Cys Ser Leu Thr Ile Gly Pro Asn Glu Phe Phe Glu
                835                 840                 845
Met Pro Arg Gly Met Gln Cys Asn Tyr Phe His Gly Val Ser Asn Cys
    850                 855                 860
Thr Pro Gly Arg Val Ser Leu Thr Phe Arg Arg Gln Lys Leu Glu Asp
865                 870                 875                 880
Asp Asp Leu Ile Phe Ile Asn Pro Gln Val Pro Ile Glu Leu Asn His
                885                 890                 895
Glu Lys Leu Asp Arg Ser Met Trp Gln Met Gly Leu His Gly Ile Lys
                900                 905                 910
Lys Ser Ile Ser Met Asn Gly Thr Ser Phe Thr Ser Asp Leu Cys Ser
    915                 920                 925
Cys Phe Ser Cys His Asn Phe His Lys Phe Lys Asp Leu Ile Asn Asn
    930                 935                 940
Leu Arg Leu Ala Leu Gly Ala Gln Gly Leu Gly Gln Cys Asp Arg Val
945                 950                 955                 960
Val Phe Ala Thr Thr Gly Pro Gly Leu Ser Lys Val Leu Glu Met Pro
                965                 970                 975
Arg Ser Lys Lys Gln Ser Ile Leu Val Leu Glu Gly Ala Leu Ser Ile
                980                 985                 990
Glu Thr Asp Tyr Gly Pro Lys Val Leu Gly Ser Phe Glu Val Phe Lys
    995                 1000                1005
Gly Asp Phe His Ile Lys Lys Met Glu Glu Gly Ser Ile Phe Val Ile
    1010                1015                1020
```

-continued

```
Thr Tyr Lys Ala Pro Ile Arg Ser Thr Gly Arg Leu Arg Val His Ser
1025                1030                1035                1040

Ser Glu Cys Ser Phe Ser Gly Ser Lys Glu Val Leu Leu Gly Cys Gln
            1045                1050                1055

Ile Glu Ala Cys Ala Asp Tyr Asp Ile Asp Asp Phe Asn Thr Phe Ser
                1060                1065                1070

Val Pro Gly Asp Gly Asn Cys Phe Trp His Ser Val Gly Phe Leu Leu
        1075                1080                1085

Ser Thr Asp Gly Leu Ala Leu Lys Ala Gly Ile Arg Ser Phe Val Glu
    1090                1095                1100

Ser Glu Arg Leu Val Ser Pro Asp Leu Ser Ala Pro Ala Ile Ser Lys
1105                1110                1115                1120

Gln Leu Glu Glu Asn Ala Tyr Ala Glu Asn Met Ile Ala Leu Phe
            1125                1130                1135

Cys Ile Arg His His Val Arg Pro Ile Val Ile Thr Pro Glu Tyr Glu
                1140                1145                1150

Val Ser Trp Lys Phe Gly Glu Gly Glu Trp Pro Leu Cys Gly Ile Leu
        1155                1160                1165

Cys Leu Lys Ser Asn His Phe Gln Pro Cys Ala Pro Leu Asn Gly Cys
    1170                1175                1180

Met Ile Thr Ala Ile Ala Ser Ala Leu Gly Arg Arg Glu Val Asp Val
1185                1190                1195                1200

Leu Asn Tyr Leu Cys Arg Pro Ser Thr Asn His Ile Phe Glu Glu Leu
                1205                1210                1215

Cys Gln Gly Gly Gly Leu Asn Met Met Tyr Leu Ala Glu Ala Phe Glu
        1220                1225                1230

Ala Phe Asp Ile Cys Ala Lys Cys Asp Ile Asn Gly Glu Ile Glu Val
    1235                1240                1245

Ile Asn Pro Cys Gly Lys Ile Ser Ala Leu Phe Asp Ile Thr Asn Glu
    1250                1255                1260

His Ile Arg His Val Glu Lys Ile Gly Asn Gly Pro Gln Ser Ile Lys
1265                1270                1275                1280

Val Asp Glu Leu Arg Lys Val Lys Arg Ser Ala Leu Asp Phe Leu Ser
                1285                1290                1295

Met Asn Gly Ser Lys Ile Thr Tyr Phe Pro Ser Phe Glu Arg Ala Glu
        1300                1305                1310

Lys Leu Gln Gly Cys Leu Leu Gly Gly Leu Thr Gly Val Ile Ser Asp
    1315                1320                1325

Glu Lys Phe Ser Asp Ala Lys Pro Trp Leu Ser Gly Ile Ser Thr Thr
    1330                1335                1340

Asp Ile Lys Pro Arg Glu Leu Thr Val Val Leu Gly Thr Phe Gly Ala
1345                1350                1355                1360

Gly Lys Ser Phe Leu Tyr Lys Ser Phe Met Lys Arg Ser Glu Gly Lys
                1365                1370                1375

Phe Val Thr Phe Val Ser Pro Arg Arg Ala Leu Ala Asn Ser Ile Lys
        1380                1385                1390

Asn Asp Leu Glu Met Asp Asp Ser Cys Lys Val Ala Lys Ala Gly Arg
    1395                1400                1405

Ser Lys Lys Glu Gly Trp Asp Val Val Thr Phe Glu Val Phe Leu Arg
    1410                1415                1420

Lys Val Ala Gly Leu Lys Ala Gly His Cys Val Ile Phe Asp Glu Val
1425                1430                1435                1440

Gln Leu Phe Pro Pro Gly Tyr Ile Asp Leu Cys Leu Leu Ile Ile Arg
```

```
                    1445            1450            1455

Ser Asp Ala Phe Ile Ser Leu Ala Gly Asp Pro Cys Gln Ser Thr Tyr
                1460            1465            1470

Asp Ser Gln Lys Asp Arg Ala Ile Leu Gly Ala Glu Gln Ser Asp Ile
                1475            1480            1485

Leu Arg Leu Leu Glu Gly Lys Thr Tyr Arg Tyr Asn Ile Glu Ser Arg
                1490            1495            1500

Arg Phe Val Asn Pro Met Phe Glu Ser Arg Leu Pro Cys His Phe Lys
        1505            1510            1515            1520

Lys Gly Ser Met Thr Ala Ala Phe Ala Asp Tyr Ala Ile Phe His Asn
                    1525            1530            1535

Met His Asp Phe Leu Leu Ala Arg Ser Lys Gly Pro Leu Asp Ala Val
                1540            1545            1550

Leu Val Ser Ser Phe Glu Glu Lys Lys Ile Val Gln Ser Tyr Phe Gly
                1555            1560            1565

Met Lys Gln Leu Thr Leu Thr Phe Gly Glu Ser Thr Gly Leu Asn Phe
            1570            1575            1580

Lys Asn Gly Gly Ile Leu Ile Ser His Asp Ser Phe His Thr Asp Asp
        1585            1590            1595            1600

Arg Arg Trp Leu Thr Ala Leu Ser Arg Phe Ser His Asn Leu Asp Leu
                    1605            1610            1615

Val Asn Ile Thr Gly Leu Arg Val Glu Ser Phe Leu Ser His Phe Ala
                1620            1625            1630

Gly Lys Pro Leu Tyr His Phe Leu Thr Ala Lys Ser Gly Glu Asn Val
                1635            1640            1645

Ile Arg Asp Leu Leu Pro Gly Glu Pro Asn Phe Phe Ser Gly Phe Asn
                1650            1655            1660

Val Ser Ile Gly Lys Asn Glu Gly Val Arg Glu Glu Lys Leu Cys Gly
        1665            1670            1675            1680

Asp Pro Trp Leu Lys Val Met Leu Phe Leu Gly Gln Asp Glu Asp Cys
                    1685            1690            1695

Glu Val Glu Glu Met Glu Ser Glu Cys Ser Asn Glu Gly Trp Phe Lys
                1700            1705            1710

Thr His Ile Pro Leu Ser Asn Leu Glu Ser Thr Arg Ala Arg Trp Val
                1715            1720            1725

Gly Lys Met Ala Leu Lys Glu Tyr Arg Glu Val Arg Cys Gly Tyr Glu
                1730            1735            1740

Met Thr Gln Gln Phe Phe Asp Glu His Arg Gly Gly Thr Gly Glu Gln
        1745            1750            1755            1760

Leu Ser Asn Ala Cys Glu Arg Phe Glu Ser Ile Tyr Pro Arg His Lys
                    1765            1770            1775

Gly Asn Asp Ser Ile Thr Phe Leu Met Ala Val Arg Lys Arg Leu Lys
                1780            1785            1790

Phe Ser Lys Pro Gln Val Glu Ala Ala Lys Leu Arg Arg Ala Lys Pro
                1795            1800            1805

Tyr Gly Lys Phe Leu Leu Asp Ser Phe Leu Ser Lys Ile Pro Leu Lys
                1810            1815            1820

Ala Ser His Asn Ser Ile Met Phe His Glu Ala Val Gln Glu Phe Glu
        1825            1830            1835            1840

Ala Lys Lys Ala Ser Lys Ser Ala Ala Thr Ile Glu Asn His Ala Gly
                    1845            1850            1855

Arg Ser Cys Arg Asp Trp Leu Leu Asp Val Ala Leu Ile Phe Met Lys
                1860            1865            1870
```

```
Ser Gln His Cys Thr Lys Phe Asp Asn Arg Leu Arg Val Ala Lys Ala
    1875                1880                1885

Gly Gln Thr Leu Ala Cys Phe Gln His Ala Val Leu Val Arg Phe Ala
    1890                1895                1900

Pro Tyr Met Arg Tyr Ile Glu Lys Lys Leu Met Gln Ala Leu Lys Pro
1905                1910                1915                1920

Asn Phe Tyr Ile His Ser Gly Lys Gly Leu Asp Leu Asn Glu Trp
        1925                1930                1935

Val Arg Thr Arg Gly Phe Thr Gly Ile Cys Thr Glu Ser Asp Tyr Glu
            1940                1945                1950

Ala Phe Asp Ala Ser Gln Asp His Phe Ile Leu Ala Phe Glu Leu Gln
        1955                1960                1965

Ile Met Lys Phe Leu Gly Leu Pro Glu Asp Leu Ile Leu Asp Tyr Glu
    1970                1975                1980

Phe Ile Lys Ile His Leu Gly Ser Lys Leu Gly Ser Phe Ser Ile Met
1985                1990                1995                2000

Arg Phe Thr Gly Glu Ala Ser Thr Phe Leu Phe Asn Thr Met Ala Asn
            2005                2010                2015

Met Leu Phe Thr Phe Leu Arg Tyr Glu Leu Thr Gly Ser Glu Ser Ile
            2020                2025                2030

Ala Phe Ala Gly Asp Asp Met Cys Ala Asn Arg Arg Leu Arg Leu Lys
        2035                2040                2045

Thr Glu His Glu Gly Phe Leu Asn Met Ile Cys Leu Lys Ala Lys Val
    2050                2055                2060

Gln Phe Val Ser Asn Pro Thr Phe Cys Gly Trp Cys Leu Phe Lys Glu
2065                2070                2075                2080

Gly Ile Phe Lys Lys Pro Gln Leu Ile Trp Glu Arg Ile Cys Ile Ala
            2085                2090                2095

Arg Glu Met Gly Asn Leu Glu Asn Cys Ile Asp Asn Tyr Ala Ile Glu
        2100                2105                2110

Val Ser Tyr Ala Tyr Arg Leu Gly Glu Leu Ala Ile Glu Met Met Thr
    2115                2120                2125

Glu Glu Glu Val Glu Ala His Tyr Asn Cys Val Arg Phe Leu Val Arg
    2130                2135                2140

Asn Lys His Lys Met Arg Cys Ser Ile Ser Gly Leu Phe Glu Ala Ile
2145                2150                2155                2160

Asp
```

(2) INFORMATION FOR SEQ ID NO:4:

(i) SEQUENCE CHARACTERISTICS:
        (A) LENGTH: 663 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
ATGAATAATT TAGTTAAAGC ATTGTCAGCA TTTGAGTTTG TAGGTGTTTT CAGTGTGCTT      60

AAATTTCCAG TAGTCATTCA TAGTGTGCCT GGTAGTGGTA AAAGTAGTTT AATAAGGGAG     120

CTAATTTCCG AGGATGAGAA TTTCATAGCT TTCACAGCAG GTGTTCCAGA CAGCCCTAAT     180

CTCACAGGAA GGTACATTAA GCCTTATTCT CCAGGGTGTG CAGTGCCAGG GAAAGTTAAT     240

ATACTTGATG AGTACTTGTC CGTCCAAGAT TTTTCAGGTT TTGATGTGCT GTTCTCGGAC     300
```

```
CCATACCAAA ACATCAGCAT TCCTAAAGAG GCACATTTCA TCAAGTCAAA AACTTGTAGG      360

TTTGGCGTGA ATACTTGCAA ATATCTTTCC TCCTTCGGTT TTAAGGTTAG CAGTGACGGT      420

TTGGACAAAG TCATTGTGGG GTCGCCTTTT ACACTAGATG TTGAAGGGGT GCTAATATGC      480

TTTGGTAAGG AGGCAGTGGA TCTCGCTGTT GCGCACAACT CTGAATTCAA ATTACCTTGT      540

GAAGTTAGAG GTTCAACTTT TAACGTCGTA ACTCTTTTGA AATCAAGAGA TCCAACCCCA      600

GAGGATAGGC ACTGGTTTTA CATTGCTGCT ACAAGACACA GGGAGAAATT GATAATCATG      660

CAG                                                                   663
```

(2) INFORMATION FOR SEQ ID NO:5:

(i) SEQUENCE CHARACTERISTICS:
        (A) LENGTH: 221 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Met Asn Asn Leu Val Lys Ala Leu Ser Ala Phe Glu Phe Val Gly Val
1               5                   10                  15

Phe Ser Val Leu Lys Phe Pro Val Val Ile His Ser Val Pro Gly Ser
            20                  25                  30

Gly Lys Ser Ser Leu Ile Arg Glu Leu Ile Ser Glu Asp Glu Asn Phe
        35                  40                  45

Ile Ala Phe Thr Ala Gly Val Pro Asp Ser Pro Asn Leu Thr Gly Arg
    50                  55                  60

Tyr Ile Lys Pro Tyr Ser Pro Gly Cys Ala Val Pro Gly Lys Val Asn
65                  70                  75                  80

Ile Leu Asp Glu Tyr Leu Ser Val Gln Asp Phe Ser Gly Phe Asp Val
                85                  90                  95

Leu Phe Ser Asp Pro Tyr Gln Asn Ile Ser Ile Pro Lys Glu Ala His
            100                 105                 110

Phe Ile Lys Ser Lys Thr Cys Arg Phe Gly Val Asn Thr Cys Lys Tyr
        115                 120                 125

Leu Ser Ser Phe Gly Phe Lys Val Ser Ser Asp Gly Leu Asp Lys Val
    130                 135                 140

Ile Val Gly Ser Pro Phe Thr Leu Asp Val Glu Gly Val Leu Ile Cys
145                 150                 155                 160

Phe Gly Lys Glu Ala Val Asp Leu Ala Val Ala His Asn Ser Glu Phe
                165                 170                 175

Lys Leu Pro Cys Glu Val Arg Gly Ser Thr Phe Asn Val Val Thr Leu
            180                 185                 190

Leu Lys Ser Arg Asp Pro Thr Pro Glu Asp Arg His Trp Phe Tyr Ile
        195                 200                 205

Ala Ala Thr Arg His Arg Glu Lys Leu Ile Ile Met Gln
    210                 215                 220
```

(2) INFORMATION FOR SEQ ID NO:6:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

ATGCCTTTTC AGCAGCCTGC GAATTGGGCA AAAACCATAA CTCCATTGAC AGTTGGCTTG      60

GGCATTGGGC TTGTGCTGCA TTTTCTGAGG AAGTCAAATC TACCTTATTC AGGGGACAAC     120

ATCCATCAAT TCCCTCACGG TGGGCGTTAC AGGGACGGTA CAAAAAGTAT AACTTACTGT     180

GGTCCAAAGC AATCCTTCCC CAGCTCTGGG ATATTCGGCC AATCTGAGAA TTTTGTGCCC     240

TTAATGCTTG TCATAGGTCT AATCGCATTC ATACATGTAT TGTCTGTTTG GAATTCTGGT     300

CTTGGTAGGA ATTGTAATTG CCATCCAAAT CCTTGCTCAT GTAGACAGCA G              351

(2) INFORMATION FOR SEQ ID NO:7:

(i) SEQUENCE CHARACTERISTICS:
            (A) LENGTH: 117 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:7:

Met Pro Phe Gln Gln Pro Ala Asn Trp Ala Lys Thr Ile Thr Pro Leu
    1               5                  10                  15

Thr Val Gly Leu Gly Ile Gly Leu Val Leu His Phe Leu Arg Lys Ser
                20                  25                  30

Asn Leu Pro Tyr Ser Gly Asp Asn Ile His Gln Phe Pro His Gly Gly
                35                  40                  45

Arg Tyr Arg Asp Gly Thr Lys Ser Ile Thr Tyr Cys Gly Pro Lys Gln
    50                  55                  60

Ser Phe Pro Ser Ser Gly Ile Phe Gly Gln Ser Glu Asn Phe Val Pro
    65                  70                  75                  80

Leu Met Leu Val Ile Gly Leu Ile Ala Phe Ile His Val Leu Ser Val
                    85                  90                  95

Trp Asn Ser Gly Leu Gly Arg Asn Cys Asn Cys His Pro Asn Pro Cys
                100                 105                 110

Ser Cys Arg Gln Gln
            115

(2) INFORMATION FOR SEQ ID NO:8:

(i) SEQUENCE CHARACTERISTICS:
            (A) LENGTH: 240 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

ATGTATTGTC TGTTTGGAAT TCTGGTCTTG GTAGGAATTG TAATTGCCAT CCAAATCCTT      60

GCTCATGTAG ACAGCAGTAG TGGCAACCAC CAAGGTTGCT TCATTAGGGC CACTGGAGAG     120

TCAATTTTGA TTGAAAACTG CGGCCCAAGT GAGGCCCTTG CATCCACTGT GAAGGAGGTG     180

CTGGGAGGTT TGAAGGCTTT AGGGGTTAGC CGTGCTGTTG AAGAAATTGA TTATCATTGT     240

(2) INFORMATION FOR SEQ ID NO:9:

(i) SEQUENCE CHARACTERISTICS:
            (A) LENGTH: 80 amino acids (B) TYPE: amino acid
       (C) STRANDEDNESS:
       (D) TOPOLOGY: linear (ii) MOLECULE TYPE: protein (xi) SEQUENCE DESCRIPTION: SEQ ID NO:9:

Met Tyr Cys Leu Phe Gly Ile Leu Val Leu Val Gly Ile Val Ile Ala
    1               5                   10                  15

Ile Gln Ile Leu Ala His Val Asp Ser Ser Gly Asn His Gln Gly
                20                  25                  30

Cys Phe Ile Arg Ala Thr Gly Glu Ser Ile Leu Ile Glu Asn Cys Gly
                    35                  40                  45

Pro Ser Glu Ala Leu Ala Ser Thr Val Lys Glu Val Leu Gly Gly Leu
        50                  55                  60

Lys Ala Leu Gly Val Ser Arg Ala Val Glu Glu Ile Asp Tyr His Cys
    65                  70                  75                  80

(2) INFORMATION FOR SEQ ID NO:10:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

ATGGCAAGTC AAATTGGGAA ACTCCCCGGT GAATCAAATG AGGCTTTTGA AGCCCGGCTA     60

AAATCGCTGG AGTTAGCTAG AGCTCAAAAG CAGCCGGAAG GTTCTAATGC ACCACCTACT    120

CTCAGTGGCA TTCTTGCCAA ACGCAAGAGG ATTATAGAGA ATGCACTTTC AAAGACGGTG    180

GACATGAGGG AGGTTTTGAA ACACGAAACG GTGGTGATTT CCCCAAATGT CATGGATGAA    240

GGTGCAATAG ACGAGCTGAT TCGTGCATTT GGTGAATCTG GCATAGCTGA AAGCGTGCAA    300

TTTGATGTGG CCATAGATAT AGCACGTCAC TGCTCTGATG TTGGTAGCTC CCAGAGTTCA    360

ACCCTGATTG GCAAGAGTCC ATTTTGTGAC CTAAACAGAT CAGAAATAGC TGGGATTATA    420

AGGGAGGTGA CCACATTACG TAGATTTTGC ATGTACTATG CAAAAATCGT GTGGAACATC    480

CATCTGGAGA CGGGGATACC ACCAGCTAAC TGGGCCAAGA AAGGATTTAA TGAGAATGAA    540

AAGTTTGCAG CCTTTGATTT TTTCTTGGGA GTCACAGATG AGAGTGCGCT TGAACCAAAG    600

GGTGGAATTA AAAGAGCTCC AACGAAAGCT GAGATGGTTG CTAATATCGC CTCTTTTGAG    660

GTTCAAGTGC TCAGACAAGC TATGGCTGAA GGCAAGCGGA GTTCCAACCT TGGAGAGATT    720

AGTGGTGGAA CGGCTGGTGC ACTCATCAAC AACCCCTTTT CAAATGTTAC ACATGAA      777

(2) INFORMATION FOR SEQ ID NO:11:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

Met Ala Ser Gln Ile Gly Lys Leu Pro Gly Glu Ser Asn Glu Ala Phe
    1               5                   10                  15

Glu Ala Arg Leu Lys Ser Leu Glu Leu Ala Arg Ala Gln Lys Gln Pro

```
                    20                  25                  30

Glu Gly Ser Asn Ala Pro Pro Thr Leu Ser Gly Ile Leu Ala Lys Arg
                     35                  40                  45

Lys Arg Ile Ile Glu Asn Ala Leu Ser Lys Thr Val Asp Met Arg Glu
         50                  55                  60

Val Leu Lys His Glu Thr Val Val Ile Ser Pro Asn Val Met Asp Glu
         65                  70                  75                  80

Gly Ala Ile Asp Glu Leu Ile Arg Ala Phe Gly Glu Ser Gly Ile Ala
                         85                  90                  95

Glu Ser Val Gln Phe Asp Val Ala Ile Asp Ile Ala Arg His Cys Ser
                        100                 105                 110

Asp Val Gly Ser Ser Gln Ser Ser Thr Leu Ile Gly Lys Ser Pro Phe
                    115                 120                 125

Cys Asp Leu Asn Arg Ser Glu Ile Ala Gly Ile Ile Arg Glu Val Thr
                130                 135                 140

Thr Leu Arg Arg Phe Cys Met Tyr Tyr Ala Lys Ile Val Trp Asn Ile
        145                 150                 155                 160

His Leu Glu Thr Gly Ile Pro Pro Ala Asn Trp Ala Lys Lys Gly Phe
                        165                 170                 175

Asn Glu Asn Glu Lys Phe Ala Ala Phe Asp Phe Phe Leu Gly Val Thr
                    180                 185                 190

Asp Glu Ser Ala Leu Glu Pro Lys Gly Gly Ile Lys Arg Ala Pro Thr
                195                 200                 205

Lys Ala Glu Met Val Ala Asn Ile Ala Ser Phe Glu Val Gln Val Leu
            210                 215                 220

Arg Gln Ala Met Ala Glu Gly Lys Arg Ser Ser Asn Leu Gly Glu Ile
        225                 230                 235                 240

Ser Gly Gly Thr Ala Gly Ala Leu Ile Asn Asn Pro Phe Ser Asn Val
                        245                 250                 255

Thr His Glu (2) INFORMATION FOR SEQ ID NO:12:

(i) SEQUENCE CHARACTERISTICS:
        (A) LENGTH: 2680 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GGCTGGGCAA ACTTTGGCCT GCTTTCAACA CGCCGTCTTG GTTCGCTTTG CACCCTACAT     60

GCGATACATT GAAAAGAAGC TTGTGCAGGC ATTGAAACCA AATTTCTACA TTCATTCTGG    120

CAAAGGTCTT GATGAGCTAA GTGAATGGGT TAGAGCCAGA GGTTTCACAG GTGTGTGTAC    180

TGAGTCAGAC TATGAAGCTT TTGATGCATC CCAAGATCAT TTCATCCTGG CATTTGAACT    240

GCAAATCATG AGATTTTTAG GACTGCCAGA AGATCTGATT TTAGATTATG AGTTCATCAA    300

AATTCATCTT GGGTCAAAGC TTGGCTCTTT TGCAATTATG AGATTCACAG GTGAGGCAAG    360

CACCTTCCTA TTCAATACTA TGGCCAACAT GCTATTCACT TTCCTGAGGT ATGAGTTGAC    420

AGGTTCTGAA TCAATTGCAT TTGCTGGAGA TGATATGTGT GCTAATCGCA GGTTAAGACT    480

CAAGACTGAG CACGCCGGCT TTCTAAACAT GATCTGTCTC AAAGCTAAGG TGCAGTTTGT    540

CACAAATCCC ACCTTCTGTG GATGGTGTTT GTTTAAAGAG GGAATCTTTA AAAACCCCA    600
```

```
GCTCATTTGG GAAAGGATCT GCATTGCTAG GGAAATGGGT AACTTGGACA ATTGCATTGA      660

CAATTACGCA ATTGAGGTGT CTTATGCTTA CAGACTTGGG GAATTGTCCA TAGGCGTGAT      720

GACTGAGGAG GAAGTTGAAG CACATTCTAA CTGCGTGCGT TTCCTGGTTC GCAATAAGCA      780

CAAGATGAGG TGCTCAATTT CTGGTTTGTT TGAAGTAATT GTTTAGGCCT TAAGTGTTTG      840

GCATGGTGTG AGTATTATGA ATAACTTAGT CAAAGCTTTG TCTGCTTTTG AATTTGTTGG      900

TGTGTTTTGT GTACTTAAAT TTCCAGTTGT TGTTCACAGT GTTCCAGGTA GCGGTAAAAG      960

TAGCCTAATA AGGGAGCTCA TTTCTGAAGA CGAGGCTTTT GTGGCCTTTA CAGCAGGTGT     1020

GCCAGACAGT CCAAATCTGA CAGGGAGGTA CATCAAGCCC TACGCTCCAG GGTGTGCAGT     1080

GCAAGGGAAA ATAAACATAC TTGATGAGTA CTTGTCTGTC TCTGATACTT CTGGCTTTGA     1140

TGTGCTGTTC TCAGACCCTT ACCAGAATGT CAGCATTCCA AGGGAGGCAC ACTTCATAAA     1200

AACCAAAACC TGTAGGTTTG GTACCAACAC CTGCAAGTAC CTTCAATCTT TTGGCTTTAA     1260

TGTTTGTAGT GATGGGTGG ATAAAGTTGT TGTAGGGTCG CCATTTGAAC TGGAGGTTGA     1320

GGGGGTTCTC ATTTGCTTTG GAAAGGAGGC TGTAGATCTA GCAGTTGCAC ACAATTCTGA     1380

CTTCAAGTTG CCCTGCGAGG TGCGGGGTTC AACATTTGAC GTTGTAACGT TATTGAAGTC     1440

CAGGGATCCA ACTTCAGAAG ATAAGCATTG GTTCTACGTT GCAGCCACAA GGCATCGAAG     1500

TAAACTGATA ATAATGCAGT AAAATGCCTT TTCAGCAACC TGCCAACTGG GCTAAGACCA     1560

TAACTCCATT AACTATTGGT TTGGGCATTG GGTTGGTTCT GCACTTCTTA AGGAAATCAA     1620

ATCTGCCATA TTCAGGAGAC AATATTCACC AGTTCCCACA CGGAGGGCAT TACAGGGACG     1680

GCACGAAGAG TATAACCTAT TGTGGCCCTA GGCAGTCATT CCCAAGCTCA GGAATATTCG     1740

GTCAGTCTGA AAATTTCGTA CCTCTAATAT TGGTCGTGAC TCTGGTCGCT TTTATACATG     1800

CGTTATCTCT TTGGAATTCT GGTCCTAGTA GGAGTTGCAA TTGCCATCCA AATCCTTGCA     1860

CATGTAGACA GCAGTAGTGG CAACCATCAA GGCTGTTTCA TAAGAGCCAC CGGGGAGTCA     1920

ATAGTAATTG AGAATTGTGG GCCGAGCGAG GCCCTAGCTG CTACAGTCAA AGAGGTGTTG     1980

GGCGGTCTAA AGGCTTTAGG GGTTAGCCAA AAGGTTGATG AAATTAATTA CAGTTGTTGA     2040

GACAGTTGAA TGGCAAGTCA AGTTGGAAAA TTGCCTGGCG AATCAAATGA AGCATATGAG     2100

GCTAGACTCA AGGCTTTAGA GTTAGCAAGG GCCCAAAAAG CTCCAGAAGT CTCCAACCAA     2160

CCTCCCACAC TTGGAGGCAT TCTAGCCAAA AGGAAAAGAG TGATTGAGAA TGCACTCTCA     2220

AAGACAGTGG ATATGCGTGA AGTCTTAAGG CATGAATCTG TTGTACTCTC CCCGAATGTA     2280

ATGGACGAGG GAGCAATAGA CGAGCTGATT CGTGCCTTTG GGGAGTCGGG CATAGCTGAA     2340

AATGTGCAGT TTGATGTTGC AATAGACATT GCTCGCCACT GTTCTGATGT GGGGAGCTCT     2400

CAGAGGTCAA CCCTTATTGG TAAAAGCCCC TTCTGTGAGT TAAATAGGTC TGAAATTGCC     2460

GGAATAATAA GGGAGGTGAC CACGCTGCGC AGATTTTGCA TGTACTACGC AAAGATTGTG     2520

TGGAACATCC ATTTGGAGAC GGGAATACCA CCAGCTAATT GGGCCAAGAA AGGATTTAAT     2580

GAGAATGAAA AGTTTGCAGC CTTTGACTTC TTCCTTGGAG TCACAGATGA AAGCGCGCTT     2640

GAGCCTAAGG GTGGAGTCAA GAGAGCTCCA ACAAAAGCAG                            2680
```

(2) INFORMATION FOR SEQ ID NO:13:

(i) SEQUENCE CHARACTERISTICS:
  (A) LENGTH: 767 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:13:

ATGCGATACA TTGAAAAGAA GCTTGTGCAG GCATTGAAAC CAAATTTCTA CATTCATTCT      60

GGCAAAGGTC TTGATGAGCT AAGTGAATGG GTTAGAGCCA GAGGTTTCAC AGGTGTGTGT     120

ACTGAGTCAG ACTATGAAGC TTTTGATGCA TCCCAAGATC ATTTCATCCT GGCATTTGAA     180

CTGCAAATCA TGAGATTTTT AGGACTGCCA GAAGATCTGA TTTTAGATTA TGAGTTCATC     240

AAAATTCATC TTGGGTCAAA GCTTGGCTCT TTTGCAATTA TGAGATTCAC AGGTGAGGCA     300

AGCACCTTCC TATTCAATAC TATGGCCAAC ATGCTATTCA CTTTCCTGAG GTATGAGTTG     360

ACAGGTTCTG AATCAATTGC ATTTGCTGGA GATGATATGT GTGCTAATCG CAGGTTAAGA     420

CTCAAGACTG AGCACGCCGG CTTTCTAAAC ATGATCTGTC TCAAAGCTAA GGTGCAGTTT     480

GTCACAAATC CCACCTTCTG TGGATGGTGT TTGTTTAAAG AGGGAATCTT TAAAAAACCC     540

CAGCTCATTT GGGAAAGGAT CTGCATTGCT AGGGAAATGG GTAACTTGGA CAATTGCATT     600

GACAATTACG CAATTGAGGT GTCTTATGCT TACAGACTTG GGGAATTGTC CATAGGCGTG     660

ATGACTGAGG AGGAAGTTGA AGCACATTCT AACTGCGTGC GTTTCCTGGT TCGCAATAAG     720

CACAAGATGA GGTGCTCAAT TTCTGGTTTG TTTGAAGTAA TTGTTTA                   767

(2) INFORMATION FOR SEQ ID NO:14:

(i) SEQUENCE CHARACTERISTICS:
        (A) LENGTH: 255 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

Met Arg Tyr Ile Glu Lys Lys Leu Val Gln Ala Leu Lys Pro Asn Phe
    1               5                   10                  15

Tyr Ile His Ser Gly Lys Gly Leu Asp Glu Leu Ser Glu Trp Val Arg
                    20                  25                  30

Ala Arg Gly Phe Thr Gly Val Cys Thr Glu Ser Asp Tyr Glu Ala Phe
                35                  40                  45

Asp Ala Ser Gln Asp His Phe Ile Leu Ala Phe Glu Leu Gln Ile Met
            50                  55                  60

Arg Phe Leu Gly Leu Pro Glu Asp Leu Ile Leu Asp Tyr Glu Phe Ile
    65                  70                  75                  80

Lys Ile His Leu Gly Ser Lys Leu Gly Ser Phe Ala Ile Met Arg Phe
                    85                  90                  95

Thr Gly Glu Ala Ser Thr Phe Leu Phe Asn Thr Met Ala Asn Met Leu
                100                 105                 110

Phe Thr Phe Leu Arg Tyr Glu Leu Thr Gly Ser Glu Ser Ile Ala Phe
                115                 120                 125

Ala Gly Asp Asp Met Cys Ala Asn Arg Arg Leu Arg Leu Lys Thr Glu
            130                 135                 140

His Ala Gly Phe Leu Asn Met Ile Cys Leu Lys Ala Lys Val Gln Phe
    145                 150                 155                 160

Val Thr Asn Pro Thr Phe Cys Gly Trp Cys Leu Phe Lys Glu Gly Ile
                    165                 170                 175

Phe Lys Lys Pro Gln Leu Ile Trp Glu Arg Ile Cys Ile Ala Arg Glu
                180                 185                 190

```
    Met Gly Asn Leu Asp Asn Cys Ile Asp Asn Tyr Ala Ile Glu Val Ser
            195                 200                 205

Tyr Ala Tyr Arg Leu Gly Glu Leu Ser Ile Gly Val Met Thr Glu Glu
            210                 215                 220

Glu Val Glu Ala His Ser Asn Cys Val Arg Phe Leu Val Arg Asn Lys
    225                 230                 235                 240

His Lys Met Arg Cys Ser Ile Ser Gly Leu Phe Glu Val Ile Val
                    245                 250                 255

(2) INFORMATION FOR SEQ ID NO:15:

(i) SEQUENCE CHARACTERISTICS:
        (A) LENGTH: 666 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ATGAATAACT TAGTCAAAGC TTTGTCTGCT TTTGAATTTG TTGGTGTGTT TTGTGTACTT      60

AAATTTCCAG TTGTTGTTCA CAGTGTTCCA GGTAGCGGTA AAAGTAGCCT AATAAGGGAG     120

CTCATTTCTG AAGACGAGGC TTTTGTGGCC TTTACAGCAG GTGTGCCAGA CAGTCCAAAT     180

CTGACAGGGA GGTACATCAA GCCCTACGCT CCAGGGTGTG CAGTGCAAGG GAAAATAAAC     240

ATACTTGATG AGTACTTGTC TGTCTCTGAT ACTTCTGGCT TTGATGTGCT GTTCTCAGAC     300

CCTTACCAGA ATGTCAGCAT TCCAAGGGAG GCACACTTCA TAAAAACCAA AACCTGTAGG     360

TTTGGTACCA CACCTGCAA GTACCTTCAA TCTTTTGGCT TTAATGTTTG TAGTGATGGG      420

GTGGATAAAG TTGTTGTAGG GTCGCCATTT GAACTGGAGG TTGAGGGGGT TCTCATTTGC     480

TTTGAAAGG AGGCTGTAGA TCTAGCAGTT GCACACAATT CTGACTTCAA GTTGCCCTGC      540

GAGGTGCGGG GTTCAACATT TGACGTTGTA ACGTTATTGA AGTCCAGGGA TCCAACTTCA     600

GAAGATAAGC ATTGGTTCTA CGTTGCAGCC ACAAGGCATC GAAGTAAACT GATAATAATG     660

CAGTAA                                                                666

(2) INFORMATION FOR SEQ ID NO:16:

(i) SEQUENCE CHARACTERISTICS:
        (A) LENGTH: 221 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

Met Asn Asn Leu Val Lys Ala Leu Ser Ala Phe Glu Phe Val Gly Val
    1               5                   10                  15

Phe Cys Val Leu Lys Phe Pro Val Val His Ser Val Pro Gly Ser
                    20                  25                  30

Gly Lys Ser Ser Leu Ile Arg Glu Leu Ile Ser Glu Asp Glu Ala Phe
                    35                  40                  45

Val Ala Phe Thr Ala Gly Val Pro Asp Ser Pro Asn Leu Thr Gly Arg
            50                  55                  60

Tyr Ile Lys Pro Tyr Ala Pro Gly Cys Ala Val Gln Gly Lys Ile Asn
    65                  70                  75                  80

Ile Leu Asp Glu Tyr Leu Ser Val Ser Asp Thr Ser Gly Phe Asp Val
                    85                  90                  95
```

-continued

```
Leu Phe Ser Asp Pro Tyr Gln Asn Val Ser Ile Pro Arg Glu Ala His
                100                 105                 110

Phe Ile Lys Thr Lys Thr Cys Arg Phe Gly Thr Asn Thr Cys Lys Tyr
            115                 120                 125

Leu Gln Ser Phe Gly Phe Asn Val Cys Ser Asp Gly Val Asp Lys Val
        130                 135                 140

Val Val Gly Ser Pro Phe Glu Leu Glu Val Glu Gly Val Leu Ile Cys
145                 150                 155                 160

Phe Gly Lys Glu Ala Val Asp Leu Ala Val Ala His Asn Ser Asp Phe
                165                 170                 175

Lys Leu Pro Cys Glu Val Arg Gly Ser Thr Phe Asp Val Val Thr Leu
            180                 185                 190

Leu Lys Ser Arg Asp Pro Thr Ser Glu Asp Lys His Trp Phe Tyr Val
        195                 200                 205

Ala Ala Thr Arg His Arg Ser Lys Leu Ile Ile Met Gln
210                 215                 220
```

(2) INFORMATION FOR SEQ ID NO:17:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
ATGCCTTTTC AGCAACCTGC CAACTGGGCT AAGACCATAA CTCCATTAAC TATTGGTTTG      60

GGCATTGGGT TGGTTCTGCA CTTCTTAAGG AAATCAAATC TGCCATATTC AGGAGACAAT     120

ATTCACCAGT TCCCACACGG AGGGCATTAC AGGGACGGCA CGAAGAGTAT AACCTATTGT     180

GGCCCTAGGC AGTCATTCCC AAGCTCAGGA ATATTCGGTC AGTCTGAAAA TTTCGTACCT     240

CTAATATTGG TCGTGACTCT GGTCGCTTTT ATACATGCGT TATCTCTTTG GAATTCTGGT     300

CCTAGTAGGA GTTGCAATTG CCATCCAAAT CCTTGCACAT GTAGACAGCA GTAG           354
```

(2) INFORMATION FOR SEQ ID NO:18:

(i) SEQUENCE CHARACTERISTICS:
        (A) LENGTH: 117 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:18:

```
Met Pro Phe Gln Gln Pro Ala Asn Trp Ala Lys Thr Ile Thr Pro Leu
1               5                   10                  15

Thr Ile Gly Leu Gly Ile Gly Leu Val Leu His Phe Leu Arg Lys Ser
            20                  25                  30

Asn Leu Pro Tyr Ser Gly Asp Asn Ile His Gln Phe Pro His Gly Gly
        35                  40                  45

His Tyr Arg Asp Gly Thr Lys Ser Ile Thr Tyr Cys Gly Pro Arg Gln
    50                  55                  60

Ser Phe Pro Ser Ser Gly Ile Phe Gly Gln Ser Glu Asn Phe Val Pro
65                  70                  75                  80

Leu Ile Leu Val Val Thr Leu Val Ala Phe Ile His Ala Leu Ser Leu
```

```
                   85                  90                  95
        Trp Asn Ser Gly Pro Ser Arg Ser Cys Asn Cys His Pro Asn Pro Cys
                    100                 105                 110

Thr Cys Arg Gln Gln
             115
```

(2) INFORMATION FOR SEQ ID NO:19:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
ATGCGTTATC TCTTTGGAAT TCTGGTCCTA GTAGGAGTTG CAATTGCCAT CCAAATCCTT      60

GCACATGTAG ACAGCAGTAG TGGCAACCAT CAAGGCTGTT TCATAAGAGC CACCGGGGAG     120

TCAATAGTAA TTGAGAATTG TGGGCCGAGC GAGGCCCTAG CTGCTACAGT CAAAGAGGTG     180

TTGGGCGGTC TAAAGGCTTT AGGGGTTAGC CAAAAGGTTG ATGAAATTAA TTACAGTTGT     240

TGA                                                                   243
```

(2) INFORMATION FOR SEQ ID NO:20:

(i) SEQUENCE CHARACTERISTICS:
        (A) LENGTH: 80 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:20:

```
        Met Arg Tyr Leu Phe Gly Ile Leu Val Leu Val Gly Val Ala Ile Ala
        1                   5                   10                  15

Ile Gln Ile Leu Ala His Val Asp Ser Ser Gly Asn His Gln Gly
                     20                  25                  30

Cys Phe Ile Arg Ala Thr Gly Glu Ser Ile Val Ile Glu Asn Cys Gly
                     35                  40                  45

Pro Ser Glu Ala Leu Ala Ala Thr Val Lys Glu Val Leu Gly Gly Leu
             50                  55                  60

Lys Ala Leu Gly Val Ser Gln Lys Val Asp Glu Ile Asn Tyr Ser Cys
        65                  70                  75                  80
```

(2) INFORMATION FOR SEQ ID NO:21:

(i) SEQUENCE CHARACTERISTICS:
        (A) LENGTH: 631 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
ATGGCAAGTC AAGTTGGAAA ATTGCCTGGC GAATCAAATG AAGCATATGA GGCTAGACTC      60

AAGGCTTTAG AGTTAGCAAG GGCCCAAAAA GCTCCAGAAG TCTCCAACCA ACCTCCCACA     120

CTTGGAGGCA TTCTAGCCAA AAGGAAAGA GTGATTGAGA ATGCACTCTC AAAGACAGTC     180

GATATGCGTG AAGTCTTAAG GCATGAATCT GTTGTACTCT CCCCGAATGT AATGGACGAG     240
```

```
GGAGCAATAG ACGAGCTGAT TCGTGCCTTT GGGGAGTCGG GCATAGCTGA AAATGTGCAG      300

TTTGATGTTG CAATAGACAT TGCTCGCCAC TGTTCTGATG TGGGGAGCTC TCAGAGGTCA      360

ACCCTTATTG GTAAAAGCCC CTTCTGTGAG TTAAATAGGT CTGAAATTGC CGGAATAATA      420

AGGGAGGTGA CCACGCTGCG CAGATTTTGC ATGTACTACG CAAAGATTGT GTGGAACATC      480

CATTTGGAGA CGGGAATACC ACCAGCTAAT TGGGCCAAGA AGGATTTAA TGAGAATGAA       540

AAGTTTGCAG CCTTTGACTT CTTCCTTGGA GTCACAGATG AAAGCGCGCT TGAGCCTAAG      600

GGTGGAGTCA AGAGAGCTCC AACAAAAGCA G                                     631
```

(2) INFORMATION FOR SEQ ID NO:22:

(i) SEQUENCE CHARACTERISTICS:
        (A) LENGTH: 210 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:22:

```
Met Ala Ser Gln Val Gly Lys Leu Pro Gly Glu Ser Asn Glu Ala Tyr
1               5                   10                  15

Glu Ala Arg Leu Lys Ala Leu Glu Leu Ala Arg Ala Gln Lys Ala Pro
            20                  25                  30

Glu Val Ser Asn Gln Pro Pro Thr Leu Gly Gly Ile Leu Ala Lys Arg
        35                  40                  45

Lys Arg Val Ile Glu Asn Ala Leu Ser Lys Thr Val Asp Met Arg Glu
    50                  55                  60

Val Leu Arg His Glu Ser Val Val Leu Ser Pro Asn Val Met Asp Glu
65                  70                  75                  80

Gly Ala Ile Asp Glu Leu Ile Arg Ala Phe Gly Glu Ser Gly Ile Ala
                85                  90                  95

Glu Asn Val Gln Phe Asp Val Ala Ile Asp Ile Ala Arg His Cys Ser
            100                 105                 110

Asp Val Gly Ser Ser Gln Arg Ser Thr Leu Ile Gly Lys Ser Pro Phe
        115                 120                 125

Cys Glu Leu Asn Arg Ser Glu Ile Ala Gly Ile Ile Arg Glu Val Thr
    130                 135                 140

Thr Leu Arg Arg Phe Cys Met Tyr Tyr Ala Lys Ile Val Trp Asn Ile
145                 150                 155                 160

His Leu Glu Thr Gly Ile Pro Pro Ala Asn Trp Ala Lys Lys Gly Phe
                165                 170                 175

Asn Glu Asn Glu Lys Phe Ala Ala Phe Asp Phe Phe Leu Gly Val Thr
            180                 185                 190

Asp Glu Ser Ala Leu Glu Pro Lys Gly Gly Val Lys Arg Ala Pro Thr
        195                 200                 205

Lys Ala
    210
```

(2) INFORMATION FOR SEQ ID NO:23:

(i) SEQUENCE CHARACTERISTICS:
        (A) LENGTH: 2009 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
GAAGCTAGCA CATTTCTGTT CAACACTATG GCTAACATGT TGTTCACTTT TCTGAGATAT      60
GAACTGACGG GTTCAGAGTC AATAGCATTT GCAGGGATG  ATATGTGTGC TAATAGAAGG     120
TTGCGGCTTA AAACGGAGCA TGAGGGTTTT CTGAACATGA TCTGCCTTAA GGCCAAGGTT     180
CAGTTTGTTT CCAACCCCAC ATTCTGTGGA TGGTGCTTAT TTAAGGAGGG AATCTTCAAG     240
AAACCTCAAC TAATTTGGGA GCGAATATGC ATAGCCAGAG AGATGGGCAA TCTGGAGAAC     300
TGTATTGACA ATTATGCGAT AGAAGTGTCC TATGCATATA GATTGGGTGA GCTATCAATT     360
GAAATGATGA CAGAAGAAGA AGTGGAGGCA CACTACAATT GTGTGAGGTT CCTGGTTAGG     420
AACAAGCATA AGATGAGGTG CTCAATTTCA GGCCTGTTTG AAGTGGTTGA TTAGGCCTTA     480
AGTATTTGGC GTTGTTCGAG TTATTATGAA TAATTTAGTT AAAGCATTAT CAGCCTTCGA     540
GTTTATAGGT GTTTTCAATG TGCTCAAATT TCCAGTTGTT ATACATAGTG TGCCTGGTAG     600
TGGTAAGAGT AGCTTAATAA GGGAATTAAT CTCAGAGGAC GAGAGTTTCG TGGCTTTCAC     660
AGCAGGTGTT CCAGACAGTC CTAACCTCAC AGGGAGGTAC ATCAAGCCTT ACTCACCAGG     720
ATGCGCAGTG CAAGGAAAAG TGAATATACT TGATGAGTAC TTGTCCGTTC AAGACATTTC     780
GGGTTTTGAT GTACTGTTTT CAGACCCGTA CCAGAATATC AGTATTCCCC AAGAGGCGCA     840
TTTCATTAAG TCCAAGACTT GTAGGTTTGG TGTGAACACT TGCAAATACC TTTCCTCTTT     900
CGGTTTCGAA GTTAGCAGCG ACGGGCTGGA CGACGTCATT GTGGGATCGC CCTTCACTCT     960
AGATGTTGAA GGGGTGCTGA TATGTTTTGG CAAGGAGGCG GTAGATCTCG CTGTTGCGCA    1020
CAACTCTGAA TTCAAGTTGC CGTGTGAGGT TCGAGGTTCA ACCTTCAATG TGGTAACCCT    1080
TTTGAAATCA AGAGACCCAA CCCCAGAGGA CAGGCACTGG TTTTACATCG CTGCCACAAG    1140
ACATAGGAAG AAATTGGTCA TTATGCAGTA AAATGCCTTT TCAGCAGCCT GCTAATTGGG    1200
CAAAAACCAT AACTCCATTG ACTATTGGCT TAGGAATTGG ACTTGTGCTG CATTTTCTGA    1260
GAAAGTCAAA TCTACCATAT TCAGGAGACA ACATCCATCA ATTTCCTCAC GGGGGCGTT     1320
ACCGGGACGG CACAAAAAGT ATAACTTACT GTGGCCCTAA GCAGTCCTTC CCCAGTTCAG    1380
GAATATTTGG TCAGTCTGAG AATTTTGTGC CCTTAATGCT TGTCATAGGT CTAATTGCAT    1440
TCATACATGT ATTGTCTGTT TGGAATTCTG GTCTTGGTAG GAATTGCAAT TGCCATCCAA    1500
ATCCTTGCTC ATGTAGACAA CAGTAGTGGC AGTCACCAAG GTTGCTTTAT CAGGGCCACT    1560
GGAGAGTCTA TTTTGATTGA AAATTGTGGC CCAAGCGAGG CCCTTGCATC AACAGTGAGG    1620
GAGGTGTTGG GGGGTTTGAA GGCTTTAGGA ATTAGCCATA CTACTGAAGA AATTGATTAT    1680
CGTTGTTAAA TTGGTTAAAT GGCGAGTCAA GTTGGTAAGC TCCCCGGAGA ATCAAATGAG    1740
GCATTTGAAG CCCGGCTGAA ATCACTGGAG TTGGCTAGAG CTCAAAAGCA GCCAGAAGGT    1800
TCAAACACAC CGCCTACTCT CAGTGGTGTG CTTGCCAAAC GTAAGAGGGT TATTGAGAAT    1860
GCACTCTCAA AGACAGTGGA CATGAGGGAG GTGTTGAAAC ACGAAACGGT TGTAATTTCC    1920
CCAAATGTCA TGGATGAGGG TGCAATAGAT GAACTGATTC GTGCATTCGG AGAATCAGGC    1980
ATAGCTGAGA GCGCACAATT TGATGTGGC                                     2009
```

(2) INFORMATION FOR SEQ ID NO:24:

(i) SEQUENCE CHARACTERISTICS:
        (A) LENGTH: 447 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:24:

GAAGCTAGCA CATTTCTGTT CAACACTATG GCTAACATGT TGTTCACTTT TCTGAGATAT     60

GAACTGACGG GTTCAGAGTC AATAGCATTT GCAGGGGATG ATATGTGTGC TAATAGAAGG    120

TTGCGGCTTA AAACGGAGCA TGAGGGTTTT CTGAACATGA TCTGCCTTAA GGCCAAGGTT    180

CAGTTTGTTT CCAACCCCAC ATTCTGTGGA TGGTGCTTAT TTAAGGAGGG AATCTTCAAG    240

AAACCTCAAC TAATTTGGGA GCGAATATGC ATAGCCAGAG AGATGGGCAA TCTGGAGAAC    300

TGTATTGACA ATTATGCGAT AGAAGTGTCC TATGCATATA GATTGGGTGA GCTATCAATT    360

GAAATGATGA CAGAAGAAGA AGTGGAGGCA CACTACAATT GTGTGAGGTT CCTGGTTAGG    420

AACAAGCATA AGATGAGGTG CTCAATT                                        447

(2) INFORMATION FOR SEQ ID NO:25:

(i) SEQUENCE CHARACTERISTICS:
        (A) LENGTH: 149 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:25:

Glu Ala Ser Thr Phe Leu Phe Asn Thr Met Ala Asn Met Leu Phe Thr
    1               5                  10                  15

Phe Leu Arg Tyr Glu Leu Thr Gly Ser Glu Ser Ile Ala Phe Ala Gly
                20                  25                  30

Asp Asp Met Cys Ala Asn Arg Arg Leu Arg Leu Lys Thr Glu His Glu
            35                  40                  45

Gly Phe Leu Asn Met Ile Cys Leu Lys Ala Lys Val Gln Phe Val Ser
        50                  55                  60

Asn Pro Thr Phe Cys Gly Trp Cys Leu Phe Lys Glu Gly Ile Phe Lys
    65                  70                  75                  80

Lys Pro Gln Leu Ile Trp Glu Arg Ile Cys Ile Ala Arg Glu Met Gly
                    85                  90                  95

Asn Leu Glu Asn Cys Ile Asp Asn Tyr Ala Ile Glu Val Ser Tyr Ala
                100                 105                 110

Tyr Arg Leu Gly Glu Leu Ser Ile Glu Met Met Thr Glu Glu Glu Val
                115                 120                 125

Glu Ala His Tyr Asn Cys Val Arg Phe Leu Val Arg Asn Lys His Lys
        130                 135                 140

Met Arg Cys Ser Ile
    145

(2) INFORMATION FOR SEQ ID NO:26:

(i) SEQUENCE CHARACTERISTICS:
        (A) LENGTH: 666 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

ATGAATAATT TAGTTAAAGC ATTATCAGCC TTCGAGTTTA TAGGTGTTTT CAATGTGCTC     60

```
AAATTTCCAG TTGTTATACA TAGTGTGCCT GGTAGTGGTA AGAGTAGCTT AATAAGGGAA        120

TTAATCTCAG AGGACGAGAG TTTCGTGGCT TCACAGCAG GTGTTCCAGA CAGTCCTAAC         180

CTCACAGGGA GGTACATCAA GCCTTACTCA CCAGGATGCG CAGTGCAAGG AAAAGTGAAT       240

ATACTTGATG AGTACTTGTC CGTTCAAGAC ATTTCGGGTT TTGATGTACT GTTTTCAGAC       300

CCGTACCAGA ATATCAGTAT TCCCCAAGAG GCGCATTTCA TTAAGTCCAA GACTTGTAGG       360

TTTGGTGTGA ACACTTGCAA ATACCTTTCC TCTTTCGGTT TCGAAGTTAG CAGCGACGGG       420

CTGGACGACG TCATTGTGGG ATCGCCCTTC ACTCTAGATG TTGAAGGGGT GCTGATATGT       480

TTTGGCAAGG AGGCGGTAGA TCTCGCTGTT GCGCACAACT CTGAATTCAA GTTGCCGTGT       540

GAGGTTCGAG GTTCAACCTT CAATGTGGTA ACCCTTTTGA AATCAAGAGA CCCAACCCCA       600

GAGGACAGGC ACTGGTTTTA CATCGCTGCC ACAAGACATA GGAAGAAATT GGTCATTATG       660

CAGTAA                                                                   666
```

(2) INFORMATION FOR SEQ ID NO:27:

(i) SEQUENCE CHARACTERISTICS:
        (A) LENGTH: 221 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:27:

```
Met Asn Asn Leu Val Lys Ala Leu Ser Ala Phe Glu Phe Ile Gly Val
1               5                   10                  15

Phe Asn Val Leu Lys Phe Pro Val Val Ile His Ser Val Pro Gly Ser
                20                  25                  30

Gly Lys Ser Ser Leu Ile Arg Glu Leu Ile Ser Glu Asp Glu Ser Phe
            35                  40                  45

Val Ala Phe Thr Ala Gly Val Pro Asp Ser Pro Asn Leu Thr Gly Arg
        50                  55                  60

Tyr Ile Lys Pro Tyr Ser Pro Gly Cys Ala Val Gln Gly Lys Val Asn
65                  70                  75                  80

Ile Leu Asp Glu Tyr Leu Ser Val Gln Asp Ile Ser Gly Phe Asp Val
                85                  90                  95

Leu Phe Ser Asp Pro Tyr Gln Asn Ile Ser Ile Pro Gln Glu Ala His
            100                 105                 110

Phe Ile Lys Ser Lys Thr Cys Arg Phe Gly Val Asn Thr Cys Lys Tyr
        115                 120                 125

Leu Ser Ser Phe Gly Phe Glu Val Ser Ser Asp Gly Leu Asp Asp Val
    130                 135                 140

Ile Val Gly Ser Pro Phe Thr Leu Asp Val Glu Gly Val Leu Ile Cys
145                 150                 155                 160

Phe Gly Lys Glu Ala Val Asp Leu Ala Val Ala His Asn Ser Glu Phe
                165                 170                 175

Lys Leu Pro Cys Glu Val Arg Gly Ser Thr Phe Asn Val Val Thr Leu
            180                 185                 190

Leu Lys Ser Arg Asp Pro Thr Pro Glu Asp Arg His Trp Phe Tyr Ile
        195                 200                 205

Ala Ala Thr Arg His Arg Lys Lys Leu Val Ile Met Gln
    210                 215                 220
```

-continued (2) INFORMATION FOR SEQ ID NO:28:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
ATGCCTTTTC AGCAGCCTGC TAATTGGGCA AAAACCATAA CTCCATTGAC TATTGGCTTA      60

GGAATTGGAC TTGTGCTGCA TTTTCTGAGA AAGTCAAATC TACCATATTC AGGAGACAAC     120

ATCCATCAAT TTCCTCACGG GGGGCGTTAC CGGGACGGCA CAAAAAGTAT AACTTACTGT     180

GGCCCTAAGC AGTCCTTCCC CAGTTCAGGA ATATTTGGTC AGTCTGAGAA TTTTGTGCCC     240

TTAATGCTTG TCATAGGTCT AATTGCATTC ATACATGTAT TGTCTGTTTG GAATTCTGGT     300

CTTGGTAGGA ATTGCAATTG CCATCCAAAT CCTTGCTCAT GTAGACAACA GTAG           354
```

(2) INFORMATION FOR SEQ ID NO:29:

(i) SEQUENCE CHARACTERISTICS:
        (A) LENGTH: 116 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:29:

```
    Met Pro Phe Gln Gln Pro Ala Asn Trp Ala Lys Thr Ile Thr Pro Leu
    1               5                  10                  15

Thr Ile Gly Leu Gly Ile Gly Leu Val Leu His Phe Leu Arg Lys Ser
                    20                  25                  30

Asn Leu Pro Tyr Ser Gly Asp Asn Ile His Gln Phe Pro His Gly Gly
                35                  40                  45

Arg Tyr Arg Asp Gly Thr Lys Ile Thr Tyr Cys Gly Pro Lys Gln Ser
            50                  55                  60

Phe Pro Ser Ser Gly Ile Phe Gly Gln Ser Glu Asn Phe Val Pro Leu
    65                  70                  75                  80

Met Leu Val Ile Gly Leu Ile Ala Phe Ile His Val Leu Ser Val Trp
                        85                  90                  95

Asn Ser Gly Leu Gly Arg Asn Cys Asn Cys His Pro Asn Pro Cys Ser
                    100                 105                 110

Cys Arg Gln Gln
            115
```

(2) INFORMATION FOR SEQ ID NO:30:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

```
ATGTATTGTC TGTTTGGAAT TCTGGTCTTG GTAGGAATTG CAATTGCCAT CCAAATCCTT      60

GCTCATGTAG ACAACAGTAG TGGCAGTCAC CAAGGTTGCT TATCAGGGC CACTGGAGAG     120

TCTATTTTGA TTGAAAATTG TGGCCCAAGC GAGGCCCTTG CATCAACAGT GAGGGAGGTG     180
```

```
TTGGGGGGTT TGAAGGCTTT AGGAATTAGC CATACTACTG AAGAAATTGA TTATCGTTGT      240

TAA                                                                   243
```

(2) INFORMATION FOR SEQ ID NO:31:

(i) SEQUENCE CHARACTERISTICS:
        (A) LENGTH: 80 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:31:

```
Met Tyr Cys Leu Phe Gly Ile Leu Val Leu Val Gly Ile Ala Ile Ala
1               5                   10                  15

Ile Gln Ile Leu Ala His Val Asp Asn Ser Ser Gly Ser His Gln Gly
            20                  25                  30

Cys Phe Ile Arg Ala Thr Gly Glu Ser Ile Leu Ile Glu Asn Cys Gly
                35                  40              45

Pro Ser Glu Ala Leu Ala Ser Thr Val Arg Glu Val Leu Gly Gly Leu
        50                  55                  60

Lys Ala Leu Gly Ile Ser His Thr Thr Glu Glu Ile Asp Tyr Arg Cys
65                  70                  75                  80
```

(2) INFORMATION FOR SEQ ID NO:32:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

```
ATGGCGAGTC AAGTTGGTAA GCTCCCCGGA GAATCAAATG AGGCATTTGA AGCCCGGCTG       60

AAATCACTGG AGTTGGCTAG AGCTCAAAAG CAGCCAGAAG GTTCAAACAC ACCGCCTACT      120

CTCAGTGGTG TGCTTGCCAA ACGTAAGAGG GTTATTGAGA ATGCACTCTC AAAGACAGTG      180

GACATGAGGG AGGTGTTGAA ACACGAAACG GTTGTAATTT CCCCAAATGT CATGGATGAG      240

GGTGCAATAG ATGAACTGAT TCGTGCATTC GGAGAATCAG GCATAGCTGA GAGCGCACAA      300

TTTGATGTGG C                                                          311
```

(2) INFORMATION FOR SEQ ID NO:33:

(i) SEQUENCE CHARACTERISTICS:
        (A) LENGTH: 103 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:33:

```
Met Ala Ser Gln Val Gly Lys Leu Pro Gly Glu Ser Asn Glu Ala Phe
1               5                   10                  15

Glu Ala Arg Leu Lys Ser Leu Glu Leu Ala Arg Ala Gln Lys Gln Pro
            20                  25                  30

Glu Gly Ser Asn Thr Pro Pro Thr Leu Ser Gly Val Leu Ala Lys Arg
        35                  40                  45
```

```
    Lys Arg Val Ile Glu Asn Ala Leu Ser Lys Thr Val Asp Met Arg Glu
         50                  55                  60

Val Leu Lys His Glu Thr Val Val Ile Ser Pro Asn Val Met Asp Glu
    65                  70                  75                  80

Gly Ala Ile Asp Glu Leu Ile Arg Ala Phe Gly Glu Ser Gly Ile Ala
                    85                  90                  95

Glu Ser Ala Gln Phe Asp Val
                100
```

(2) INFORMATION FOR SEQ ID NO:34:

(i) SEQUENCE CHARACTERISTICS:
        (A) LENGTH: 1206 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

```
GCAGGATTGA AGGCTGGCCA CTGTGTGATT TTTGATGAGG TCCAGTTGTT TCCTCCTGGA      60

TACATCGATC TATGCTTGCT TATTATACGT AGTGATGCTT TCATTTCACT TGCCGGTGAT     120

CCATGTCAAA GCACATATGA TTCGCAAAAG GATCGGGCAA TTTTGGGCGC TGAGCAGAGT     180

GACATACTTA GAATGCTTGA GGGCAAAACG TATAGGTATA ACATAGAAAG CAGGAGGTTT     240

GTGAACCCAA TGTTCGAATC AAGACTGCCA TGTCACTTCA AAAGGGTTC GATGACTGCC      300

GCTTTCGCTG ATTATGCAAT CTTCCATAAT ATGCATGACT TTCTCCTGGC GAGGTCAAAA     360

GGTCCTTTGG ATGCCGTTTT GGTTTCCAGT TTTGAGGAGA AAAAGATAGT CCAGTCCTAC     420

TTTGGAATGA AACAGCTCAC ACTCACATTT GGTGAATCAA CTGGGTTGAA TTTCAAAAAT     480

GGGGGAATTC TCATATCACA TGATTCCTTT CACACAGATG ATCGGCCGGT GGCTTACTGC     540

TTTATCTCGC TTCAGCCACA ATTTGGATTT GGTGAACATT ACAGGTCTGA GGGTGGAAAG     600

TTTCCTCTCG CACTTTGCTG GCAAACCCCT CTACCATTTT TTAACAGCCA AAAGTGGGGA     660

GAATGTCATA CGAGATTTGC TCCCAGGTGA GCCTAACTTC TTCAGTGGCT TAACGTTAG      720

CATTGGAAAG AATGAAGGTG TTAGGGAGGA GAAGTTATGT GGTGACCCAT GGTTAAAAGT     780

CATGCTTTTC CTGGGTCAAG ATGAGGATTG TGAAGTTGAA GAGATGGAGT CAGAGTGCTC     840

AAATGAAGAA TGGTTTAAAA CCCACATTCC CCTGAGTAAT CTGGAGTCAA CCAGGGCTAG     900

GTGGGTGGGT AAAATGGCTT TGAAAGAGTA TCGGGAGGTG CGTTGTGGTT ATGAAATGAC     960

TCAACAATTC TTTGATGAGC ATAGGGGTGG AACTGGTGAG CAACTGAGCA ATGCATGTGA    1020

GAGGTTTGAA AGCATTTACC CAAGGCATAA AGGAAATGAT TCAATAACCT TCCTTATGGC    1080

TGTCCGAAAG CGTCTCAAAT TTTCGAAGCC CCAGGTTGAA GCTGCCAAAC TGAGGCGGGC    1140

CAAACCATAT GGGAAATTCT TATTAGACTT TCCTATCCAA AATCCCATTG AAAGCCAGTC    1200

ATAATT                                                              1206
```

(2) INFORMATION FOR SEQ ID NO:35:

(i) SEQUENCE CHARACTERISTICS:
        (A) LENGTH: 1284 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

| | | | | | |
|---|---|---|---|---|---|
| ATTAACCCAA | ATGGTAAGAT | TTCCGCCTTG | TTTGATATAA | CCAATGAGCA | CATAAGGCAT | 60 |
| GTTGAGAAGA | TCGGCAATGG | CCCTCAGAGC | ATAAAAGTAG | ATGAGTTGAG | GAAGGTTAAG | 120 |
| CGATCCGCCC | TTGATCTTCT | TTCAATGAAT | GGGTCCAAAA | TAACCTATTT | TCCAAACTTT | 180 |
| GAGCGGGCTG | AAAAGTTGCA | AGGGTGCTTG | CTAGGGGGCC | TAACTGGTGT | CATAAGTGAT | 240 |
| GAAAAGTTCA | GTGATGCAAA | ACCCTGGCTT | TCTGGTATAT | CAACTGCGGA | TATAAAGCCA | 300 |
| AGAGAGCTAA | CTGTCGTGCT | TGGCACTTTT | GGGGCTGGAA | AGAGTTTCTT | GTATAAGAGT | 360 |
| TTCATGAAGA | GATCTGAGGG | AAAATTTGTA | ACTTTTGTTT | CCCCTAGACG | AGCCTTGGCA | 420 |
| AATTCAATCA | AAAATGATCT | TGAAATGGAT | GATGGCTGCA | AAGTTGCCAA | AGCAGGCAAA | 480 |
| TCAAAGAAGG | AAGGGTGGGA | TGTAGTGACC | TTTGAAGTTT | TCCTTAGAAA | AGTTTCTGGT | 540 |
| TTGAAAGCTG | GTCATTGTGT | GATTTTTGAT | GAGGTTCAGT | TGTTTCCCCC | TGGATACATC | 600 |
| GATCTGTGTT | TACTTGTCAT | ACGAAGTGAT | GCTTTCATTT | CACTTGCTGG | TGATCCATGC | 660 |
| CAGAGCACAT | ATGATTCACA | GAAGGATCGA | GCAATTTTGG | GAGCTGAGCA | GAGTGACATA | 720 |
| CTCAGACTGC | TTGAAGGAAA | GACATATAGG | TACAACATAG | AAAGCAGACG | TTTTGTGAAC | 780 |
| CCAATGTTTG | AATCTAGACT | ACCATGTCAC | TTCAAAAAGG | GTTCAATGAC | TGCAGCCTTT | 840 |
| GCTGATTATG | CAATCTTCCA | CAATATGCAT | GACTTCCTCC | TGGCGAGGTC | AAAAGGCCCC | 900 |
| TTGGATGCTG | TTCTAGTTTC | CAGTTTTGAG | GAGAAGAAAA | TAGTCCAATC | CTACTTTGGG | 960 |
| ATGAAGCAAC | TCACTCTCAC | ATTTGGTGAA | TCAACTGGGT | TGAACTTCAA | AAATGGAGGA | 1020 |
| ATTCTCATAT | CACATGACTC | CTTTCATACT | GACGATCGAC | GGTGGCTTAC | TGCTTTATCT | 1080 |
| CGATTCAGCC | ATAATTTGGA | TTTGGTGAAC | ATCACAGGTC | TTGAGGGTGG | AAAGTTTTCT | 1140 |
| CTCACATTTT | GCTGGTAAAC | CCCTTTACCA | CTTTTTGACG | GCTTAAAAGT | GGAGAGAATG | 1200 |
| TCATACGAGA | CCTGCTTCAG | GTGAGCCTAA | CTTCTTTTAG | GGGTTCAATG | TCAGCATTGG | 1260 |
| AAAAAAATGG | AAGGGGTTAG | AGAA | | | | 1284 |

(2) INFORMATION FOR SEQ ID NO:36:

(i) SEQUENCE CHARACTERISTICS:
        (A) LENGTH: 1402 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

| | | | | | |
|---|---|---|---|---|---|
| CATTTTTAAA | ATTTAATCCA | GTCGACTCAC | CAAATGTGAG | CGTAAGCTGT | TTCATCCCAA | 60 |
| AGTAGGACTG | GACTATTTTC | TTCTCCTCAA | AACTAGAAAC | CAGAATGGCA | TCCAAAGGAC | 120 |
| CTTTTGACCT | TGCCAGGAGG | AAATCATGCA | TATTGTGAAA | ATGGCATAA | TCAGCAAAGG | 180 |
| CAGCAGTCAT | TGTACCCTTT | TTGAAGTGAC | ATGGCAGTCG | AGATTCAAAC | ATTGGGTTCA | 240 |
| CAAATCTTCT | GCTTTCTATG | TTGTACCTAT | ACGTCTTGCC | TTCAAGTATT | TTGAGTATGT | 300 |
| CACTCTGCTC | AGCGCCCAAA | ATCGCCCGAT | CTTTTTGTGA | GTCATATGTG | CTCTGACATG | 360 |
| GGTCACCAGC | AAGTGAAATG | AAAGCATCAC | TACGTATAAT | AAGCAAACAT | AGATCGATGT | 420 |
| ATCCAGGGGG | AAACAACTGG | ACCTCATCGA | AAATTACACA | GTGACCAGCT | TTTAGACCTG | 480 |
| CAACTTTTCT | AAGGAAGACT | TCAAAAGTCA | CAACATCCCA | TCCTTCCTTC | TTTGACCTGC | 540 |
| CTGCTTTGGC | AACTTTGCAG | CTATCATCCA | TTTCAAGATC | ATTTTTGATT | GAATTCGCTA | 600 |

```
GAGCCCGTCT GGGGGAAACA AAAGTTACGA ATTTACCCTC AGATCTTTTC ATAAAGCTCT      660

TGTACAAAAA GCTTTTTCCG GCTCCAAATG TGCCAAGCAC AACAGTTAGC TCCCTCGGCT      720

TAATGTCAGT AGTTGATATA CCAGAAAGCC AGGGCTTTGC ATCACTGAAC TTCTCATCAC      780

TTATGACACC AGTTAGGCCT CCTAGCAGAC ACCCTTGCAA CTTTTCAGCC CGCTCAAAAC      840

TTGGGAAGTA GGTTACCTTG GACCCATTAA TTGAAAGAAG ATCAAGGGCG GATCGCTTGA      900

CCTTTCGCAA TTCATCTACT TTAATGCTCT GAGGGCCATT ACCTATCTTT TCAACATGCC      960

TTATGTGCTC ATTAGTTATG TCAAACAGAG CGGAAAACTT GCCATGTGGA TTAATCACCT     1020

CAATTTCCCC ATTTATGTCA CACTTAGCGC AAATGTCAAA AGCCTCAAAG CTTCAGCTA      1080

AGTTACATCA TGTTGAGCCT CCCCCTTGGC AAAGCTCCTC AAAAATGTGG TTAGTGCTAG     1140

GCCTGCACAA TAATTAACAC ATCAACTTCA CCCTGCCAAT GCTGAACAAT ACTGTTATCA     1200

TGCAACCATC CATGGGCAC ATGGTTGGAA TTGATTGATT TAAGGCAAAA ATCCCCACAG      1260

GGGGCATCCC CTTCCCCAAT TTCCACTGAT TCATACTCTG GCGTTATCAT ATCAACCCAA     1320

TGTGTCAAAT ACAAATAATG CAATCTCTCA TCTCCGATAA CATTTCCCCC ATTTTTTAAA     1380

AATGGTGGGG TGAAAATTGG AA                                              1402

(2) INFORMATION FOR SEQ ID NO:37:

(i) SEQUENCE CHARACTERISTICS:
        (A) LENGTH: 1236 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

GTGGTTTTTG CAACAACAGG CCCAGGTCTA TCTAAGGTTT TGGAAATGCC TCGAAGCAAG       60

AAGCAATCTA TTCTGGTTCT TGAGGGAGCC CTATCCATAG AAACGGACTA TGGCCCAAAA      120

GTTCTGGGAT CTTTTGAAGT TTTCAAAGGG GATTTCAACA TTAAAAAAAT GGAAGAAAGT      180

TCCATCTTTG TAATAACATA CAAGGCCCCA GTTAGATCTA CTGGCAAGTT GAGGGTCCAC      240

CAATCAGAAT GCTCATTTTC TGGATCCAAG GAGGTATTGC TGGGTTGTCA GATTGAGGCA      300

TGTGCTGATT ATGATATTGA TGATTTCAAT ACTTTCTTTG TACCTGGTGA TGGTAATTGC      360

TTTTGGCATT CAGTTGGTTT CTTACTCAGT ACTGACGGAC TTGCTTTGAA GGCCGGCATT      420

CGTTCTTTCG TGGAGAGTGA ACGCCTGGTG AGTCCAGATC TTTCAGCCCC AACCATTTCT      480

AAACAACTGG GGGAAAATGC TTATGCCGAG AATGAGATGA TTGCATTATT TTGTATTCGA      540

CACCATGTGA GGCTGATAGT GATTACGCCA GAGTATGAAG TCAGTTGGAA ATTTGGGGAA      600

GGTGAATGGC CCCTGTGCGG AATTCTTTGC CTTAAATCAA ATCACTTCCA ACCATGTGCC      660

CCATTGAATG GTTGCATGAT TACAGCTATT GCTTCAGCAC TTGGTAGGCG TGAAGTTGAT      720

GTGCTTAATT ATCTGTGCAG GCCTAGCACT AACCACATTT TGAGGAGCT TTGCCAAGGG       780

GGAGGCCTCA ACATGATGTA CTTAGCTGAA GCCTTTGAGG CTTTTGACAT TTGCGCTAAG     840

TGTGACATAA ATGGGAAAT TGAGGTGATT AATCCACATG GCAAGTTTTC CGCTCTGTTT      900

GACATAACTA ATGAGCACAT AAGGCATGTT GAAAAGATAG GTAATGGCCC TCAGAGCATT      960

AAAGTAGATG AATTGCGAAA GGTCAAGCGA TCTGCCCTTG ATCTTCTTTC AATTAATGGG     1020

TCCAAGGTAA CCTACTTCCC AAGTTTTGAG CGGGCTGAAA AGTTGCAAGG GTGTCTGCTA     1080

GGAGGCCTAA CTGGTGTCAT AAGTGATGAG AAAGTCAGTG ATGCAAAGCC CTGCTTTTTG     1140
```

| | |
|---|---|
| GTATATCAAC TACTGACATT AAGCCGAGGG AGCTAACTGT TGTGCTTTGG CACATTTGGA | 1200 |
| GCCCGGAAAA AGCCTTTTGT ACCAAGAGCT TTATTG | 1236 |

(2) INFORMATION FOR SEQ ID NO:38:

(i) SEQUENCE CHARACTERISTICS:
        (A) LENGTH: 1296 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

| | |
|---|---|
| GTCTAACTGG CGTTATAAGT GATGAGAAAT TCAGTGATGC AAAACCTTGG CTTTCTGGTA | 60 |
| TATCTACTAC AGATATTAAG CCAAGGGAAT TAACTGTTGT GCTTGGTACA TTTGGGGCTG | 120 |
| GGAAGAGTTT CTTGTACAAG AGTTTCATGA AAAGGTCTGA GGGTAAATTC GTAACCTTTG | 180 |
| TTTCTCCCAG ACGTGCTTTA GCAAATTCAA TCAAAAATGA TCTTGAAATG GATGATAGCT | 240 |
| GCAAAGTTGC CAAAGCAGGT AGGTCAAAGA AGGAAGGGTG GGATGTAGTA ACTTTTGAGG | 300 |
| TCTTCCTCAG AAAAGTTGCA GGATTGAAGG CTGGCCACTG TGTGATTTTT GATGAGGTCC | 360 |
| AGTTGTTTCC TCCTGGATAC ATCGATCTAT GCTTGCTTAT TATACGTAGT GATGCTTTCA | 420 |
| TTTCACTTGC CGGTGATCCA TGTCAAAGCA CATATGATTC GCAAAAGGAT CGGGCAATTT | 480 |
| TGGGCGCTGA GCAGAGTGAC ATACTTAGAA TGCTTGAGGG CAAAACGTAT AGGTATAACA | 540 |
| TAGAAAGCAG GAGGTTTGTG AACCCAATGT TCGAATCAAG ACTGCCATGT CACTTCAAAA | 600 |
| AGGGTTCGAT GACTGCCGCT TTCGCTGATT ATGCAATCTT CCATAATATG CATGACTTTC | 660 |
| TCCTGGCGAG GTCAAAAGGT CCTTTGGATG CCGTTTTGGT TTCCAGTTTT GAGGAGAAAA | 720 |
| AGATAGTCCA GTCCTACTTT GGAATGAAAC AGCTCACACT CACATTTGGT GAATCAACTG | 780 |
| GGTTGAATTT CAAAAATGGG GGAATTCTCA TATCACATGA TTCCTTTCAC ACAGATGATC | 840 |
| GGCGGTGGCT TACTGCTTTA TCTCGCTTCA GCCACAATTT GGATTTGGTG AACATTACAG | 900 |
| GTCTGAGGTG GAAAGTTTCC TCTCGCACTT TGCTGGCAAA CCCCTCTACC ATTTTTTAAC | 960 |
| AGCCAAAAGT GGGGAGAATG TCATACGAGA TTTGCTCCCA GGTGAGCCTA ACTTCTTCAG | 1020 |
| TGGCTTTAAC GTTAGCATTG GAAAGAATGA AGGTGTTAGG GAGGAGAAGT TATGTGGTGA | 1080 |
| CCCATGGTTA AAAGTCATGC TTTTCCTGGG TCAAGATGAG GATTGTGAAG TTGAAGAGAT | 1140 |
| GGAGTCAGAG TGCTCAAATG AAGAATGGTT TAAAACCCAC ATTCCCCTGA GTAATCTGGA | 1200 |
| GTCAACCAGG GCTAGGTGGG TGGGTAAAAT GGCCTTGAAA GAGTATCGGG AGGTGCGTTG | 1260 |
| TGGTTATGAA ATGACTCAAC AATTCTTTGA TGACAT | 1296 |

(2) INFORMATION FOR SEQ ID NO:39:

(i) SEQUENCE CHARACTERISTICS:
        (A) LENGTH: 907 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

| | |
|---|---|
| ATGTTCACCA AATCCAAATT ATGGCTGAAG CGAGATAAAG CAGTAAGCCA CCGCCGATCA | 60 |
| TCTGTGTGAA AGGAATCATG TGATATGAGA ATTCCCCCAT TTTTGAAATT CAACCCAGTT | 120 |
| GATTCACCAA ATGTGAGTGT GAGCTGTTTC ATTCCAAAGT AGGACTGGAC TATCTTTTTC | 180 |

-continued

```
TCCTCAAAAC TGGAAACCAA AACGGCATCC AAAGGACCTT TTGACCTCGC CAGGAGAAAG      240

TCATGCATAT TATGGAAGAT TGCATAATCA GCGAAAGCGG CAGTCATTGA GCCCTTTTTG      300

AATTGACATG GCAGTCTTGA TTCGAACATT GGATTCACAA ACCTCCTGCT TTCAATGTTA      360

TACCTATACG TCTTGCCCTC AAGCAGTCTA AGTATGTCAC TCTGCTCAGC GCCCAAAATT      420

GCCCGATCCT TTTGCGAATC ATATGTGCTT TGACATGGAT CACCGGCAAG TGAAATGAAA      480

GCATCACTAC GTATAATAAG CAAGCATAGA TCGATGTATC CAGGAGGAAA CAACTGGACC      540

TCATCGAAAA TCACACAGTG GCCAGCCTTC AATCCTGCAA CTTTTCTGAG GAAAACCTCA      600

AAAGTTACTA CATCCCACCC TTCCTTCTTT GACCTACCTG CTTTAGCAAC TTTGCAGCTA      660

TCATCCATTT CAAGATCATT TTTGATTGAA TTTGCTAAAG CACGTCTGGG AGAAACAAAG      720

GTTACGAATT TACCCTCAGA CCTTTTCATG AAACTCTTGT ACAAGAAACT CTTCCCAGCC      780

CCAAATGTAC CAAGCACGAC AGTCAACTCC CTTGGCTTAA TATCAGTAGT AGATATACCA      840

GAAAGCCAAG GTTTTGCATC ACTGAACTTC TCATCACTTA AACGCCAGT TAGGCCCCCT       900

AGCAAAC                                                                907

(2) INFORMATION FOR SEQ ID NO:40:

(i) SEQUENCE CHARACTERISTICS:
        (A) LENGTH: 1232 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

AGAATGCTTA TGCTGAGAAT GAGATGATTG CATTATTTTG CATCCGGCAC CATGTAAGGC       60

TTATAGTAAT AACACCGGAA TATGAAGTTA GTTGGAAATT TGGGGAAAGT GAGTGGCCCC      120

TATGTGGAAT TCTTTGCCTG AGGTCCAATC ACTTCCAACC ATGCGCCCCG CTGAATGGTT      180

GCATGATCAC GGCTATTGCT TCAGCACTTG GGAGGCGTGA GGTTGATGTG TTAAATTATC      240

TGTGTAGGCC TAGCACTAAT CACATCTTTG AGGAGCTGTG CCAGGGCGGA GGGCTTAATA     300

TGATGTACTT GGCTGAAGCT TTTGAGGCCT TTGACATTTG TGCAAAGTGC GACATAAATG      360

GGGAAATTGA GGTCATTAAC CCAAATGGCA AGATTTCCGC CTTGTTTGAT ATAACTAATG      420

AGCACATAAG GCATGTTGAG AAGATCAGCA ATGGCCCTCA GAGCATAAAA ATAGATGAGT      480

TGAGGAAGGT TAAGCGATCC CGCCTTGACC TTCTTTCAAT GAATGGGTCC AAAATAACCT      540

ATTTTCCAAA CTTTGAGCGG GCTGAAAAGT TGCAAGGGTG CTTGCTAGAG GGCCTGACTG      600

GTGTCATAAG TGATGAAAAG TTCAGTGATG CAAAACCTTG GCTTTCTGGT ATATCAACTG      660

CGGATATTAA GCCAAGAGAG CTAACTGTCG TGCTTGGCAC ATTTGGTGCT GGAAAGAGTT      720

TCTTGTATAA GAGTTTCATG AAGAGATCTG AAGGAAAATT TGTAACTTTT GTTTCCCCTA      780

GGCGAGCTTT GGCCAATTCG ATCAAGAATG ATCTTGAAAT GGATGATGGC TGCAAAGTTG      840

CCAAAGCAGG CAAGTCAAAG AAGGAAGGGT GGGATGTGGT AACATTTGAG GTTTTCCTTA      900

GAAAAGTTTC TGGTTTGAAG GCTGGTCATT GTGTGATTTT CGATGAGGTT CAGTTGTTTC      960

CCCCTGGATA TATCGATCTA TGTTTACTTG TCATACGCAG TGATGCTTTT ATTTCACTTG     1020

CCGGTGATCC ATGCCAGAGC ACATATGATT CACAAAAGGA TCGGGCAATT TTGGGAGCTG     1080

AGCAGAGTGA CATACTCAGA TTGCTTGAAG GAAAGACGTA TAGGTACAAC ATAGAAAGCA     1140

GACGTTTTGT GAACCCAATG TTTGAATTTA GACTACCATG TCACTTCAAA AAAGGGTTCA     1200
```

```
ATGACTGCTG CCTTTGCTGA TTATGCAATC TT                                        1232
```

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

```
GCTTCAGCAC TTGGAAGGCG                                                       20
```

(2) INFORMATION FOR SEQ ID NO:42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

```
CACACAGTGG CCAGCCT                                                          17
```

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

```
GGAGGTGCGT TGTGGTTATG                                                       20
```

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

```
CCCTGGCACT GCACACCC                                                         18
```

(2) INFORMATION FOR SEQ ID NO:45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

```
GGAGGTGACC ACATTACG                                                         18
```

(2) INFORMATION FOR SEQ ID NO:46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

CATCACGACT TGTCACAAAC C                                    21

(2) INFORMATION FOR SEQ ID NO:47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

TGGGCCTCCA CTTCTTC                                      17

(2) INFORMATION FOR SEQ ID NO:48:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

GGGGTTGCCT GAAGAT                                       16

(2) INFORMATION FOR SEQ ID NO:49:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

ACACCTGCTG TGAAAGC                                      17

(2) INFORMATION FOR SEQ ID NO:50:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

GGCCAAGGTT CAGTTTG                                      17

(2) INFORMATION FOR SEQ ID NO:51:

(i) SEQUENCE CHARACTERISTICS:
        (A) LENGTH: 20 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:51:

GATGAGGTCC AGTTGTTTCC                                                    20

(2) INFORMATION FOR SEQ ID NO:52:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:52:

ATCCAAAGGA CCTTTTGACC                                                    20

(2) INFORMATION FOR SEQ ID NO:53:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:53:

CTTGATGAGT ACTTGTC                                                       17

(2) INFORMATION FOR SEQ ID NO:54:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:54:

GCAAGGATTT GGATGGC                                                       17